US010472398B2

(12) United States Patent
Klapoetke et al.

(10) Patent No.: US 10,472,398 B2
(45) Date of Patent: Nov. 12, 2019

(54) CHANNELRHODOPSINS FOR OPTICAL CONTROL OF CELLS

(71) Applicants: Massachusetts Institute of Technology, Cambridge, MA (US); The Governors of The University of Alberta, Edmonton (CA)

(72) Inventors: Nathan Klapoetke, Cambridge, MA (US); Brian Yichiun Chow, Cambridge, MA (US); Edward Boyden, Chestnut Hill, MA (US); Gane Ka-Shu Wong, Edmontn (CA); Yongku Peter Cho, Cambridge, MA (US)

(73) Assignees: Massachusetts Institute of Technology, Cambridge, MA (US); The Governors of The University of Alberta, Edmonton, Alberta (CA)

( * ) Notice: Subject to any disclaimer, the term of this patent is extended or adjusted under 35 U.S.C. 154(b) by 53 days.

(21) Appl. No.: 14/357,635

(22) PCT Filed: Nov. 12, 2012

(86) PCT No.: PCT/US2012/064665
§ 371 (c)(1),
(2) Date: May 12, 2014

(87) PCT Pub. No.: WO2013/071231
PCT Pub. Date: May 16, 2013

(65) Prior Publication Data
US 2014/0324134 A1 Oct. 30, 2014

Related U.S. Application Data

(60) Provisional application No. 61/559,076, filed on Nov. 12, 2011.

(51) Int. Cl.
*C07K 14/405* (2006.01)
*A61N 5/06* (2006.01)
*C12N 13/00* (2006.01)
*G01N 33/487* (2006.01)
*A61K 41/00* (2006.01)
*G01N 33/50* (2006.01)
*A61K 38/00* (2006.01)

(52) U.S. Cl.
CPC ........ *C07K 14/405* (2013.01); *A61K 41/0023* (2013.01); *A61N 5/062* (2013.01); *C12N 13/00* (2013.01); *G01N 33/48728* (2013.01); *G01N 33/5041* (2013.01); *G01N 33/5058* (2013.01); *A61K 38/00* (2013.01); *A61N 2005/0661* (2013.01); *A61N 2005/0662* (2013.01)

(58) Field of Classification Search
None
See application file for complete search history.

(56) References Cited

U.S. PATENT DOCUMENTS

| 5,041,224 | A | 8/1991 | Ohyama et al. |
| 6,197,387 | B1 | 3/2001 | Feidler et al. |
| 7,824,869 | B2 | 11/2010 | Hegemann et al. |
| 7,939,220 | B2 | 5/2011 | Oesterhelt et al. |
| 8,202,699 | B2 | 6/2012 | Hegemann et al. |
| 8,401,609 | B2 | 3/2013 | Deisseroth et al. |
| 2007/0053996 | A1 | 3/2007 | Boyden et al. |
| 2007/0054319 | A1 | 3/2007 | Boyden et al. |
| 2007/0261127 | A1 | 11/2007 | Boyden et al. |
| 2009/0099038 | A1 | 4/2009 | Deisseroth et al. |
| 2010/0087006 | A1 | 4/2010 | Gressel et al. |
| 2010/0145418 | A1 | 6/2010 | Zhang et al. |
| 2010/0234273 | A1 | 9/2010 | Boyden et al. |
| 2011/0165681 | A1 | 7/2011 | Boyden et al. |
| 2012/0121542 | A1 | 5/2012 | Chuong et al. |
| 2012/0214188 | A1 | 8/2012 | Klapoetke et al. |
| 2015/0192567 | A1 | 7/2015 | Chuong et al. |

FOREIGN PATENT DOCUMENTS

| EP | 2112510 | * | 10/2009 |
| EP | 2112510 | A1 | 10/2009 |
| WO | 2007/024391 | * | 3/2007 |
| WO | 2007024391 | A3 | 3/2007 |
| WO | 2009/119782 | * | 10/2009 |
| WO | 2009119782 | A1 | 10/2009 |
| WO | 2010056970 | A2 | 5/2010 |
| WO | 2012061676 | A1 | 5/2012 |
| WO | 2012061744 | A2 | 5/2012 |

OTHER PUBLICATIONS

Baliga, N.S. et al., "Genome sequence of Haloarcula marismortui: A halophilic archaeon from the Dead Sea", Genome Research, 2004, vol. 14, pp. 2221-2234.
Boyden, E. et al, "Millisecond-timescale, genetically targeted optical control of neural activity", Nature Neuroscience, Sep. 2005, vol. 8, pp. 1263-1268.
Busskamp, V. et al., "Genetic Reactivation of Cone Photoreceptors Restores Visual Responses in Retinitis Pigmentosa", Science, Jul. 23, 2010, vol. 329, pp. 413-417.
Chow, B. et al., "High-performance genetically targetable optical neural silencing by light-driven proton pumps", Nature, Jan. 7, 2010, vol. 463, pp. 98-102.
Chow, B. et al., "Synthetic Physiology Strategies for Adapting Tools from Nature for Genetically Targeted Control of Fast Biological Processes", Methods in Enzymology, 2011, vol. 497, pp. 425-443.
Chuong, A. et al., "Development of next-generation optical neural silencers through directed combinatorial optimization", Neuroscience 2010 Annual Meeting, Nov. 13, 2010, Presentation Abstract, 2 pages.

(Continued)

*Primary Examiner* — Patricia Duffy
(74) *Attorney, Agent, or Firm* — Pierce Atwood LLP

(57) ABSTRACT

The invention, in some aspects relates to compositions and methods for altering cell activity and function and the introduction and use of light-activated ion channels.

25 Claims, 13 Drawing Sheets
Specification includes a Sequence Listing.

(56) References Cited

OTHER PUBLICATIONS

Chuong, A. et al., "Red-shifted optical neuronal silencing: optical hemoglobin transparency for long-distance optogenetic inhibition", Neuroscience 2010 Annual Meeting, Nov. 13, 2010, Poster Presentation, 1 page.
Dittgen, T. et al., "Lentivirus-based genetic manipulations of cortical neurons and their optical and electrophysiological monitoring in vivo", PNAS, Dec. 28, 2004, vol. 101, pp. 18206-18211.
Doroudchi, M. et al., "Virally delivered Channelrhodopsin-2 Safely and Effectively Restores Visual Function in Multiple Mouse Models of Blindness", Molecular Therapy, Jul. 2011, vol. 19, pp. 1220-1229.
Gradinaru, V. et al., "eNpHR: a Natronomonas halorhodopsin enhanced for optogenetic applications", Brain Cell Biology, 2008, vol. 36, pp. 129-139.
Gradinaru, V. et al., "Molecular and Cellular Approaches for Diversifying and Extending Optogenetics", Cell, Apr. 2, 2010, vol. 141, pp. 154-165.
Hackett, N. et al., "Structure-Function Studies on Bacteriorhodopsin", The Journal of Biological Chemistry, Jul. 5, 1987, vol. 262, pp. 9277-9284.
Han, X. & E. Boyden, "Multiple-Color Optical Activation, Silencing, and Desynchronization of Neural Activity, with Single-Spike Temporal Resolution", PloS one, Mar. 2007, Issue 3, pp. 1-12.
Han, X. et al., "A high-light sensitivity optical neural silencer: development and application to optogenetic control of non-human primate cortex", Frontiers in Systems Neuroscience, Apr. 13, 2011, vol. 5, pp. 1-8.
Han, X. et al., "Informational lesions: optical perturbation of spike timing and neural synchrony via microbial opsin gene fusions", Frontiers in Molecular Neuroscience, Aug. 27, 2009, vol. 2, pp. 1-9.
Ihara, K. et al., "*Haloarcula argentinensis* sp. nov. and *Haloarcula mukohataei* sp. nov., Two New Extremely Halophilic Archaea Collected in Argentina", International Journal of Systematic Bacteriology, Jan. 1997, vol. 47, pp. 73-77.
Ihara, K. et al., "Evolution of the Archaeal Rhodopsins: Evolution Rate Changes by Gene Duplication and Functional Differentiation", Journal of Molecular Biology, 1999, vol. 285, pp. 163-174.
Javor, B et al., "Box-Shaped Halophilic Bacteria", Journal of Bacteriology, Sep. 1982, vol. 151, pp. 1532-1542.
Klare, J. et al., "Microbial Rhodopsins: Scaffolds for Ion Pumps, Channels, and Sensors", Results and Problems in Cell Differentiation Journal Impact Factor & Information, Sep. 27, 2007, vol. 45, pp. 73-122.
Kitajima, T. et al. "Novel Bacterial Rhodopsins from Haloarcula vallismortis", Biochemical and Biophysical Research Communications, 1996, vol. 220, pp. 341-345.
Kleinlogel, S. et al., "Ultra-light sensitive and fast neuronal activation with the Ca(2+)-permeable channelrhodopsin CatCh", Nature Neuroscience, Apr. 2011, vol. 14, pp. 513-518.
Lin, J. et al., "Characterization of Engineered Channelrhodopsin Variants with Improved Properties and Kinetics", Biophysical Journal, Mar. 4, 2009, vol. 96, pp. 1803-1814.
Mogi, T. et al, "Structure-Function Studies on Bacteriorhodopsin", The Journal of Biological Chemistry, Aug. 25, 1989, vol. 264, pp. 14197-14201.
Nagel, G. et al., "Channelrhodopsin-1: A Light-Gated Proton Channel in Green Algae", Science, Jun. 28, 2002, vol. 296, pp. 2395-2398.
Nagel, G. et al., "Channelrhodopsin-2, a directly light-gated cation-selective membrane channel", PNAS, Nov. 25, 2003, vol. 100, pp. 13940-13945.
Otomo, J., "Anion selectivity and pumping mechanism of halorhodopsin", Biophysical Chemistry, 1995, vol. 56, pp. 137-141.
Otomo, J. et al. "Bacterial rhodopsins of newly isolated halobacteria", Journal of General Microbiology, Jan. 6, 1992, vol. 138, pp. 1027-1037.
Otomo, J. & T. Muramatsu, "Over-expression of a new photo-active halorhodopsin in Halobacterium salinarium", Biochimica et Biophysica Acta, Aug. 1995, vol. 1240, pp. 248-256.
Rudiger, M. & D. Oesterhelt, "Specific arginine and threonine residues control anion binding and transport in the light-driven chloride pumo halorhodopsin", The EMBO Journal, 1997, vol. 16, pp. 3813-3821.
Tang et al., "Faithful Expression of Multiple Proteins via 2A-Peptide Self-Processing: A Versatile and Reliable Method for Manipulating Brain Circuits", The Journal of Neuroscience, Jul. 8, 2009, vol. 29, pp. 8621-8629.
Wang, H. et al., "High-speed mapping of synaptic connectivity using photostimulation in Channelrhodopsin-2 transgenic mice", PNAS, May 8, 2007, vol. 104, pp. 8143-8148. Epub May 1, 2007.
Yizhar, O. et al., "Neocortical excitation/inhibition balance in information processing and social dysfunction", Nature, Sep. 8, 2011, vol. 477, pp. 1-8.
Zhang, F. et al., "Multimodal fast optical interrogation of neural circuitry" Nature, 2007, pp. 633-639, vol. 446.
Zhang, F. et al., "Red-shifted optogenetic excitation: a tool for fast neural control derived from Volvox carteri", Nature Neuroscience, 2008, vol. 11, pp. 631-633.
Feldbauera, K. et al., "Channelrhodopsin-2 is a leaky proton pump", PNAS, Jul. 28, 2009, vol. 106, pp. 12317-12322.
Mukohata, Y. et al., "Halobacterial Rhodopsins", Journal of Biochemistry, 1999, vol. 125, pp. 649-657.
International Search Report International Patent Application No. PCT/US2012/064665, dated Apr. 4, 2013, 5 pages.
International Publication for International Patent Application No. PCT/US2012/064665, WO2013071231, published May 16, 2013, 83 pages.
International Preliminary Report on Patentability and Written Opinion of the International Searching Authority dated May 22, 2014 for International Patent Application No. PCT/US2012/064665, 9 pages.
EP Office Action dated Jul. 29, 2015 for EP Patent Application No. 12808926.5, issued by the European Patent Office, 6 pages.
Radu, I., et al., "Conformational changes of channelrhodopsin-2", J Am Chem Soc., Jun. 3, 2009, vol. 131, 1 page. Abstract only.
Sugiyama, Y., et al., "Photocurrent attenuation by a single polar-to-nonpolar point mutation of channelrhodopsin-2", Photochem Photobiol Sci., Mar. 2009, vol. 8, 1 page. Abstract only.
Nack, M., "The DC gate in Channelrhodopsin-2: crucial hydrogen bonding interaction between C128 and D156", Photochem Photobiol Sci., Feb. 2010, vol. 9, 1 page. Abstract only.
Berndt et al., "High-efficiency channelrhodopsins for fast neuronal stimulation at low light levels." PNAS, May 3, 2011, vol. 108, No. 18, pp. 7595-7600, plus two supplemental information pages, 7 pages total.
Lin, John Y. "A user's guide to channelrhodopsin variants: features, limitations and future developments." Exp. Physiol (2011) 96. 1, pp. 19-25.

* cited by examiner

SEQUENCE LISTING

```
<160> NUMBER OF SEQ ID NOS: 25

<210> SEQ ID NO 1
<211> LENGTH: 669
<212> TYPE: PRT
<213> ORGANISM: Chlamydomonas noctigama

<400> SEQUENCE: 1

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
```

```
                210               215               220
Ile Tyr Gly Gly Tyr Met Tyr Phe Gln Ala Ala Lys Cys Tyr Val Glu
225                     230                 235                 240

Ala Asn His Ser Val Pro Lys Gly His Cys Arg Met Val Val Lys Leu
                        245                 250                 255

Met Ala Tyr Ala Tyr Phe Ala Ser Trp Gly Ser Tyr Pro Ile Leu Trp
                260                 265                 270

Ala Val Gly Pro Glu Gly Leu Leu Lys Leu Ser Pro Tyr Ala Asn Ser
            275                 280                 285

Ile Gly His Ser Ile Cys Asp Ile Ile Ala Lys Glu Phe Trp Thr Phe
        290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Asp Glu Asp Thr Val Thr His
                    340                 345                 350

Pro Thr Ser Asn Leu Ala Asn Arg Asn Ser Phe Val Ile Met Ala Glu
                355                 360                 365

Arg Met Arg Ala Arg Gly Ile Asp Val Arg Ala Ser Leu Asp Arg Asn
370                 375                 380

Gly Pro Met Ile Glu Ser Gly Arg Val Ile Leu Ala Asp Thr Asp Ile
385                 390                 395                 400

Phe Val Thr Glu Met Phe Lys Ala Gln Phe Ala Gln Leu Pro Ala Ala
                405                 410                 415

Ile Glu Leu Ile Pro Ala Leu Gly Ala Asp Asn Ala Leu Gln Leu Val
                420                 425                 430

Gln Gln Ala Ser Val Leu Gly Gly Cys Asp Phe Val Met Val His Pro
            435                 440                 445

Gln Phe Leu Lys Asp Asn Ser Pro Ser Gly Leu Val Ala Arg Leu Arg
        450                 455                 460

Met Met Gly Gln Arg Val Val Ala Phe Gly Pro Ala Asn Leu Arg Glu
465                 470                 475                 480

Leu Ile Glu Ser Cys Asp Val Asp Ala Trp Ile Glu Ala Pro Pro Ile
                485                 490                 495

Asn Leu Tyr Gln Leu Arg Gln Val Val Ala Gln Met Gln Leu Met Arg
                500                 505                 510

Arg Gln Ala Ala Met Met Gly Gly Met Gly Gly Gly Met Lys Gly Gly
            515                 520                 525

Met Ser Gly Met Gly Met Gly Met His Ala Gly Ser Met Trp Lys Gln
        530                 535                 540

Gln Gln Met Met Met Gln Asp Gly Ser Ala Met Met Met Pro Ala
545                 550                 555                 560

Met Gln Gly Gly Ala Ala Ser Met Arg Gly Ser Gly Leu Ile Ser Ala
                565                 570                 575

Gln Pro Gly Arg Gln Ala Ser Leu Gly Gly Pro Gln Ser Val Met Met
                580                 585                 590

Gly Ser Ala Met Val Gly Ser Asn Pro Leu Phe Gly Thr Ala Pro Ser
            595                 600                 605

Pro Leu Gly Ser Ala Val Gly Ala Glu Ala Met Gly His Asn Leu Tyr
        610                 615                 620

Gly Asn Gln Ala Ala Ala Gly Gly Ile Pro Ala Ala Ser Ala Ala Ala
625                 630                 635                 640
```

Asp Gly Thr Asp Val Glu Met Met Gln Gln Leu Met Ser Glu Ile Asp
            645                 650                 655

Arg Leu Lys Gly Glu Leu Gly Glu Gln Asp Met Pro Arg
        660                 665

<210> SEQ ID NO 2
<211> LENGTH: 350
<212> TYPE: PRT
<213> ORGANISM: Chlamydomonas noctigama

<400> SEQUENCE: 2

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Glu Asp Glu Asp Thr Val

<210> SEQ ID NO 3
<211> LENGTH: 1050
<212> TYPE: DNA
<213> ORGANISM: Artificial Sequence
<220> FEATURE:
<223> OTHER INFORMATION: Synthetic Oligonucleotide, Mammalian-condon optimized DNA

<400> SEQUENCE: 3

```
atggctgagc tgatcagcag cgccaccaga tctctgtttg ccgccggagg catcaaccct    60
tggcctaacc cctaccacca cgaggacatg ggctgtggag aatgacacc tacaggcgag   120
tgcttcagca ccgagtggtg gtgtgaccct tcttacggac tgagcgacgc cggatacgga   180
tattgcttcg tggaggccac aggcggctac ctggtcgtgg gagtggagaa gaagcaggct   240
tggctgcaca gcagaggcac accaggagaa aagatcggcg cccaggtctg ccagtggatt   300
gctttcagca tcgccatcgc cctgctgaca ttctacggct tcagcgcctg gaaggccact   360
tgcggttggg aggaggtcta cgtctgtgtt gtcgaggtgc tgttcgtgac cctggagatc   420
ttcaaggagt tcagcagccc cgccacagtg tacctgtcta ccggcaacca cgcctattgc   480
ctgcgctact tcgagtggct gctgtcttgc cccgtgatcc tgatcaagct gagcaacctg   540
agcggcctga gaacgactac agcaagcgg accatgggcc tgatcgtgtc ttgcgtggga   600
atgatcgtgt tcggcatggc cgcaggactg gctaccgatt ggctcaagtg ctgctgtat   660
atcgtgtctt gcatctacgg cggctacatg tacttccagg ccgccaagtg ctacgtggaa   720
gccaaccaca gcgtgcctaa aggccattgc cgcatggtcg tgaagctgat ggcctacgct   780
tacttcgcct cttggggcag ctacccaatc ctctgggcag tgggaccaga aggactgctg   840
aagctgagcc cttacgccaa cagcatcggc cacagcatct gcgacatcat cgccaaggag   900
tttggaccct cctggcccca ccctgaggga atcaagatcc acgagcacat cctgatccac   960
ggcgacatcc ggaagaccac caagatggag atcgaggcg aggaggtgga agtggaagag  1020
ttcgtggagg aggaggacga ggacacagtg                                    1050
```

<210> SEQ ID NO 4
<211> LENGTH: 235
<212> TYPE: PRT
<213> ORGANISM: Chlamydomonas noctigama

<400> SEQUENCE: 4

Gly Thr Pro Gly Glu Lys Ile Gly Ala Gln Val Cys Gln Trp Ile Ala
1               5                   10                  15

Phe Ser Ile Ala Ile Ala Leu Leu Thr Phe Tyr Gly Phe Ser Ala Trp
            20                  25                  30

Lys Ala Thr Cys Gly Trp Glu Glu Val Tyr Val Cys Val Glu Val
        35                  40                  45

Leu Phe Val Thr Leu Glu Ile Phe Lys Glu Phe Ser Ser Pro Ala Thr
    50                  55                  60

Val Tyr Leu Ser Thr Gly Asn His Ala Tyr Cys Leu Arg Tyr Phe Glu
65                  70                  75                  80

Trp Leu Leu Ser Cys Pro Val Ile Leu Ile Lys Leu Ser Asn Leu Ser
                85                  90                  95

Gly Leu Lys Asn Asp Tyr Ser Lys Arg Thr Met Gly Leu Ile Val Ser
            100                 105                 110

Cys Val Gly Met Ile Val Phe Gly Met Ala Ala Gly Leu Ala Thr Asp

```
            115                 120                 125
Trp Leu Lys Trp Leu Leu Tyr Ile Val Ser Cys Ile Tyr Gly Gly Tyr
        130                 135                 140

Met Tyr Phe Gln Ala Ala Lys Cys Tyr Val Glu Ala Asn His Ser Val
145                 150                 155                 160

Pro Lys Gly His Cys Arg Met Val Val Lys Leu Met Ala Tyr Ala Tyr
                165                 170                 175

Phe Ala Ser Trp Gly Ser Tyr Pro Ile Leu Trp Ala Val Gly Pro Glu
            180                 185                 190

Gly Leu Leu Lys Leu Ser Pro Tyr Ala Asn Ser Ile Gly His Ser Ile
        195                 200                 205

Cys Asp Ile Ile Ala Lys Glu Phe Trp Thr Phe Leu Ala His His Leu
    210                 215                 220

Arg Ile Lys Ile His Glu His Ile Leu Ile His
225                 230                 235

<210> SEQ ID NO 5
<211> LENGTH: 350
<212> TYPE: PRT
<213> ORGANISM: Artificial Sequence
<220> FEATURE:
<223> OTHER INFORMATION: Synthetic polypeptide

<400> SEQUENCE: 5

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Arg
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
```

```
            245                 250                 255
Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
                325                 330                 335

Glu Val Glu Glu Phe Val Glu Glu Asp Glu Asp Thr Val
            340                 345                 350
```

<210> SEQ ID NO 6
<211> LENGTH: 421
<212> TYPE: PRT
<213> ORGANISM: Stigeoclonium helveticum

<400> SEQUENCE: 6

```
Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
            20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270
```

```
Ser Lys Asn Thr Trp Gly Phe Leu Gly His His Leu Arg Val Lys Ile
            275                 280                 285

His Glu His Ile Leu Ile His Gly Asp Ile Arg Lys Thr Thr Thr Ile
            290                 295                 300

Asn Val Ala Gly Glu Asn Met Glu Ile Glu Thr Phe Val Asp Glu Glu
305                 310                 315                 320

Glu Glu Gly Gly Val Asn His Gly Thr Ala Asp Leu Ala His Arg Ala
                325                 330                 335

Ser Phe Gln Lys Met Gly Asp Arg Leu Arg Ala Gln Gly Val Thr Val
            340                 345                 350

Arg Ala Ser Leu Asp Ala His Glu Val Pro Pro Ala Asp Glu Glu Asn
            355                 360                 365

Lys Phe Ala Gln Lys Ser Ala Ala Ala Asn Met Pro Ala Tyr Asn Pro
            370                 375                 380

Gly Lys Val Ile Leu Ile Val Pro Asp Met Ser Met Val Asp Tyr Phe
385                 390                 395                 400

Arg Asp Gln Phe Glu Gln Leu Pro Thr Arg Met Glu Leu Leu Pro Ala
                405                 410                 415

Leu Gly Met Asp Thr
            420

<210> SEQ ID NO 7
<211> LENGTH: 325
<212> TYPE: PRT
<213> ORGANISM: Stigeoclonium helveticum

<400> SEQUENCE: 7

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65              70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
            115                 120                 125

Asn Gly Gly Ala Val Ile Trp Leu Arg Tyr Ser Met Trp Leu Leu Thr
            130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
            195                 200                 205

Ile Ala Lys Val Tyr Ile Glu Ser Tyr His Thr Leu Pro Lys Gly Val
            210                 215                 220
```

```
Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
            245                 250                 255

Ile Thr Pro Tyr Thr Ser Gly Ile Gly His Leu Ile Leu Asp Leu Ile
        260                 265                 270

Ser Lys Asn Thr Trp Gly Phe Leu Gly His His Leu Arg Val Lys Ile
    275                 280                 285

His Glu His Ile Leu Ile His Gly Asp Ile Arg Lys Thr Thr Thr Ile
290                 295                 300

Asn Val Ala Gly Glu Asn Met Glu Ile Glu Thr Phe Val Asp Glu Glu
305                 310                 315                 320

Glu Glu Gly Gly Val
            325

<210> SEQ ID NO 8
<211> LENGTH: 975
<212> TYPE: DNA
<213> ORGANISM: Artificial Sequence
<220> FEATURE:
<223> OTHER INFORMATION: Synthetic Oligonucleotide, Mammalian-condon
      optimized DNA

<400> SEQUENCE: 8
atggaaacag ccgccacaat gacccacgcc tttatctcag ccgtgcctag cgccgaagcc      60
acaattagag gcctgctgag cgccgcagca gtggtgacac cagcagcaga cgctcacgga    120
gaaacctcta cgccacaac agccggagcc gatcacggtt gcttccccca catcaaccac     180
ggaaccgagc tgcagcacaa gatcgcagtg ggactccagt ggttcaccgt gatcgtggct    240
atcgtgcagc tcatcttcta cggttggcac agcttcaagg ccacaaccgg ctgggaggag    300
gtctacgtct gcgtgatcga gctcgtcaag tgcttcatcg agctgttcca cgaggtcgac    360
agcccagcca cagtgtacca gaccaacgga ggagccgtga tttggctgcg gtacagcatg    420
tggctcctga cttgccccgt gatcctgatc cacctgagca acctgaccgg actgcacgaa    480
gagtacagca agcggaccat gaccatcctg gtgaccgaca tcggcaacat cgtgtggggg    540
atcacagccg cctttacaaa gggccccctg aagatcctgt tcttcatgat cggcctgttc    600 tacgcgtga cttgcttctt ccagatcgcc aaggtgtata tcgagagcta ccacaccctg    660
cccaaaggcg tctgccggaa gatttgcaag atcatggcct acgtcttctt ctgctcttgg    720
ctgatgttcc ccgtgatgtt catcgccgga cacgagggac tgggcctgat cacaccttac    780
accagcggaa tcggccacct gatcctggat ctgatcagca gaacacttgg ggcttcctg    840 ggccaccacc tgagagtgaa gatccacgag cacatcctga tccacggcga catccggaag    900
acaaccacca tcaacgtggc cggcgagaac atggagatcg agaccttcgt cgacgaggag    960
gaggagggag gagtg                                                     975

<210> SEQ ID NO 9
<211> LENGTH: 235
<212> TYPE: PRT
<213> ORGANISM: Stigeoclonium helveticum

<400> SEQUENCE: 9

Gly Thr Glu Leu Gln His Lys Ile Ala Val Gly Leu Gln Trp Phe Thr
1               5                   10                  15

Val Ile Val Ala Ile Val Gln Leu Ile Phe Tyr Gly Trp His Ser Phe
```

```
                20              25              30
Lys Ala Thr Thr Gly Trp Glu Glu Val Tyr Val Cys Val Ile Glu Leu
            35              40              45
Val Lys Cys Phe Ile Glu Leu Phe His Glu Val Asp Ser Pro Ala Thr
 50              55              60
Val Tyr Gln Thr Asn Gly Gly Ala Val Ile Trp Leu Arg Tyr Ser Met
 65              70              75              80
Trp Leu Leu Thr Cys Pro Val Ile Leu Ile His Leu Ser Asn Leu Thr
                85              90              95
Gly Leu His Glu Glu Tyr Ser Lys Arg Thr Met Thr Ile Leu Val Thr
            100             105             110
Asp Ile Gly Asn Ile Val Trp Gly Ile Thr Ala Ala Phe Thr Lys Gly
            115             120             125
Pro Leu Lys Ile Leu Phe Phe Met Ile Gly Leu Phe Tyr Gly Val Thr
            130             135             140
Cys Phe Phe Gln Ile Ala Lys Val Tyr Ile Glu Ser Tyr His Thr Leu
145             150             155             160
Pro Lys Gly Val Cys Arg Lys Ile Cys Lys Ile Met Ala Tyr Val Phe
                165             170             175
Phe Cys Ser Trp Leu Met Phe Pro Val Met Phe Ile Ala Gly His Glu
                180             185             190
Gly Leu Gly Leu Ile Thr Pro Tyr Thr Ser Gly Ile Gly His Leu Ile
            195             200             205
Leu Asp Leu Ile Ser Lys Asn Thr Trp Gly Phe Leu Gly His His Leu
    210             215             220
Arg Val Lys Ile His Glu His Ile Leu Ile His
225             230             235

<210> SEQ ID NO 10
<211> LENGTH: 457
<212> TYPE: PRT
<213> ORGANISM: Chloromonas subdivisa

<400> SEQUENCE: 10

Met Ser Arg Leu Val Ala Ala Ser Trp Leu Leu Ala Leu Leu Leu Cys
 1               5              10              15
Gly Ile Thr Ser Thr Thr Thr Ala Ser Ser Ala Pro Ala Ala Ser Ser
                20              25              30
Thr Asp Gly Thr Ala Ala Ala Val Ser His Tyr Ala Met Asn Gly
            35              40              45
Phe Asp Glu Leu Ala Lys Gly Ala Val Val Pro Glu Asp His Phe Val
 50              55              60
Cys Gly Pro Ala Asp Lys Cys Tyr Cys Ser Ala Trp Leu His Ser His
 65              70              75              80
Gly Ser Lys Glu Glu Lys Thr Ala Phe Thr Val Met Gln Trp Ile Val
            85              90              95
Phe Ala Val Cys Ile Ile Ser Leu Leu Phe Tyr Ala Tyr Gln Thr Trp
            100             105             110
Arg Ala Thr Cys Gly Trp Glu Glu Val Tyr Val Thr Ile Ile Glu Leu
            115             120             125
Val His Val Cys Phe Gly Leu Trp His Glu Val Asp Ser Pro Cys Thr
            130             135             140
Leu Tyr Leu Ser Thr Gly Asn Met Val Leu Trp Leu Arg Tyr Ala Glu
145             150             155             160
```

-continued

```
Trp Leu Leu Thr Cys Pro Val Ile Leu Ile His Leu Ser Asn Leu Thr
            165                 170                 175

Gly Met Lys Asn Asp Tyr Asn Lys Arg Thr Met Ala Leu Leu Val Ser
        180                 185                 190

Asp Val Gly Cys Ile Val Trp Gly Thr Thr Ala Ala Leu Ser Thr Asp
    195                 200                 205

Phe Val Lys Ile Ile Phe Phe Phe Leu Gly Leu Leu Tyr Gly Phe Tyr
210                 215                 220

Thr Phe Tyr Ala Ala Ala Lys Ile Tyr Ile Glu Ala Tyr His Thr Val
225                 230                 235                 240

Pro Lys Gly Ile Cys Arg Gln Leu Val Arg Leu Gln Ala Tyr Asp Phe
                245                 250                 255

Phe Phe Thr Trp Ser Met Phe Pro Ile Leu Phe Met Val Gly Pro Glu
            260                 265                 270

Gly Phe Gly Lys Ile Thr Ala Tyr Ser Ser Gly Ile Ala His Glu Val
        275                 280                 285

Cys Asp Leu Leu Ser Lys Asn Leu Trp Gly Leu Met Gly His Phe Ile
    290                 295                 300

Arg Val Lys Ile His Glu His Ile Leu Val His Gly Asn Ile Thr Lys
305                 310                 315                 320

Lys Thr Lys Val Asn Val Ala Gly Asp Met Val Glu Leu Asp Thr Tyr
                325                 330                 335

Val Asp Gln Asp Glu Glu His Asp Glu Gly Thr Ile Asp Arg Gly Thr
            340                 345                 350

Gln Glu Leu Ala Asn Arg His Ser Phe Val Val Met Arg Glu Asn Met
        355                 360                 365

Arg Ala Lys Gly Val Asp Val Arg Ala Ser Leu Gly Asp Ile Asp Gly
    370                 375                 380

Thr Glu Met Thr Lys Ala Gly Asn Met Asn Gly Thr Leu Glu Pro Gly
385                 390                 395                 400

Arg Ile Ile Leu Cys Val Pro Asp Met Ser Leu Val Asp Phe Phe Arg
                405                 410                 415

Glu Gln Phe Ser Gln Met Pro Val Pro Phe Glu Val Val Pro Ala Leu
            420                 425                 430

Gly Pro Glu Val Ala Leu Gln Leu Val Gln Gln Ala Leu Ser Ile Gly
        435                 440                 445

Gly Ala Asn Tyr Ile Asp Tyr Val Met
    450                 455

<210> SEQ ID NO 11
<211> LENGTH: 346
<212> TYPE: PRT
<213> ORGANISM: Chloromonas subdivisa

<400> SEQUENCE: 11

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser His
65                  70                  75                  80
```

Gly Ser Lys Glu Glu Lys Thr Ala Phe Thr Val Met Gln Trp Ile Val
            85                  90                  95

Phe Ala Val Cys Ile Ile Ser Leu Leu Phe Tyr Ala Tyr Gln Thr Trp
        100                 105                 110

Arg Ala Thr Cys Gly Trp Glu Glu Val Tyr Val Thr Ile Ile Glu Leu
        115                 120                 125

Val His Val Cys Phe Gly Leu Trp His Glu Val Asp Ser Pro Cys Thr
    130                 135                 140

Leu Tyr Leu Ser Thr Gly Asn Met Val Leu Trp Leu Arg Tyr Ala Glu
145                 150                 155                 160

Trp Leu Leu Thr Cys Pro Val Ile Leu Ile His Leu Ser Asn Leu Thr
                165                 170                 175

Gly Met Lys Asn Asp Tyr Asn Lys Arg Thr Met Ala Leu Leu Val Ser
            180                 185                 190

Asp Val Gly Cys Ile Val Trp Gly Thr Thr Ala Ala Leu Ser Thr Asp
        195                 200                 205

Phe Val Lys Ile Ile Phe Phe Phe Leu Gly Leu Leu Tyr Gly Phe Tyr
    210                 215                 220

Thr Phe Tyr Ala Ala Ala Lys Ile Tyr Ile Glu Ala Tyr His Thr Val
225                 230                 235                 240

Pro Lys Gly Ile Cys Arg Gln Leu Val Arg Leu Gln Ala Tyr Asp Phe
                245                 250                 255

Phe Phe Thr Trp Ser Met Phe Pro Ile Leu Phe Met Val Gly Pro Glu
            260                 265                 270

Gly Phe Gly Lys Ile Thr Ala Tyr Ser Ser Gly Ile Ala His Glu Val
        275                 280                 285

Cys Asp Leu Leu Ser Lys Asn Leu Trp Gly Leu Met Gly His Phe Ile
    290                 295                 300

Arg Val Lys Ile His Glu His Ile Leu Val His Gly Asn Ile Thr Lys
305                 310                 315                 320

Lys Thr Lys Val Asn Val Ala Gly Asp Met Val Glu Leu Asp Thr Tyr
                325                 330                 335

Val Asp Gln Asp Glu Glu His Asp Glu Gly
            340                 345

<210> SEQ ID NO 12
<211> LENGTH: 1038
<212> TYPE: DNA
<213> ORGANISM: Artificial Sequence
<220> FEATURE:
<223> OTHER INFORMATION: Synthetic oligonucleotide, Mammalian-codon
      optimized DNA

<400> SEQUENCE: 12
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt ggtgccagaa     180 gaccactttg tctgcggacc agccgacaag tgctattgct ccgcttggct gcacagccac     240
ggaagcaagg aggagaagac cgccttcacc gtcatgcagt ggatcgtgtt cgccgtctgc     300
atcatcagcc tgctgttcta cgcctaccag acttggaggg ctacttgcgg ttgggaggag     360
gtgtacgtga ccatcatcga gctggtccac gtctgcttcg gactctggca cgaggtcgat     420
agcccttgta ccctgtacct gagcacaggc aacatggtcc tctggctgag atacgccgag     480

```
tggctgctga cttgccccgt gatcctgatc cacctgagca acctgaccgg catgaagaac      540
gactacaaca agcggaccat ggccctgctg gtgtcagacg tgggctgtat cgtgtgggga      600
acaacagccg ccctgagcac cgatttcgtg aagatcatct tcttcttcct gggcctgctg      660
tacggcttct acaccttcta cgccgccgcc aagatctaca tcgaggccta ccacaccgtg      720
cccaagggca tttgtagaca gctcgtgcgg ctgcaggcct acgacttctt cttcacttgg      780
agcatgttcc ccatcctgtt catggtcggc cagagggat cggcaagat caccgcctac       840 agcagcggaa tcgcccacga agtgtgcgat ctgctgagca agaacctctg gggcctgatg      900
ggccacttca tccgcgtgaa gatccacgag cacatcctgg tgcacggcaa catcaccaag      960
aagaccaagg tcaacgtggc cggcgacatg gtggaactgg acacctacgt ggaccaggac     1020
gaggaacacg acgaggga                                                   1038
```

<210> SEQ ID NO 13
<211> LENGTH: 235
<212> TYPE: PRT
<213> ORGANISM: Chloromonas subdivisa

<400> SEQUENCE: 13

```
Gly Ser Lys Glu Glu Lys Thr Ala Phe Thr Val Met Gln Trp Ile Val
1               5                   10                  15

Phe Ala Val Cys Ile Ile Ser Leu Leu Phe Tyr Ala Tyr Gln Thr Trp
            20                  25                  30

Arg Ala Thr Cys Gly Trp Glu Glu Val Tyr Val Thr Ile Ile Glu Leu
        35                  40                  45

Val His Val Cys Phe Gly Leu Trp His Glu Val Asp Ser Pro Cys Thr
    50                  55                  60

Leu Tyr Leu Ser Thr Gly Asn Met Val Leu Trp Leu Arg Tyr Ala Glu
65                  70                  75                  80

Trp Leu Leu Thr Cys Pro Val Ile Leu Ile His Leu Ser Asn Leu Thr
                85                  90                  95

Gly Met Lys Asn Asp Tyr Asn Lys Arg Thr Met Ala Leu Leu Val Ser
            100                 105                 110

Asp Val Gly Cys Ile Val Trp Gly Thr Thr Ala Ala Leu Ser Thr Asp
        115                 120                 125

Phe Val Lys Ile Ile Phe Phe Phe Leu Gly Leu Leu Tyr Gly Phe Tyr
    130                 135                 140

Thr Phe Tyr Ala Ala Ala Lys Ile Tyr Ile Glu Ala Tyr His Thr Val
145                 150                 155                 160

Pro Lys Gly Ile Cys Arg Gln Leu Val Arg Leu Gln Ala Tyr Asp Phe
                165                 170                 175

Phe Phe Thr Trp Ser Met Phe Pro Ile Leu Phe Met Val Gly Pro Glu
            180                 185                 190

Gly Phe Gly Lys Ile Thr Ala Tyr Ser Ser Gly Ile Ala His Glu Val
        195                 200                 205

Cys Asp Leu Leu Ser Lys Asn Leu Trp Gly Leu Met Gly His Phe Ile
    210                 215                 220

Arg Val Lys Ile His Glu His Ile Leu Val His
225                 230                 235
```

<210> SEQ ID NO 14
<211> LENGTH: 310
<212> TYPE: PRT
<213> ORGANISM: Neochlorosarcina

<400> SEQUENCE: 14

Met Ala Asp Phe Val Trp Gln Gly Ala Gly Asn Gly Gly Pro Ser Ala
1               5                   10                  15

Met Val Ser His Tyr Pro Asn Gly Ser Val Leu Leu Glu Ser Ser Gly
            20                  25                  30

Ser Cys Tyr Cys Glu Asp Trp Tyr Thr Ser Arg Gly Asn His Val Glu
        35                  40                  45

His Ser Leu Ser Asn Ala Cys Asp Trp Phe Ala Phe Ala Ile Ser Val
    50                  55                  60

Ile Phe Leu Val Tyr Tyr Ala Trp Ala Ala Phe Asn Ser Ser Val Gly
65                  70                  75                  80

Trp Glu Glu Ile Tyr Val Cys Thr Val Glu Leu Ile Lys Val Ser Ile
                85                  90                  95

Asp Gln Phe Leu Ser Ser Asn Ser Pro Cys Thr Leu Tyr Leu Ser Thr
            100                 105                 110

Gly Asn Arg Val Leu Trp Ile Arg Tyr Gly Glu Trp Leu Leu Thr Cys
        115                 120                 125

Pro Val Ile Leu Ile His Leu Ser Asn Val Thr Gly Leu Lys Asp Asn
    130                 135                 140

Tyr Ser Lys Arg Thr Met Ala Leu Leu Val Ser Asp Ile Gly Thr Ile
145                 150                 155                 160

Val Phe Gly Val Thr Ser Ala Met Cys Thr Gly Tyr Pro Lys Val Ile
                165                 170                 175

Phe Phe Ile Leu Gly Cys Cys Tyr Gly Ala Asn Thr Phe Phe Asn Ala
            180                 185                 190

Ala Lys Val Tyr Leu Glu Ala His His Thr Leu Pro Lys Gly Ser Cys
        195                 200                 205

Arg Thr Leu Ile Arg Leu Met Ala Tyr Thr Tyr Ala Ser Trp Gly
    210                 215                 220

Met Phe Pro Ile Leu Phe Val Leu Gly Pro Glu Ser Phe Gly His Met
225                 230                 235                 240

Asn Met Tyr Gln Ser Asn Ile Ala His Thr Val Ile Asp Leu Met Ser
                245                 250                 255

Lys Asn Ile Trp Gly Met Leu Gly His Phe Leu Arg His Lys Ile Arg
            260                 265                 270

Glu His Ile Leu Ile His Gly Asp Leu Arg Thr Thr Thr Thr Val Asn
        275                 280                 285

Val Ala Gly Glu Glu Met Gln Val Glu Thr Met Val Ala Ala Glu Asp
    290                 295                 300

Ala Asp Glu Thr Thr Val
305             310

<210> SEQ ID NO 15
<211> LENGTH: 930
<212> TYPE: DNA
<213> ORGANISM: Artificial Sequence
<220> FEATURE:
<223> OTHER INFORMATION: Synthetic oligonucletide; Mammalian-condon
      optimized DNA

<400> SEQUENCE: 15
atggccgact tcgtgtggca gggagctgga aacggaggac caagcgccat ggtgtcccac    60
taccccaatg gcagcgtgct gctggagagc tccggcagct gctactgtga agactggtat   120
acttctcggg gcaaccacgt ggagcattct ctgagtaatg cttgcgattg gttcgccttt   180

```
gctatcagcg tgatttttcct ggtgtactat gcctgggccg cttttaactc tagtgtgggc    240
tgggaggaaa tctacgtgtg caccgtggag ctgatcaagg tgagcattga tcagttcctg    300
agctccaact ctccttgtac cctgtacctg agtacaggga taggtgtgct gtggatcaga    360
tatggcgaat ggctgctgac ttgtccagtg atcctgattc acctgtccaa cgtgacaggg    420
ctgaaggaca attactctaa cgcactatg gctctgctgg tgagtgatat cgggaccatc    480
gtgttcggcg tgacttctgc catgtgcacc ggataccca aagtgatctt ctttattctg     540
ggctgctgtt atggagctaa cacattcttt aatgccgcta aggtgtacct ggaggcccac    600
catacactgc ctaaaggctc ttgtaggact ctgatcagac tgatggccta tacctactat    660
gctagttggg gaatgttccc cattctgttt gtgctgggac ctgagagctt cggccacatg    720
aacatgtacc agtccaatat cgcccatacc gtgattgacc tgatgtccaa gaacatctgg    780
ggaatgctgg ggcactttct gcggcataaa attcgcgagc acatcctgat tcatggagat    840
ctgcggacca caactaccgt gaatgtggct ggggaggaaa tgcaggtgga acaatggtg    900
gccgctgagg acgccgatga acaactgtg                                      930
```

<210> SEQ ID NO 16
<211> LENGTH: 304
<212> TYPE: PRT
<213> ORGANISM: Heterochlamydomonas inaequalis

<400> SEQUENCE: 16

```
Met Gly Gly Ile Gly Gly Gly Ile Gln Pro Arg Asp Tyr Ser Tyr
1               5                   10                  15

Gly Ala Asn Gly Thr Val Cys Val Asn Pro Asp Val Cys Phe Cys Leu
                20                  25                  30

Asp Trp Gln Gln Pro Phe Gly Ser Asn Met Glu Asn Asn Val Ser Gln
            35                  40                  45

Gly Phe Gln Leu Phe Thr Ile Ala Leu Ser Ala Cys Ile Leu Met Phe
        50                  55                  60

Tyr Ala Tyr Glu Trp Tyr Lys Ala Thr Cys Gly Trp Glu Glu Ile Tyr
65                  70                  75                  80

Val Cys Val Val Glu Met Ser Lys Ile Cys Ile Glu Leu Val His Glu
                85                  90                  95

Tyr Asp Thr Pro Phe Cys Leu Tyr Leu Ala Thr Gly Ser Arg Val Leu
            100                 105                 110

Trp Leu Arg Tyr Ala Glu Trp Leu Met Thr Cys Pro Val Ile Leu Ile
        115                 120                 125

His Leu Ser Asn Ile Thr Gly Leu Gly Thr Asp Tyr Asn Lys Arg Thr
    130                 135                 140

Met Val Leu Leu Met Ser Asp Ile Gly Cys Ile Val Phe Gly Ala Thr
145                 150                 155                 160

Ala Ala Phe Ala Asn Glu Gly Tyr Val Lys Cys Ala Cys Phe Leu Leu
                165                 170                 175

Gly Met Ala Trp Gly Met Asn Thr Phe Tyr Asn Ala Ala Lys Val Tyr
            180                 185                 190

Tyr Glu Ser Tyr Val Leu Val Pro Ser Gly Ile Cys Lys Leu Leu Val
        195                 200                 205

Ala Val Met Ala Gly Leu Tyr Tyr Val Ser Trp Ser Leu Phe Pro Ile
    210                 215                 220

Leu Phe Ala Ile Gly Pro Glu Gly Phe Gly Val Ile Ser Leu Gln Ala
225                 230                 235                 240
```

```
Ser Thr Ile Gly His Thr Ile Ala Asp Val Leu Ser Lys Asn Met Trp
                245                 250                 255
Gly Leu Met Gly His Phe Leu Arg Val Gln Ile Tyr Lys His Ile Leu
            260                 265                 270
Leu His Gly Asn Ile Arg Lys Pro Ile Lys Leu His Met Leu Gly Glu
        275                 280                 285
Glu Val Glu Val Met Ala Leu Val Ser Glu Glu Gly Glu Asp Thr Val
    290                 295                 300
```

<210> SEQ ID NO 17
<211> LENGTH: 912
<212> TYPE: DNA
<213> ORGANISM: Artificial Sequence
<220> FEATURE:
<223> OTHER INFORMATION: Synthetic Oligonucleotide; Mammalian-condon optimized DNA

<400> SEQUENCE: 17

```
atgggaggaa ttggcggagg cggcattcag cctagagact acagctacgg cgccaacgga      60
acagtctgcg tgaaccccga cgtctgcttc tgtctggatt ggcagcagcc cttcggctct     120
aacatggaga caacgtgtc ccagggcttc agctgtttta ccatcgccct gagcgcctgc     180
atcctgatgt tctacgccta cgagtggtac aaggccactt gcggttggga ggagatctac     240
gtctgcgtgg tggagatgag caagatttgc atcgagctgg tgcacgagta cgacaccccc     300
ttttgcctgt acctggccac cggcagcaga gtcctctggc tgagatacgc cgagtggctc     360
atgacttgcc ccgtgatcct gatccacctg agcaacatca ccggactggg caccgactac     420
aacaagcgga ccatggtgct cctgatgagc gacatcggtt gcatcgtgtt cggcgccaca     480
gcagcattcg ccaacgaggg ctacgtgaag tgcgcttgtt cctgctgggg catggcttgg     540
ggcatgaaca ccttctacaa cgccgccaag gtgtactacg agagctacgt gctggtgccc     600
tccggaattt gcaagctgct ggtggccgtg atggccggac tgtactacgt gtcttggagc     660
ctgttcccca tcctgtttgc catcggccca gagggatttg gcgtgatcag cctgcaggcc     720
agcaccattg ccacacaatc gccgacgtg ctgagcaaga acatgtgggg cctgatgggc     780
cacttcctgc gggtgcagat ctacaagcac atcctgctgc acggcaacat ccggaagcct     840
atcaagctgc acatgctggg cgaggaggtg gaagtgatgg ctctggtgtc cgaggaggga     900
gaggataccg tg                                                         912
```

<210> SEQ ID NO 18
<211> LENGTH: 927
<212> TYPE: DNA
<213> ORGANISM: Artificial Sequence
<220> FEATURE:
<223> OTHER INFORMATION: Synthetic Oligonucleotide; Mammalian-condon optimized DNA

<400> SEQUENCE: 18

```
atggactatg gcggcgcttt gtctgccgtc ggacgcgaac ttttgttcgt tactaatcct      60
gtggtggtga acgggtccgt cctggtccct gaggatcaat gttactgtgc cggatggatt     120
gaatctcgcg gcacgaacgg cgctcagacc gcgtcaaatg tcctgcagtg gcttgcagca     180
ggattcagca ttttgctgct gatgttctat gcctaccaaa cctggaaatc tacatgcggc     240
tgggaggaga tctatgtgtg cgccattgaa atggttaagg tgattctcga gttcttttt     300
gagtttaaga atccctctat gctctacctt gccacaggac accgggtgca gtggctcgcg     360
tatgcagagt ggctgctcac ttgtcctgtc atccttatcc acctgagcaa cctcaccggc     420
```

```
ctgagcaacg actacagcag gagaaccatg ggactccttg tctcagacat cgggactatc    480
gtgtgggggg ctaccagcgc catggcaacc ggctatgtta aagtcatctt cttttgtctt    540
ggattgtgct atggcgcgaa cacattttt cacgccgcca agcatatat cgagggttat      600 catactgtgc caaagggtcg gtgccgccag gtcgtgaccg gcatggcatg gctgttttc     660 gtgagctggg gtatgttccc aattctcttc attttggggc cgaaggttt tggcgtcctg     720 agcgtctatg gctccaccgt aggtcacacg attattgatc tgatgagtaa aaattgttgg    780
gggttgttgg gacactacct gcgcgtcctg atccacgagc acatattgat tcacggagat    840
atccgcaaaa ccaccaaact gaacatcggc ggaacggaga tcgaggtcga gactctcgtc    900
gaagacgaag ccgaggccgg agccgtg                                        927
```

<210> SEQ ID NO 19
<211> LENGTH: 309
<212> TYPE: PRT
<213> ORGANISM: Chlamydomonas reinhardtii

<400> SEQUENCE: 19

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
```

```
               275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 20
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 20
gtcccgtgca cgctgctcct gctgttggca gccgccctgg ctccgactca gacgcgggcc      60

<210> SEQ ID NO 21
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 21

Met Val Pro Cys Thr Leu Leu Leu Leu Ala Ala Ala Leu Ala Pro
1               5                   10                  15

Thr Gln Thr Arg Ala
            20

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
ttctgctacg agaatgaagt g                                                 21

<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Phe Cys Tyr Glu Asn Glu Val
1               5

<210> SEQ ID NO 24
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 24
aaatccagaa ttacttctga aggggagtat atccctctgg atcaaataga catcaatgtt      60

<210> SEQ ID NO 25
<211> LENGTH: 20
<212> TYPE: PRT
<213> ORGANISM: Artificial Sequence
<220> FEATURE:
```

```
<223> OTHER INFORMATION: Synthetic polypeptide

<400> SEQUENCE: 25

Lys Ser Arg Ile Thr Ser Glu Gly Glu Tyr Ile Pro Leu Asp Gln Ile
1               5                   10                  15

Asp Ile Asn Val
            20
```

CHANNELRHODOPSINS FOR OPTICAL CONTROL OF CELLS

RELATED APPLICATIONS

This application is a National Stage Filing under U.S.C. § 371 of PCT International Application PCT/US12/064665, filed Nov. 12, 2012 which was published under PCT Article 21(2) in English, which claims benefit under 35 U.S.C. § 119(e) of U.S. Provisional application Ser. No. 61/559,076 filed Nov. 12, 2011, the entire content of each of which is incorporated by reference herein in its entirety.

GOVERNMENT INTEREST

This invention was made with government support under Grant Nos. CBET 1053233, DMS 0848804, and EFR 10835878 awarded by the National Science Foundation, under Contract No. HR0011-12-C-0068 awarded by the Defense Advanced Research Projects Agency, and under Grant Nos. DP2 OD002002, R01 DA029639, R01 NS067199, RC1 MH088182 and R01 NS075421 awarded by the National Institutes of Health. The Government has certain rights in the invention.

SEQUENCE LISTING

The instant application incorporates by reference the Sequence Listing in the ASCII text file filed May 12, 2014, entitled "ML01004_ST25.txt", which file was created on Nov. 12, 2012 the size of which file is 50323 bytes.

FIELD OF THE INVENTION

The invention, in some aspects relates to compositions and methods for altering conductance across membranes, cell activity, and cell function, also relates to the use of exogenous light-activated ion channels in cells and subjects.

BACKGROUND OF THE INVENTION

Altering and controlling cell membrane and subcellular region ion permeability has permitted examination of characteristics of cells, tissues, and organisms. Light-driven pumps and channels have been used to silence or enhance cell activity and their use has been proposed for drug screening, therapeutic applications, and for exploring cellular and subcellular function.

Molecular-genetic methods for preparing cells that can be activated (e.g., depolarized) or inactivated (e.g., hyperpolarized) by specific wavelengths of light have been developed (see, for example, Han, X. and E. S. Boyden, 2007, PLoS ONE 2, e299). It has been identified that the light-activated cation channel channelrhodopsin-2 (ChR2), and the light-activated chloride pump halorhodopsin (Halo/NpHR), when transgenically expressed in cell such as neurons, make them sensitive to being activated by blue light, and silenced by yellow light, respectively (Han, X. and E. S. Boyden, 2007, PLoS ONE 2(3): e299; Boyden, E. S., et. al., 2005, Nat Neurosci. 2005 September; 8(9):1263-8. Epub 2005 Aug. 14.). Previously identified light-activated pumps and channels have been restricted to activation by particular wavelengths of light, thus limiting their usefulness.

SUMMARY OF THE INVENTION

The invention, in part, relates to isolated light-activated ion channel polypeptides and methods for their preparation and use. The invention also includes isolated nucleic acid sequences that encode light-driven ion channels of the invention as well as vectors and constructs that comprise such nucleic acid sequences. In addition, the invention in some aspects includes expression of light-activated ion channel polypeptides in cells, tissues, and subjects as well as methods for using the light-activated ion channels to alter conductance across membranes, to alter cell and tissue function, and for use in diagnosis and treatment of disorders.

The invention, in part, also relates to methods for adjusting the voltage potential of cells, subcellular regions, or extracellular regions. Some aspects of the invention include methods of incorporating at least one nucleic acid sequence encoding a light-driven ion channel into at least one target cell, subcellular region, or extracellular region, the ion channel functioning to change transmembrane passage of ions in response to a specific wavelength of light. Exposing an excitable cell that includes an expressed light-driven ion channel of the invention to a wavelength of light that activates the channel, may result in depolarization of the excitable cell. By contacting a cell that includes a light activated ion channel of the invention with particular wavelengths of light, the cell is depolarized. A plurality of light-activated ion channels activated by different wavelengths of light in overlapping or non-overlapping pluralities of cells may be used to achieve multi-color depolarization.

In some embodiments, the invention comprises a method for the expression of newly identified classes of genes that encode light-driven ion channels, in genetically targeted cells, to allow millisecond-timescale generation of depolarizing current in response to pulses of light. Channels of the invention can be genetically expressed in specific cells (e.g., using a virus or other means for delivery) and then used to control cells in intact organisms (including humans) as well as cells in vitro, in response to pulses of light. Given that these channels have different activation spectra from one another and from the state of the art (e.g., ChR2/VChR1), they also allow multiple colors of light to be used to depolarize different sets of cells in the same tissue, by expressing channels with different activation spectra genetically in different cells, and then illuminating the tissue with different colors of light.

In some aspects, the invention uses eukaryotic channelrhodpsins, such as eukaryotic channelrhodpsins, such as *Chloromonas subdivisa* (also referred to herein as: "ChR87"), *Chlamydomonas noctigama* (also referred to herein as: "Chrimson" or "Chr88"), and *Stigeoclonium helveticum* (also referred to herein as: "Chronos" or "ChR90") rhodopsin, and derivatives thereof, are used to depolarize excitable cells. These channelrhodpsins, or derivatives thereof, can also be used to modify the pH of cells, or to introduce cations as chemical transmitters.

The ability to optically perturb, modify, or control cellular function offers many advantages over physical manipulation mechanisms, such as speed, non-invasiveness, and the ability to easily span vast spatial scales from the nanoscale to macroscale. One such approach is an opto-genetic approach, in which heterologously expressed light-activated membrane polypeptides such as a light activated ion channel of the invention, are used to move ions with various spectra of light.

According to an aspect of the invention, methods of altering ion conductivity of a membrane are provided. The methods including a) expressing in a membrane a light-activated ion channel polypeptide comprising an amino acid sequence of a wild-type or modified light-activated *Chlamydomonas noctigama*, *Stigeoclonium helveticum*, or *Chlo-* romonas subdivisa polypeptide and b) contacting the light-activated ion channel polypeptide with a light that activates the light-activated ion channel and alters the ion conductivity of the membrane. In some embodiments, the light-activated ion channel polypeptide comprises an amino acid sequence of a wild-type or modified light-activated Chlamydomonas noctigama polypeptide and the activating light has a wavelength between 365 nm and 700 nm. In certain embodiments, the activating light has a wavelength from 530 nm to 640 nm, and optionally, the activating light has a wavelength of 590 nm. In some embodiments, contacting the light-activated ion channel polypeptide with a light having a wavelength greater than 720 nm does not activate the ion channel. In some embodiments, the membrane is not a membrane in which the light-activated ion channel naturally occurs. In some embodiments, the light-activated ion channel is an isolated ion channel. In some embodiments, the membrane is in cell. In some embodiments, the cell is a neuronal cell and the method further comprises contacting the ion channel polypeptide with a light having a wavelength up to 660 nm under conditions suitable to produce a spike in the neuronal cell. In certain embodiments, the nucleic acid sequence encoding the light-activated ion channel polypeptide comprises the nucleic acid sequence set forth as SEQ ID NO:3. In some embodiments, the amino acid sequence of the light-activated ion channel polypeptide comprises SEQ ID NO:2. In some embodiments, the amino acid sequence of the light-activated ion channel polypeptide comprises a modified Chlamydomonas noctigama light-activated ion channel sequence having at least 70%, 75%, 80%, 85%, 90°%, 95%, or 99% identity to amino acids 86-320 of SEQ ID NO:2 and 95%, 96%, 97%, 98%, 99% or 100% identity to the remaining amino acids in the sequence set forth as SEQ ID NO:2. In certain embodiments, the amino acid sequence of the light-activated ion channel polypeptide comprises SEQ ID NO:5. In some embodiments, the amino acid sequence of the light-activated ion channel polypeptide comprises a modified Chlamydomonas noctigama light-activated ion channel sequence having at least 70%, 75%, 80%, 85%, 90%, 95%, or 99% identity to amino acids 86-320 of SEQ ID NO:5 and 95%, 96%, 97%, 98%, 99% or 100% identity to the remaining amino acids in the sequence set forth as SEQ ID NO:5. In some embodiments, the light-activated ion channel polypeptide comprises an amino acid sequence of a wild-type or modified light-activated Stigeoclonium helveticum polypeptide and the light that activates the ion channel has a wavelength between 365 nm and 630 nm. In some embodiments, the light that activates the ion channel has a wavelength from 430 nm to 550 nm, and optionally, has a wavelength of 500 nm. In certain embodiments, contacting the polypeptide with a light having a wavelength greater than 650 nm does not activate the ion channel. In some embodiments, the cell is a neuronal cell and the method further includes contacting the ion channel polypeptide with a light having a wavelength between 430 nm and 550 nm in a manner to produce a spike in the neuronal cell. In some embodiments, the nucleic acid sequence encoding the light-activated ion channel polypeptide comprises the nucleic acid sequence set forth as SEQ ID NO:8. In certain embodiments, the amino acid sequence of the light-activated ion channel polypeptide comprises SEQ ID NO:7. In some embodiments, the amino acid sequence of the light-activated ion channel polypeptide comprises a modified Stigeoclonium helveticum light-activated ion channel sequence having at least 70%, 75%, 80%, 85%, 90%, 95%, or 99% identity to amino acids 61-295 of SEQ ID NO:7 and 95%, 96%, 97%, 98%, 99% or 100% identity to the remaining amino acids in the sequence set forth as SEQ ID NO:7. In some embodiments, the light-activated ion channel comprises an amino acid sequence of a wild-type or modified light-activated Chloromonas subdivisa polypeptide and the light that activates the ion channel is a light having a wavelength of between 365 nm and 630 nm and a peak activating wavelength of 515 nm. In some embodiments, the light-activated ion channel is encoded by the nucleic acid sequence set forth as SEQ ID NO:12. In certain embodiments, the amino acid sequence of the light-activated ion channel is set forth as SEQ ID NO: 11. In some embodiments, the amino acid sequence of the light-activated ion channel polypeptide comprises a modified Chloromonas subdivisa light-activated ion channel sequence having at least 70%, 75%, 80%, 85%, 90%, 95%, or 99% identity to amino acids 81-315 of SEQ ID NO: 11 and 95%, 96%, 97%, 98%, 99% or 100% identity to the remaining amino acids in the sequence set forth as SEQ ID NO: 11. In some embodiments, the light-activated ion channel does not activate in response to contact with light having a wavelength greater than 650 nm. In certain embodiments, the membrane is a cell membrane. In some embodiments, the cell is a human cell. In some embodiments, the membrane is a cell membrane of a neuronal cell, a nervous system cell, a cardiac cell, a circulatory system cell, a visual system cell, or an auditory system cell. In certain embodiments, altering the ion conductivity of the membrane depolarizes the cell.

According to another aspect of the invention, an isolated light activated ion channel polypeptide is provided. The light-activated ion channel polypeptide includes an amino acid sequence of a wild-type or modified light-activated Chlamydomonas noctigama, Stigeoclonium helveticum, or Chloromonas subdivisa channel polypeptide. In some embodiments, the light-activated ion channel polypeptide comprises an amino acid sequence of a wild-type or modified light-activated Chlamydomonas noctigama polypeptide and activating the ion channel comprises contacting the ion channel polypeptide with a light having a wavelength between 365 nm and 700 nm. In some embodiments, activating the ion channel comprises contacting the ion channel polypeptide with a light having a wavelength from 530 nm to 640 nm, and optionally having a wavelength of 590 nm. In some embodiments, contacting the ion channel polypeptide with a light having a wavelength greater than 720 nm does not activate the ion channel. In certain embodiments, the nucleic acid sequence encoding the light-activated ion channel polypeptide comprises the nucleic acid sequence set forth as SEQ ID NO:3. In some embodiments, the amino acid sequence of the light-activated ion channel polypeptide comprises SEQ ID NO:2. In some embodiments, the amino acid sequence of the light-activated ion channel polypeptide comprises a modified Chlamydomonas noctigama light-activated ion channel sequence having at least 70%, 75%, 80%, 85%, 90%, 95%, or 99% identity to amino acids 86-320 of SEQ ID NO:2 and 95%, 96%, 97%, 98%, 99% or 100% identity to the remaining amino acids in the sequence set forth as SEQ ID NO:2. In some embodiments, the amino acid sequence of the light-activated ion channel polypeptide comprises SEQ ID NO:5. In certain embodiments, the amino acid sequence of the light-activated ion channel polypeptide comprises a modified Chlamydomonas noctigama light-activated ion channel sequence having at least 70%, 75%, 80%, 85%, 90%, 95%, or 99% identity to amino acids 86-320 of SEQ ID NO:5 and 95%, 96%, 97%, 98%, 99% or 100% identity to the remaining amino acids in the sequence set forth as SEQ ID NO:5. In some embodiments, the light-activated ion channel polypeptide comprises an amino acid sequence of a wild-type or modified light-activated *Stigeoclonium helveticum* polypeptide and activating the ion channel comprises contacting the ion channel polypeptide with a light having a wavelength between 365 nm and 630 nm. In some embodiments, activating the ion channel includes contacting the ion channel polypeptide with a light having a wavelength from 430 nm to 550 nm, and optionally having a wavelength of 500 nm. In some embodiments, contacting the ion channel polypeptide with a light having a wavelength greater than 650 nm does not activate the ion channel. In certain embodiments, the nucleic acid sequence encoding the light-activated ion channel polypeptide comprises the nucleic acid sequence set forth as SEQ ID NO:8. In some embodiments, the amino acid sequence of the light-activated ion channel polypeptide comprises SEQ ID NO:7. In some embodiments, the amino acid sequence of the light-activated ion channel polypeptide comprises a modified *Stigeoclonium helveticum* light-activated ion channel sequence having at least 70%, 75%, 80%, 85%, 90%, 95%, or 99% identity to amino acids 61-295 of SEQ ID NO:7 and 95%, 96%, 97%, 98%, 99% or 100% identity to the remaining amino acids in the sequence set forth as SEQ ID NO:7. In certain embodiments, the light-activated ion channel includes an amino acid sequence of a wild-type or modified light-activated *Chloromonas subdivisa* polypeptide and the light that activates the ion channel is a light having a wavelength of between 365 nm and 630 nm and a peak activating wavelength of 515 nm. In some embodiments, the light-activated ion channel is encoded by the nucleic acid sequence set forth as SEQ ID NO: 12. In some embodiments, the amino acid sequence of the light-activated ion channel is set forth as SEQ ID NO: 11. In certain embodiments, the amino acid sequence of the light-activated ion channel polypeptide comprises a modified *Chloromonas subdivisa* light-activated ion channel sequence having at least 70%, 75%, 80%, 85%, 90%, 95%, or 99% identity to amino acids 82-315 of SEQ ID NO: 11 and 95%, 96%, 97%, 98%, 99% or 100% identity to the remaining amino acids in the sequence set forth as SEQ ID NO: 11. In some embodiments, the light-activated ion channel does not activate in response to contact with light having a wavelength greater than 515 nm. In some embodiments, the light-activated ion channel polypeptide is expressed in a membrane. In certain embodiments, the membrane is mammalian cell membrane. In some embodiments, the cell is an excitable cell. In some embodiments, the cell is in a subject. In some embodiments, the membrane is a cell membrane of a neuronal cell, a nervous system cell, a cardiac cell, a circulatory system cell, a visual system cell, or an auditory system cell. In certain embodiments, altering the ion conductivity of the membrane depolarizes the cell.

According to another aspect of the invention, a vector that includes a nucleic acid sequence that encodes any of the aforementioned light-activated ion channel polypeptides is provided.

According to another aspect of the invention, a cell that includes any of the aforementioned light-activated ion channel polypeptides is provided and the cell is not a cell in which the light-activated ion channel polypeptide naturally occurs. In some embodiments, the cell is a mammalian cell and in certain embodiments the cell is a human cell.

According to another aspect of the invention, methods of assessing the effect of a candidate compound on ion conductivity of a membrane are provided. The methods including (a) contacting a test membrane comprising the isolated light-activated ion channel polypeptide of any one of the aforementioned embodiments with light under conditions suitable for altering ion conductivity of the membrane; (b) contacting the test membrane with a candidate compound; and (c) identifying the presence or absence of a change in ion conductivity of the membrane contacted with the light and the candidate compound compared to ion conductivity in a control cell contacted with the light and not contacted with the candidate compound; wherein a change in the ion conductivity in the test membrane compared to the control indicates an effect of the candidate compound on the ion conductivity of the test membrane. In some embodiments, the membrane is in a cell. In certain embodiments, altering the ion conductivity of the membrane depolarizes the cell. In some embodiments, a change is an increase in ion conductivity of the membrane. In some embodiments, the change is a decrease in ion conductivity of the membrane.

According to another aspect of the invention, methods of treating a disorder in a subject are provided. The methods include (a) administering to a subject in need of such treatment, a therapeutically effective amount of a light-activated ion channel polypeptide of any one of the aforementioned embodiments, to treat the disorder and (b) contacting the cell with light and activating the light-activated ion channel in the cell under conditions sufficient to alter ion conductivity of a cell membrane, wherein altering the conductivity of the cell membrane treats the disorder. In some embodiments, altering the ion conductivity of the membrane depolarizes the cell.

According to yet another aspect of the invention, methods of performing a 2, 3, 4, 5 or more-color light ion channel activation assay in a population of cells are provided. The methods include (a) expressing a blue-light-activated ion channel in a first subpopulation of a population of cells; (b) expressing a red-light-activated ion channel in a second subpopulation of the population of cells, wherein the first and second subpopulations are non-overlapping subpopulations; (c) contacting the population of cells with a plurality of blue light test doses comprising combinations of blue light wavelength, pulse width, and power; (d) measuring transmembrane voltage deflection in a cell of the second subpopulation of cells contacted with the blue light test doses; (e) determining the test blue light dose comprising a maximum blue light power that activates the blue-light activated ion channel in first subpopulation of cells and results in a minimum sub-threshold transmembrane voltage deflection in the second subpopulation of cells; (f) contacting the population of cells with a plurality of blue light test doses comprising a lower power than the maximum blue light power of (e); (g) determining the blue light test doses of (f) that activate the blue-light activated ion channel; (h) contacting the population of cells with a plurality of red light test doses comprising combinations of red light wavelength, pulse width, and power, (i) determining a red light test dose comprising a red light power that activates the second subpopulation of cells; and (j) performing an activity assay comprising contacting the population of cells with the blue light test dose determined in (g) and the red light test dose determined in (i). In certain embodiments, the plurality of blue light test doses comprise wavelengths, pulse widths, and powers independently selected from between 400 nm and 500 nm, 1 ms and 5 ms, and 10 µW/mm$^2$ and 1.0 mW/mm$^2$, respectively. In some embodiments, the red light test dose of (i) is the test dose comprising a minimum red light power that activates the second population of cells. In some embodiments, measuring the transmembrane voltage deflection in (d) comprises patch clamping a cell of the second population of cells and determining one or more voltage changes in the cell. In certain embodiments, the determining in (e) comprises altering the blue light dose by increasing the blue light power from 0.5 mW/mm² to 10 mW/mm²; and measuring the sub-threshold transmembrane voltage deflection in the second subpopulation of cells. In some embodiments, the minimum sub-threshold voltage deflection is less than 15 mV, less than 10 mV, or less than 5 mV. In some embodiments, the maximum blue light power in (e) is between 0.4 mW/mm² and 0.6 mW/mm². In some embodiments, the blue light power in (g) is between 50 µW/mm² and 0.4 mW/mm². In certain embodiments, the red-light activated ion channel comprises an amino acid sequence of a wild-type or modified light-activated *Chlamydomonas noctigama* polypeptide. In some embodiments, the nucleic acid sequence encoding the red light-activated ion channel polypeptide comprises the nucleic acid sequence set forth as SEQ ID NO:3. In some embodiments, the amino acid sequence of the red light-activated ion channel polypeptide comprises SEQ ID NO:2. In some embodiments, the amino acid sequence of the red light-activated ion channel polypeptide comprises a modified *Chlamydomonas noctigama* light-activated ion channel sequence having at least 70%, 75%, 80%, 85%, 90%, 95%, or 99% identity to amino acids 86-320 of SEQ ID NO:2 and 95%, 96%, 97%, 98%, 99% or 100% identity to the remaining amino acids in the sequence set forth as SEQ ID NO:2. In certain embodiments, the amino acid sequence of the red light-activated ion channel polypeptide comprises SEQ ID NO:5. In some embodiments, the amino acid sequence of the red light-activated ion channel polypeptide comprises a modified *Chlamydomonas noctigama* light-activated ion channel sequence having at least 70%, 75%, 80%, 85%, 909%, 95%, or 9/identity to amino acids 86-320 of SEQ ID NO:5 and 95%, 96%, 97%, 98%, 99% or 100% identity to the remaining amino acids in the sequence set forth as SEQ ID NO:5. In some embodiments, the blue-light activated ion channel comprises an amino acid sequence of a wild-type or modified light-activated *Stigeoclonium helveticum* polypeptide. In some embodiments, the nucleic acid sequence encoding the blue light-activated ion channel polypeptide comprises the nucleic acid sequence set forth as SEQ ID NO:8. In some embodiments, the amino acid sequence of the blue light-activated ion channel polypeptide comprises SEQ ID NO:7. In some embodiments, the amino acid sequence of the blue light-activated ion channel polypeptide comprises a modified *Stigeoclonium helveticum* light-activated ion channel sequence having at least 70%, 75%, 80%, 85%, 90% 95%, or 99% identity to amino acids 61-295 of SEQ ID NO:7 and 95%, 96%, 97%, 98%, 99% or 100% identity to the remaining amino acids in the sequence set forth as SEQ ID NO:7. In some embodiments, the plurality of red light test doses comprise wavelengths, pulse widths, and powers independently selected from between 600 nm and 740 nm, 1 ms and 5 ms, and 0.1 mW/mm² and 100 mW/mm², respectively.

BRIEF DESCRIPTION OF THE DRAWINGS

FIG. 1 shows a graph of channelrhodopsin photocurrents measured in cultured hippocampal neurons.

FIG. 3 provides example traces of optically-driven spikes in cultured hippocampal neurons.

FIG. 4 provides graphs showing channelrhodopsin kinetics measured in hippocampal neuron culture voltage clamped at −65 mV.

FIG. 5 provides and graph and traces showing Chrimson blue light crosstalk characterization in cultured neurons.

FIG. 6 provides graphs and traces illustrating Chronos and ChR2 blue light sensitivity in cultured hippocampal neurons.

FIG. 7 provides a graph and photomicrographic images illustrating the strategy used for slice characterization of Chronos and Chrimson.

FIG. 8 provides graphs illustrating whole cell patch clamp characterization of Chrimson and Chronos blue and red light sensitivity in slice.

FIG. 11 provides a schematic diagram, photomicrographic image and traces illustrating paired-pulse illumination in slice that differentially express Chrimson and Chronos in separate neurons.

FIG. 13 provides traces illustrating that the ChR88 K176R mutant has improved kinetics (13 ms tau off) and can mediate high frequency spikes in cultured hippocampal neurons. Exemplar current clamped traces of a single ChR88 K176R expressing neuron are shown.

BRIEF DESCRIPTION OF THE SEQUENCES

Figure 1A:
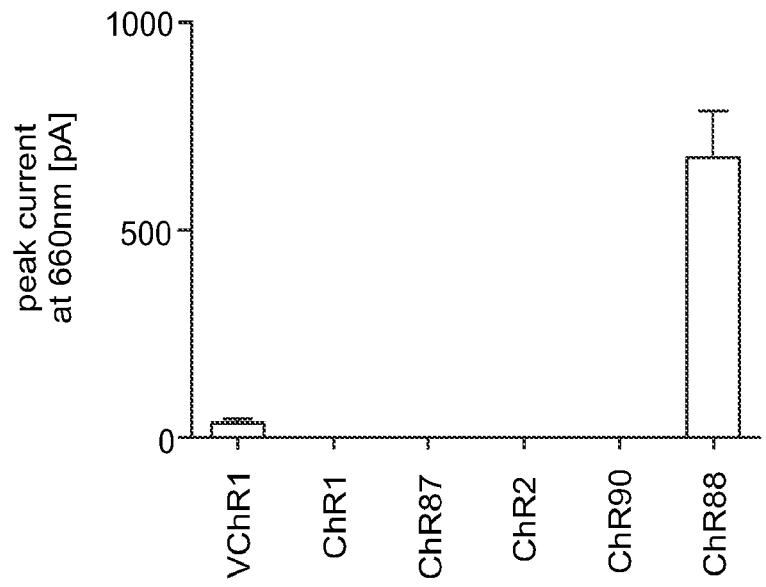
FIG. 1A shows results using red light (660 nm) peak photocurrent at 10 mW mm⁻² for 1 s illumination. ChR88 is the only red light sensitive channelrhodopsin with significant photocurrent at 660 nm.

SEQ ID NO: 1 is amino acid sequence from
Chlamydomonas noctigama
MAELISSATRSLFAAGGINPWPNPYHHEDMGCGGMTPTGECFSTEWWCD

PSYGLSDAGYGYCFVEATGGYLVVGVEKKQAWLHSRGTPGEKIGAQVCQ

-continued
WIAFSIAIALLTFYGFSAWKATCGWEEVYVCCVEVLFVTLEIFKEFSSP

ATVYLSTGNHAYCLRYFEWLLSCPVILIKLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTVTHPTSNLANRNSFVIMAERMRARGIDVRASLDRNGPMIESGR

VILADTDIFVTEMFKAQFAQLPAAIELIPALGADNALQLVQQASVLGGC

DFVMVHPQFLKDNSPSGLVARLRMMGQRVVAFGPANLRELIESCDVDAW

IEAPPINLYQLRQVVAQMQLMRRQAAMMGGMGGGMKGGMSGMGMGMHAG

SMWKQQQMMMQQDGSAMMMPAMQGGAASMRGSGLISAQPGRQASLGGPQ

SVMMGSAMVGSNPLFGTAPSPLGSAVGAEAMGHNLYGNQAAAGGIPAAS

AAADGTDVEMMQQLMSEIDRLKGELGEQDMPR.

SEQ ID NO: 2: ChR88 coding amino acid sequence
that includes residues 1-350 of SEQ ID NO: 1
MAELISSATRSLFAAGGINPWPNPYHHEDMGCGGMTPTGECFSTEWWCD

PSYGLSDAGYGYCFVEATGGYLLVGVEKKQAWLHSRGTPGEKIGAQVCQ

WIAFSIAIALLTFYGFSAWKATCGWEEVYVCCVEVLFVTLEIFKEFSSP

ATVYLSTGNHAYCLRYFEWLLSCPVILIKLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTV.

SEQ ID NO: 3 is a mammalian-codon optimized
DNA sequence encoding ChR88 light-activated ion
channel polypeptide
atggctgagctgatcagcagcgccaccagatctctgtttgccgccgag gcatcaacccttggcctaacccctaccaccacgaggacatggctgtgga ggaatgacacctacaggcgagtgcttcagcaccgagtggtggtgtgacc cttcttacggactgagcgacgccggatacggatattgcttcgtggaggc cacaggcggctacctgtcgtgggagtggagaagaagcaggcttggctgc acagcagaggcacaccaggagaaaagatcggcgcccaggtctgccagtg gattgctttcagcatcgccatcgccctgctgacattctacggcttcagc gcctggaaggccacttgcggttgggaggaggtctacgtctgttgcgtcg aggtgctgttcgtgaccctggagatcttcaaggagttcagcagcccgc cacagtgtacctgtctaccggcaaccacgcctattgcctgcgctacttc gagtggctgctgtcttgccccgtgatcctgatcaagctgagcaacctga gcggcctgaagaacgactacagcaagcggaccatgggcctgatcgtgtc ttgcgtgggaatgatcgtgttcggcatggccgcaggactggctaccgat tggctcaagtggctgctgtatatcgtgtcttgcatctacggcggctaca tgtacttccaggccgccaaggctacgtggaagccaccacagcgtgccta aaggccattgccgcatggtcgtgaagctgatggcctacgcttacttcgc ctcttggggcagctacccaatcctctgggcagtgggaccagaaggactg ctgaagctgagcccttacgccaacagcatcggccacagcatctgcgaca

```
-continued
tcatcgccaaggagttttggaccttcctggcccaccacctgaggatcaa gatccacgagcacatcctgatccacggcgacatccggaagaccaccaag atggagatcggaggcgaggaggtggaagtggaagagttcgtggaggagg aggacgagacacagtg.
```

SEQ ID NO: 4 is transmembrane region of ChR88
including residues 86-320 of SEQ ID NO: 2
GTPGEKIGAQVCQWIAFSIAIALLTFYGFSAWKATCGWEEVYVCCVEVL

FVTLEIFKEFSSPATVYLSTGNHAYCLRYFEWLLSCPVILIKLSNLSGL

KNDYSKRTMGLIVSCVGMIVFGMAAGLATDWLKWLLYIVSCIYGGYMYF

QAAKCYVEANHSVPKGHCRMVVKLMAYAYFASWGSYPILWAVGPEGLLK

LSPYANSIGHSICDIIAKEFWTFLAHHLRIKIHEHILIH.

SEQ ID NO: 5 is derived from ChR88 and
includes K176R substitution
MAELISSATRSLFAAGGINPWPNPYHHEDMGCGGMTPTGECFSTEWWCD

PSYGLSDAGYGYCFVEATGGYLVVGVEKKQAWLHSRGTPGEKIGAQVCQ

WIAFSIAIALLTFYGFSAWKATCGWEEVYVCCVEVLFVTLEIFKEFSSP

ATVYLSTGNHAYCLRYFEWLLSCPVILIRLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTV.

SEQ ID NO: 6 is amino acid sequence from
*Stigeoclonium helveticum*
METAATMTHAFISAVPSAEATIRGLLSAAAVVTPAADAHGETSNATTAG

ADHGCFPHINHGTELQHKIAVGLQWFTVIVAIVQLIFYGWHSFKATTGW

EEVYVCVIELVKCFIELFHEVDSPATVYQTNGGAVIWLRYSMWLLTCPV

ILIHLSNLTGLHEEYSKRTMTILVTDIGNIVWGITAAFTKGPLKILFFM

IGLFYGVTCFFQIAKVYIESYHTLPKGVCRKICKIMAYVFFCSWLMFPV

MFIAGHEGLGLITPYTSGIGHLILDLISKNTWGFLGHHLRVKIHEHILI

HGDIRKTTTINVAGENMEIETFVDEEEEGGVNHGTADLAHRASFQKMGD

RLRAQGVTVRASLDAHEVPPADEENKFAQKSAAANMPAYNPGKVILIVP

DMSMVDYFRDQFEQLPTRMELLPALGMDT.

SEQ ID NO: 7 is ChR90 coding amino acid
sequence that includes residues 1-325
of SEQ ID NO: 6
METAATMTHAFISAVPSAEATIRGLLSAAAVVTPAADAHGETSNATTAG

ADHGCFPHINHGTELQHKIAVGLQWFTVIVAIVQLIFYGWHSFKATTGW

EEVYVCVIELVKCFIELFHEVDSPATVYQTNGGAVIWLRYSMWLLTCPV

ILIHLSNLTGLHEEYSKRTMTILVTDIGNIVWGITAAFTKGPLKILFFM

IGLFYGVTCFFQIAKVYIESYHTLPKGVCRKICKIMAYVFFCSWLMFPV

MFIAGHEGLGLITPYTSGIGHLILDLISKNTWGFLGHHLRVKIHEHILI

HGDIRKTTTINVAGENMEIETFVDEEEEGGV.

SEQ ID NO: 8 is a mammalian-codon optimized
DNA sequence encoding ChR90 light-activated
ion channel polypeptide
```
atggaaacagccgcccaatgacccacgcctttatctcagccgtgccta gcgccgaagccacaattagaggcctgctgagcgccgcagcagtggtgac
```

```
-continued
accagcagcagacgctcacggagaaacctctaacgccacaacagccgga gccgatcacggttgcttccccacatcaaccacggaaccgagctgcagc acaagatcgcagtgggactccagtggttcaccgtgatcgtggctatcgt gcagctcatcttctacggttggcacagcttcaaggccacaaccggctgg gaggaggtctacgtctgcgtgatcgagctcgtcaagtgcttcatcgagc tgttccacgaggtcgacagcccagccacagtgtaccagaccaacggagg agccgtgatttggctgcggtacagcatgtggctcctgacttgccccgtg atcctgatccacctgagcaacctgaccggactgcacgaagagtacagca agcggaccatgaccatcctggtgaccgacatcggcaacatcgtgtgggg gatcacagccgcctttacaaagggcccctgaagatcctgttcttcatg atcggcctgttctacggcgtgacttgcttcttccagatcgccaaggtgt atatcgagagctaccacaccctgcccaaaggcgtctgccggaagatttg caagatcatggcctacgtcttcttctgctcttggctgatgttccccgtg atgttcatcgccggacacgagggactgggcctgatcacaccttacacca gcggaatcggccacctgatcctggatctgatcagcaagaacacttgggg cttcagggccaccacctgagagtgaagatccacgagcacatcctgatcc acggcgacatccggaagacaaccatcatcaacgtggccggcgagaacat ggagatcgagaccttcgtcgacgaggaggaggagggaggagtg.
```

SEQ ID NO: 9 is transmembrane region of ChR90
including residues 61-295 of SEQ ID NO: 7
GTELQHKIAVGLQWFTVIVAIVQLIFYGWHSFKATTGWEEVYVCVIELV

KCFIELFHEVDSPATVYQTNGGAVIWLRYSMWLLTCPVILIHLSNLTGL

HEEYSKRTMTILVTDIGNIVWGITAAFTKGPLKILFFMIGLFYGVTCFF

QIAKVYIESYHTLPKGVCRKICKIMAYVFFCSWLMFPVMFIAGHEGLGL

ITPYTSGIGHLILDLISKNTWGFLGHHLRVKIHEHILIH.

SEQ ID NO: 10 is amino acid sequence from
*Chloromonas subdivisa*
MSRLVAASWLLALLLCGITSTTTASSAPAASSTDGTAAAAVSHYAMNGF

DELAKGAVVPEDHFVCGPADKCYCSAWLHSHGSKEEKTAFTVMQWIVFA

VCIISLLFYAYQTWRATCGWEEVYVTIIELVHVCFGLWHEVDSPCTLYL

STGNMVLWLRYAEWLLTCPVILIHLSNLTGMKNDYNKRTMALLVSDVGC

IVWGTTAALSTDFVKIIFFFLGLLYGFYTFYAAAKIYIEAYHTVPKGIC

RQLVRLQAYDFFFTWSMFPILFMVGPEGFGKITAYSSGIAHEVCDLLSK

NLWGLMGHFIRVKIHEHILVHGNITKKTKVNVAGDMVELDTYVDQDEEH

DEGTIDRGTQELANRHSFVVMRENMRAKGVDVRASLGDIDGTEMTKAGN

MNGTLEPGRIILCVPDMSLVDFFREQFSQMPVPFEVVPALGPEVALQLV

QQALSIGGANYIDYVM.

SEQ ID NO: 11 ChR87 coding amino acid sequence
that includes residues 1-346 of SEQ ID NO: 10
MSRLVAASWLLALLLCGITSTTTASSAPAASSTDGTAAAAVSHYAMNGF

DELAKGAVVPEDHFVCGPADKCYCSAWLHSHGSKEEKTAFTVMQWIVFA

VCIISLLFYAYQTWRATCGWEEVYVTIIELVHVCFGLWHEVDSPCTLYL

STGNMVLWLRYAEWLLTCPVILIHLSNLTGMKNDYNKRTMALLVSDVGC

-continued
IVWGTTAALSTDFVKIIFFFLGLLYGFYTFYAAAKIYIEAYHTVPKGIC

RQLVRLQAYDFFFTWSMFPILFMVGPEGFGKITAYSSGIAHEVCDLLSK

NLWGLMGHFIRVKIHEHILVHGNITKKTKVNVAGDMVELDTYVDQDEEH

DEG.

SEQ ID NO: 12 is a mammalian-codon optimized
DNA sequence encoding ChR87 light-activated
ion channel polypeptide
atgagcagactggtcgccgcttcttggctgctggctctcctcctctgcg gaattaccagcacaacaacagcctctagcgcccagcagcttcttctac agacggaacagccgccgcagcagtgtctcactacgccatgaacggcttc gacgagctggctaaaggagccgtggtgccagaagaccactttgtctgcg gaccagccgacaagtgctattgctccgcttggctgcacagccacggaag caaggaggagaagaccgccttcaccgtcatgcagtggatcgtgttcgcc gtctgcatcatcagcctgctgttctacgcctaccagacttggagggcta cttgcggttgggaggaggtgtacgtgaccatcatcgagctggtccacgt ctgcttcggactctggcacgaggtcgatagccctgtaccctgtacctg agcacaggcaacatggtcctctggctgagatacgccgagtggctgctga cttgccccgtgatcctgatccacctgagcaacctgaccggcatgaagaa cgactacaacaagcggaccatggccctgctggtgtcagacgtgggctgt atcgtgtggggaacaacagccgccctgagcaccgatttcgtgaagatca tcttcttcctcctgggcctgctgtacggcttctacaccttctacgccgc cgccaagatctacatcgaggcctaccacaccgtgcccaagggcatttgt agacagctcgtgcggctgcaggcctacgacttcttcttcacttggagca tgttccccatcctgttcatggtcggcccagagggattcggcaagatcac cgcctacagcagcggaatcgcccacgaagtgtgcgatctgctgagcaag aacctctggggcctgatgggccacttcatccgcgtgaagatccacgagc acatcctggtgcacggcaacatcaccaagaagaccaaggtcaacgtggc cggcgacatggtggaactggacacctacgtggaccaggacgaggaacac gacgaggga.

SEQ ID NO: 13 is transmembrane region of ChR87
including residues 81-315 of SEQ ID NO: 11
GSKEEKTAFTVMQWIVFAVCIISLLFYAYQTWRATCGWEEVYVTIIELV

HVCFGLWHEVDSPCTLYLSTGNMVLWLRYAEWLLTCPVILIHLSNLTGM

KNDYNKRTMALLVSDVGCIVWGTTAALSTDFVKIIFFFLGLLYGFYTFY

AAAKIYIEAYHTVPKGICRQLVRLQAYDFFFTWSMFPILFMVGPEGFGK

ITAYSSGIAHEVCDLLSKNLWGLMGHFIRVKIHEHILVH.

SEQ ID NO: 14 amino acid sequence for
Neochlorosarcina sp. Rhodopsin. This light-
activated ion channel is referred to herein
as ChR62.
MADFVWQGAGNGGPSAMVSHYPNGSVLLESSGSCYCEDWYTSRGNHVEH

SLSNACDWFAFAISVIFLVYYAWAAFNSSVGWEEIYVCTVELIKVSIDQ

FLSSNSPCTLYLSTGNRVLWIRYGEWLLTCPVILIHLSNVTGLKDNYSK

RTMALLVSDIGTIVFGVTSAMCTGYPKVIFFILGCCYGANTFFNAAKVY

LEAHHTLPKGSCRTLRILMAYTYYASWGMFPILFVLGPESFGHMNMYQS

-continued
NIAHTVIDLMSKNIWGMLGHFLRHKIREHILIHGDLRTTTTVNVAGEEM

QVETMVAAEDADETTV.

SEQ ID NO: 15 is the mammalian codon-optimized
DNA sequence for the Neochlorosarcina rhodopsin.
This light-activated ion channel is referred to
herein as ChR62.
atggccgacttcgtgtggcagggagctggaaacggaggaccaagcgcca tggtgtcccactaccccaatggcagcgtgctgctggagagctccggcag ctgctactgtgaagactggtatacttctcggggcaaccacgtggagcat tctctgagtaatgcttgcgattggttcgcctttgctatcagcgtgattt tcctggtgtactatgcctgggccgcttttaactctagtgtgggctggga ggaaatctacgtgtgcaccgtggagctgatcaaggtgagcattgatcag ttcctgagctccaactctccttgtaccctgtacctgagtacagggaata gggtgctgtggatcagatatggcgaatggctgctgacttgtccagtgat cctgattcacctgtccaacgtgacagggctgaaggacaattactctaaa cgcactatggctctgctggtgagtgatatcgggaccatcgtgttcggcg tgacttctgccatgtgcaccggatacccaaagtgatcttctttattct gggctgctgttatggagctaacacattctttaatgccgctaaggtgtac ctggaggcccaccatacactgcctaaaggctcttgtaggactctgatca gactgatggcctataacctactatgctagttggggaatgttccccattct gtttgtgctgggacctgagagcttcggccacatgaacatgtaccagtcc aatatcgcccataccgtgattgacctgatgtccaagaacatctggggaa tgctggggcactttctgcggcataaaattcgcgagcacatcctgattca tggagatctgcggaccacaactaccgtgaatgtggctggggaggaaatg caggtggaaacaatggtggccgctgaggacgccgatgaaacaactgtg.

SEQ ID NO: 16 is the amino acid sequence for
Heterochlamydomonas inaequalis rhodopsin. This
light-activated ion channel is referred to
herein as ChR93.
MGGIGGGGIQPRDYSYGANGTVCVNPDVCFCLDWQQPFGSNMENNVSQG

FQLFTIALSACILMFYAYEWYKATCGWEEIYVCVVEMSKICIELVHEYD

TPFCLYLATGSRVLWLRYAEWLMTCPVILIHLSNITGLGTDYNKRTMVL

LMSDIGCIVFGATAAFANEGYVKCACFLLGMAWGMNTFYNAAKVYYESY

VLVPSGICKLLVAVMAGLYYVSWSLFPILFAIGPEGFGVISLQASTIGH

TIADVLSKNMWGLMGHFLRVQIYKHILLHGNIRKPIKLHMLGEEVEVMA

LVSEEGEDTV.

SEQ ID NO: 17 is the mammalian codon-optimized
DNA sequence for the Heterochlamydomonas
inaequalis rhodopsin, this light-activated ion
channel is referred to herein as ChR93.
atgggaggaattggcggaggcggcattcagcctagagactacagctacg gcgccaacggaacagtctgcgtgaaccccgacgtctgcttctgtctgga ttggcagcagcccttcggctctaacatggagaacaacgtgtcccagggc ttccagctgtttaccatcgccctgagcgccgcatcctgatgttctacgc ctacgagtggtacaaggccacttgcggttgggaggagatctacgtctgc gtggtggagatgagcaagatttgcatcgagctggtgcacgagtacgaca cccccttttgcctgtacctggccaccggcagcagagtcctctggctgag atacgccgagtggctcatgacttgccccgtgatcctgatccacctgagc aacatcaccggactgggcaccgactacaacaagcggaccatggtgctcc tgatgagcgacatcggttgcatcgtgttcggcgccacagcagcattcgc caacgagggctacgtgaagtgcgcttgtttcctgctgggcatggcttgg ggcatgaacaccttctacaacgccgccaaggtgtactacgagagctacg tgctggtgccctccggaatttgcaagctgctggtggccgtgatggccgg actgtactacgtgtcttggagcctgttccccatcctgtttgccatcggc ccagagggatttggcgtgatcagcctgcaggccagcaccattggccaca caatcgccgacgtgctgagcaagaacatgtggggcctgatgggccactt cctgcgggtgcagatctacaagcacatcctgctgcacggcaacatccgg aagcctatcaagctgcacatgctgggcgaggaggtggaagtgatggctc tggtgtccgaggagggagaggataccgtg.

SEQ ID NO: 18 is the mammalian codon-optimized
DNA sequence that encodes the wild-type
Channelrhodopsin-2, (see: Boyden, E. et al.,
Nature Neuroscience 8, 1263-1268 (2005) and
Nagel, G., et al. PNAS Nov. 25, 2003 vol.
100 no. 24 13940-13945), also referred to
herein as ChR2:
atggactatggcggcgctttgtctgccgtcggacgcgaactttgttcg ttactaatcctgtggtggtgaacgggtccgtcctggtccctgaggatca atgttactgtgccggatggattgaatctcgcggcacgaacggcgctcag accgcgtcaaatgtcctgcagtggcttgcagcaggattcagcattttgc tgctgatgttctatgcctaccaaacctggaaatctacatgcggctggga ggagatctatgtgtgcgccattgaaatggttaaggtgattctcgagttc ttttttgagtttaagaatccctctatgctctaccttgccacaggacacc gggtgcagtggctgcgctatgcagagtggctgctcacttgtcctgtcat ccttatccacctgagcaacctcaccggcctgagcaacgactacagcagg agaaccatgggactccttgtctcagacatcgggactatcgtgtgggggg ctaccagcgccatggcaaccggctatgttaaagtcatcttcttttgtct tggattgtgctatggcgcgaacacatttttcacgccgccaaagcatat atcgagggttatcatactgtgccaaagggtcggtgccgccaggtcgtga ccggcatggcatggctgttttcgtgagctggggtatgttcccaattct cttcattttggggcccgaaggttttggcgtcctgagcgtctatggctcc accgtaggtcacacgattattgatctgatgagtaaaaattgttggggt tgttgggacactacctgcgcgtcctgatccacgagcacatattgattca cggagatatccgcaaaaccaccaaactgaacatcggcggaacggagatc gaggtcgagactctcgtcgaagacgaagccgaggccggagccgtg.

SEQ ID NO: 19 is the amino acid sequence of
the wild-type Channelrhodopsin-2, (see:
Boyden, E. et al., Nature Neuroscience 8,
1263-1268 (2005) and Nagel, G., et al. PNAS
Nov. 25, 2003 vol. 100 no. 24 13940-13945),
also referred to herein as ChR2:
MDYGGALSAVGRELLFVTNPVVVNGSVLVPEDQCYCAGWIESRGTNGAQ

TASNVLQWLAAGFSILLLMFYAYQTWKSTCGWEEIYVCAIEMVKVILEF

FFEFKNPSMLYLATGHRVQWLRYAEWLLTCPVILIHLSNLTGLSNDYSR

RTMGLLVSDIGTIVWGATSAMATGYVKVIFFCLGLCYGANTFFHAAKAY

IEGYHTVPKGRCRQVVTGMAWLFFVSWGMFPILFILGPEGFGVLSVYGS

TVGHTIIDLMSKNCWGLLGHYLRVLIHEHILIHGDIRKTTKLNIGGTEI

EVETLVEDEAEAGAV.

SEQ ID NO: 20 is the DNA sequence of the 'ss'
signal sequence from truncated MHC class I
antigen:
gtcccgtgcacgctgctcctgctgttggcagccgccctggctccgactc agacgcgggcc.

SEQ ID NO: 21 is the amino acid sequence of
the 'ss' signal sequence from truncated MHC
class I antigen:
MVPCTLLLLLAAALAPTQTRA.

SEQ ID NO: 22 is the DNA sequence of the ER
export sequence (also referred to herein as
ER2":
ttctgctacgagaatgaagtg.

SEQ ID NO: 23 is the amino acid sequence of
the ER export sequence (also referred to
herein as "ER2":
FCYENEV.

SEQ ID NO: 24 is the DNA sequence of KGC,
which is a C terminal export sequence from
the potassium channel Kir2.1:
aaatccagaattacttctgaaggggagtatatccctctggatcaaatag acatcaatgtt.

SEQ ID NO: 25 is the amino acid sequence of
KGC, which is a C terminal export sequence
from the potassium channel Kir2.1:
KSRITSEGEYIPLDQIDINV.

DETAILED DESCRIPTION

The invention in some aspects relates to the expression in cells of light-driven ion channel polypeptides that can be activated by contact with one or more pulses of light, which results in strong depolarization of the cell. Light-activated channels of the invention, also referred to herein as light-activated ion channels can be expressed in specific cells, tissues, and/or organisms and used to control cells in vivo, ex vivo, and in vitro in response to pulses of light of a suitable wavelength. Sequences from *Chlamydomonas* such as Chrimson and derivatives thereof, are strongly activated by contact with red light. In addition, light-activated ion channel polypeptides derived from *Stigeoclonium* rhodopsin sequences, have now been identified and characterized as being activated by light having a wavelength between 365 nm and 630 nm.

The light-activated ion channels of the invention are ion channels and may be expressed in a membrane of a cell. An ion channel is an integral membrane protein that forms a pore through a membrane and assist in establishing and modulating the small voltage gradient that exists across the plasma membrane of all cells and are also found in subcellular membranes of organelles such as the endoplasmic reticulum (ER), mitochondria, etc. When a light-activated ion channel of the invention is activated by contacting the cell with appropriate light, the pore opens and permits conductance of ions such as sodium, potassium, calcium, etc. through the pore.

In some embodiments of the invention, light-activated channels may be used to modify the transmembrane potential (and/or ionic composition) of cells (and/or their subcellular regions, and their local environment). For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of light-activated ion channels in one, two, three, or more (e.g. a plurality) of cells in a tissue or organism, can result in depolarization of the single cell or the plurality of cells by contacting the light-activated ion channels with light of suitable wavelength.

*Chlamydomonas*-derived Light-Activated Ion Channels

When expressed in a cell, light-activated ion channels of the invention identified having a *Chlamydomonas* light-activated ion channel sequence or a derivative thereof, can be activated by contacting the cell with light having a wavelength between about 365 nm and 700 nm, between 530 nm and 640 nm, and in some embodiments, a peak activation may occur upon contact with light having a wavelength of 590 nm. Examples of these light-activated ion channels include ChR88 (also referred to herein as Chrimson), K176R substituted Chrimson sequence such as SEQ ID NO: 5; and functional derivatives thereof. In some embodiments of the invention, a *Chlamydomonas* light-activated ion channel is a *Chlamydomonas noctigama* light-activated ion channel.

Contacting an excitable cell that includes a *Chlamydomonas*-derived light-activated ion channel of the invention with a light in the activating range of wavelengths strongly depolarizes the cell. Exemplary wavelengths of light that may be used to depolarize a cell expressing a *Chlamydomonas*-derived light-activated ion channel of the invention, include wavelengths from at least about 365 nm, 385 nm, 405 nm, 425 nm, 445 nm, 465 nm, 485 nm, 505 nm, 525 nm, 545 nm, 565 nm, 585 nm; 605 nm, 625 nm, 645 nm, 665 nm, 685 nm; and 700 nm, including all wavelengths therebetweeen. In some embodiments, *Chlamydomonas*-derived light-activated ion channels of the invention have a peak wavelength sensitivity in of 590 nm, and may elicit spikes up to 660 nm.

In some embodiments of the invention, a *Chlamydomonas*-derived light-activated ion channel, a non-limiting example of which is Chrimson or a K176R substituted Chrimson set forth as SEQ ID NO:5, can drive temporally precise spikes with 1-5 ms pulse width at 0.5 mW/mm$^2$ to >10 mW/mm$^2$ in neurons at its optimal wavelength in slice and in cell culture; and can stimulate at frequency up to 10 Hz reliably at its optimal wavelength. In some embodiments of the invention, an optimal wavelength for a *Chlamydomonas*-derived light-activated ion channel is between 530 nm and 640 nm. In certain embodiments of the invention, the substituted *Chlamydomonas*-derived light-activated ion channel having an amino acid sequence set forth as SEQ ID NO:5, has a decreased tau off from 25 ms to 13 ms, and this K176R mutant can stimulate at frequency up to 60 Hz reliably at optimal wavelength, which may be between 530 nm and 640 nm.

Light-activated ion channels of the invention such as ChR88 and derivatives thereof can be used to depolarize excitable cells in which one or more light-activated ion channels of the invention are expressed. In some embodiments, *Chlamydomonas*-derived light-activated ion channels of the invention can be expressed in a sub-population of cells in a cell population that also includes one or more additional subpopulations of cells that express light-activated ion channels that are activated by wavelengths of light that do not activate a *Chlamydomonas*-derived light-activated ion channel of the invention.

*Stigeoclonium*-Derived Light-Activated Ion Channels

When expressed in a cell, light-activated ion channels of the invention identified having a *Stigeoclonium* light-activated ion channel sequence or a derivative thereof, can be activated by contacting the cell with light having a wavelength between about 365 nm and 630 nm, between 430 nm and 550 nm; and in some embodiments, a peak activation may occur upon contact with light having a wavelength of 500 nm. Examples of these light-activated ion channels include ChR90 (also referred to herein as Chronos) and functional derivatives thereof. In some embodiments of the invention, a *Stigeoclonium* light-activated ion channel is a *Stigeoclonium helveticum* light-activated ion channel.

Contacting an excitable cell that includes a *Stigeoclonium*-derived light-activated ion channel of the invention with a light in the activating range of wavelengths strongly depolarizes the cell. Exemplary wavelengths of light that may be used to depolarize a cell expressing a *Stigeoclonium*-derived light-activated ion channel of the invention, include wavelengths from at least about 365 nm, 385 nm, 405 nm, 425 nm, 445 nm, 465 nm, 485 nm, 505 nm, 525 nm, 545 nm, 565 nm, 585 nm; 605 nm, and 630 nm, including all wavelengths therebetweeen. In some embodiments, *Stigeoclonium*-derived light-activated ion channels of the invention have a peak wavelength sensitivity in of 500 nm. In some embodiments of the invention, a *Stigeoclonium*-derived light-activated ion channel can drive temporally precise spikes with 1-5 ms pulse width at 50 nW/mm$^2$ to >10 mW/mm$^2$ in neurons at "optimal wavelength" in slice and cultured cells; and can stimulate at frequency >100 Hz at "optimal wavelength". As used herein an optimal wavelength for a *Stigeoclonium*-derived light-activated ion channel may be a wavelength between 430 nm and 550 nm.

Light-activated ion channels of the invention such as ChR90 and derivatives thereof can be used to depolarize excitable cells in which one or more light-activated ion channels of the invention are expressed. In some embodiments, *Stigeoclonium*-derived light-activated ion channels of the invention can be expressed in a sub-population of cells in a cell population that also includes one or more additional subpopulations of cells that express light-activated ion channels that are activated by wavelengths of light that do not activate a *Stigeoclonium*-derived light-activated ion channel of the invention.

*Chloromonas*-Derived Light-Activated Ion Channels

When expressed in a cell, light-activated ion channels of the invention identified having a *Chloromonas* light-activated ion channel sequence or a derivative thereof, can be activated by contacting the cell with light having a wavelength between about 365 nm and 630 nm, between 450 nm and 570 nm; and in some embodiments, a peak activation may occur upon contact with light having a wavelength of 525 nm. In some embodiments of the invention, a *Chloromonas* light-activated ion channel, a non-limiting example of which is ChR87, does not exhibit light sensitivity (activation) at wavelengths greater than 650 nm, and can drive temporally precise spikes with 1-5 ms pulse width at 0.1 mW/mm$^2$ to greater than 10 mW/mm$^2$ in neurons at its optimal wavelength in both slice and cell culture. In some embodiments of the invention, a *Chloromonas* light-activated ion channel (such as ChR87) can stimulate at frequency >60 Hz at its optimal wavelength. In some aspects of the invention the optimal wavelength for a *Chloromonas* light-activated ion channel, a non-limiting example of which is ChR87, is between 450 and 570 nm. Examples of *Chloromonas* light-activated ion channels include ChR87 and functional derivatives thereof. In some embodiments of the invention, a *Chloromonas* light-activated ion channel is a *Chloromonas subdivisa* light-activated ion channel.

*Chloromonas*-, *Chlamylrmonas*-, and *Stigeoclonium*-derived light-activated ion channels of the invention permit ion conductance and depolarization when contacted under suitable conditions with an appropriate wavelength of light. As will be understood by those in the art, the term "depolarized" used in the context of cells means an upward change in the cell voltage. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold an action potential (e.g. a spike) results. When a cell is depolarized by activating a light-activated ion channel of the invention with an appropriate wavelength of light, the cell voltage becomes more positive than the baseline level, and an incoming signal may more easily raise the cell's voltage sufficiently to reach the threshold and trigger an action potential in the cell. It has been discovered that by contacting a cell expressing a *Chlamydomonas*-derived light-activated ion channel of the invention with light in the range between about 365 nm to about 700 nm, the voltage of the cell becomes less negative and may rise by at least about 20, 30, 40, 50, 60, 70, 80, 90, 100, mV (depending on the cell type) thus, depolarizing the cell. Similarly, it has been discovered that by contacting a cell expressing a *Stigeoclonium*-derived light-activated ion channel of the invention with light in the range between about 365 nm and 630 nm the voltage of the cell becomes less negative by as much as at least 20, 30, 40, 50, 60, 70, 80, 90, 100, mV, (depending on cell type). Similarly, it has been discovered that by contacting a cell expressing a *Chloromonas*-derived light-activated ion channel of the invention with light in the range between about 365 nm and 630 nm, or between 450 nm and 570 nm the voltage of the cell becomes less negative by as much as at least 20, 30, 40, 50, 60, 70, 80, 90, 100, mV, (depending on cell type). As used herein, the term "activate" when used in reference to a light-activated ion channel of the invention, means to open the channel making it permissive to ion conduction through the channel.

Specific ranges of wavelengths of light that in some embodiments of the invention are useful to activate ion channels of the invention are provided and described herein. It will be understood that a light of appropriate wavelength for activation and will have a power and intensity appropriate for activation. It is well known in the art that light pulse duration, intensity, and power are parameters that can be altered when activating a channel with light. Thus, one skilled in the art will be able to adjust power, intensity appropriately when using a wavelength taught herein to activate a light-activated ion channel of the invention. A dose light that contacts a light-activated ion channel of the invention may be determined based on the wavelength, pulse length, and power of the light that contacts the light-activated ion channel. Thus, as a non-limiting example, a dose may have a wavelength of 550 nm, a 4 ms pulse length, and a 0.5 mW/mm$^2$ power and another light dose may have a wavelength of 550 nm, a 3 ms pulse length and a 0.5 mW/mm$^2$ power. Those skilled in the art will understand methods to select a dose of light by independently selecting a wavelength, a pulse length, and a power for the light with which a light-activated ion channel of the invention is contacted. In some embodiments, wavelength and pulse length may be held steady, and power incrementally increased to examine activation parameters of a light-activated ion channel of the invention. Similarly, in certain embodiments of the invention may include incremental wavelength increases while pulse length and power are held steady, or incremental pulse length increases while wavelength and power are held steady. In some embodiments of the invention two or more of wavelength, pulse length, and power of a light may be incrementally altered to examine the effect on activation of a light-activating ion channel of the invention.

A benefit of a light-activated ion channel of the invention is the ability to "tune" the light-activated ion channel's response using appropriate illumination variables (e.g., wavelength, intensity, duration, etc.) (also referred to herein as dose) to activate the channel. Methods of adjusting illumination variables are well-known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19): 8143-8. Epub 2007 May 1, each of which is incorporated herein by reference. Thus, it is possible to utilize a narrow range of one or more illumination characteristics to activate a light-activated ion channel of the invention. The expression of light-activated ion channels that are activated by different wavelengths of light in distinct, separate, subpopulations in a cell population can permit application of different illumination parameters to the population with an effect of differentially activating the different subpopulations through the use specific wavelengths of light. Thus, permitting controlled activation of a mixed population of light-activated channels.

In exemplary implementations, the invention comprises methods for preparing and using genes encoding light-activated ion channels of the invention that have now been identified. The invention, in part, also includes isolated nucleic acids comprising sequences that encode light activated ion channels of the invention as well as vectors and constructs that comprise such nucleic acid sequences. In some embodiments the invention includes expression of polypeptides encoded by the nucleic acid sequences, in cells, tissues, and organisms.

Not all channelrhodopsins can be expressed in cells and utilized in this fashion, because many do not traffic properly and/or function in mammalian cells. Many channelrhodopsins were screened in order to identify ChR87, Chrimson, and Chronos as functioning better in mammalian cells than other classes of channelrhodopsins. In addition Chrimson responds strongly to far red light, and therefore, because other channelrhodopsins that depolarize cells respond strongly to ultraviolet or blue light, Chrimson can be expressed in a separate population of cells from a population of cells expressing one of these other opsins, allowing multiple colors of light to be used to excite these two populations of cells or neuronal projections from one site, at different times.

In some embodiments of the invention, light-activated channels are used to modify the transmembrane potential (and/or ionic composition) of cells (and/or their sub-cellular regions, and their local environment). In particular, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration).

Compared to natural gene sequences conventionally used to depolarize neurons, Chronos has demonstrably improved photocurrent generation at all illumination wavelengths except for red wavelength. In addition Chronos can depolarize cells in response to <5 ms pulse of 50-100 uW mm$^{-2}$ of blue or green light with sufficient spectral independence from most green or red channelrhodopsins such as ChR87 or Chrimson, thus permitting multiple colors of light to be used to depolarize different sets of cells in the same tissue, simply by expressing pumps with different activation spectra genetically in different cells, and then illuminating the tissue with different colors of light. In a non-limiting example of an embodiment, one set of cells in a tissue, for example excitatory neurons, express Chrimson, and a second set express Chronos, illuminating the tissue with 630 nm light will preferentially depolarize the first set, and illuminating the tissue with 470 nm light at low powers (<5 mW mm$^{-2}$) will preferentially depolarize the second set. Other pairs of targets that could be modulated with two colors of light in the same illumination area include, but are not limited to two projections to/from one site, or combinations of the cell, its projections, and its organelles, given the ability to target the molecule sub-cellularly.

It has been identified that light-activated ion channels of the invention are, in some embodiments of the invention, activated at different wavelengths than previously identified light-activated ion channels. Thus, light-activated ion channels of the invention can be used in either alone, using a selective light spectrum for activation and depolarization and can also be used in combination with other light-activated ion channels that utilize different wavelength of light for activation and depolarization, thus allowing two, three, four, or more different wavelengths of light to be used to depolarize different sets or subpopulations of cells in a tissue or organism by expressing channels with different activation spectra in different cells and then illuminating the tissue and/or organism with the appropriate wavelengths of light to activate the channels and depolarize the cells.

According to some aspects of the invention, a light-activated ion channel from *Chlamydomonas noctigama* or a derivative thereof may be used in conjunction with a light-activated ion channel from *Stigeoclonium helveticum* or a derivative thereof. The two light-activated ion channels are sensitive to and can be activated with different wavelengths of light than each other. As described herein, certain light-activated ion channels of the invention can depolarize cells in strong response to light with sufficient spectral independence from that of other light-activate ion channels of the invention, thus allowing multiple colors of light to be used to depolarize different sets of cells in the same tissue, by expressing channels with different activation spectra genetically in different cells, and then illuminating the tissue with different colors of light in suitable dose to activate one type of light-activated ion channel but not the other type of light-activated ion channel. In a non-limiting example, if a first subset of cells in a tissue (e.g., excitatory neurons) express ChR88, and a second subset express ChR90 light-activated ion channels of the invention, then illuminating the tissue with a dose of light such as 625 nm, 2 mW/mm$^2$ will preferentially depolarize/drive spike in the first subset (ChR88), and illuminating the tissue with a dose of light such as 470 nm 0.2 mW/mm$^2$ light will preferentially depolarize/drive spike in the second subset (ChR90). Other pairs of targets that could be modulated with two colors of light in the same illumination area include, but are not limited to two projections to/from one site, or combinations of the cell, its projections, and its organelles, given the ability to target the molecule sub-cellularly.

Taxonomy and Sequence Sources

In particular, the present invention includes, in part, novel light-activated ion channels and their use to depolarize cells. In some non-limiting embodiments of the invention one or more newly identified light-activated ion channels may be expressed in cells.

Some light-activated ion channels of the invention have amino acid sequences derived from *Chlamydomonas rhodopsins* that are naturally expressed in the genus *Chlamydomonas noctigama*, or another member of the Chlamydomonadaceae family. *Chlamydomonas noctigama* are phytoplankton and can be found in fresh water environments. Some embodiments of the invention include isolated wild-type or modified nucleic acid and/or amino acid channelrhodopsin sequences from a member of the chlamydomonadaceae family, for example, from *Chlamydomonas noctigama*, and in some aspects, the invention also includes methods for their use.

Some light-activated ion channels of the invention have amino acid sequences derived from *Stigeoclonium* rhodopsins that are naturally expressed in the genus *Stigeoclonium helveticum*, or another member of the Chaetophoracea family. *Stigeoclonium helveticum* are green algae and can be found in fresh water environments. Some embodiments of the invention include isolated wild-type or modified nucleic acid and/or amino acid channelrhodopsin sequences from a member of the Chaetophoracea family, for example, from *Stigeoclonium helveticum*, and in some aspects, the invention also includes methods for their use.

Some light-activated ion channels of the invention have amino acid sequences derived from *Chloromonas* rhodopsins that are naturally expressed in the genus *Chloromonas subdivisa*, or another member of the Chlamydomonadaceae family. *Chloromonas subdivisa* are phytoplankton and can be found in fresh water environments. Some embodiments of the invention include isolated wild-type or modified nucleic acid and/or amino acid channelrhodopsin sequences from a member of the Chlamydomonadaceae family, for example, from *Chloromonas subdivisa*, and in some aspects, the invention also includes methods for their use.

Some light-activated ion channels of the invention have amino acid sequences derived from *Neochlorosarcina* and some light-activated ion channels of the invention have amino acid sequences derived from *Heterochlamydomonas inaequalis* rhodopsins. Some embodiments of the invention include isolated wild-type or modified nucleic acid and/or amino acid channelrhodopsin sequences from *Neochlorosarcina* or from *Heterochlamylomonas inaequalis*, and in some aspects, the invention also includes methods for their use. Sequences of light-activated ion channels of the invention, may be derived from a *Chloromonas* sequence, a *Chlamydomonas* sequence, or a *Stigeoclonium* sequence and may include a wild-type or modified channelrhodopsin sequence, also referred to as a derivative sequence.

A modified light-activated ion channel polypeptide of the invention (also referred to as a derivative of a light-activated ion channel) versus a naturally occurring light activated ion channel may be altered by an substituting 1, 2, 3, 4, 5, 6, 7, 8, 9, 10, or more amino acids, by an insertion and/or deletion of 1, 2, 3, 4, 5, 6, 7, 8, 9, 10, or more amino acids at one or several positions. Both a wild-type light-activated ion channel polypeptide and derivatives thereof may have an identity of at least 20%, 25%, 30%, 35%, 40%, 45%, 50%, 55%, 60%, 65%, 70%, 75%, 80%, 85%, 90%, 95%, or 100%, with the sequence of the transmembrane region of the wild-type light-activated ion channel polypeptide, as long as they retain channel functionality. For ChR87, the amino acid sequence of the transmembrane region is set forth as SEQ ID NO:13, which includes amino acid residues 81-315 of SEQ ID NO: 11. For ChR88, the amino acid sequence of the transmembrane region is set forth as SEQ ID NO:4, which includes amino acid residues 86-320 of SEQ ID NO:2. For ChR90, the amino acid sequence of the transmembrane region is set forth as SEQ ID NO: 9, which includes amino acid residues 61-295 of SEQ ID NO:7. A derivative or modified light-activated ion channel polypeptide of the invention may retain an identity of 20% or more of the transmembrane amino acid sequence from which it was derived.

In contrast, the level of identity between a derivative or modified light-activated ion channel of the invention and the wild-type from which it is derived may be more constrained to maintain the function of the light-activated ion channel. The amino acid sequence of a non-transmembrane region of a derived or modified light-activated ion channel of the invention, may have at least 80%, 85%, 90%, 95%, 96%, 97%, 98%, 99% or 100% identity to the amino acid sequence of the wild-type light-activated ion channel polypeptide from which they are derived.

Thus, for example, in some embodiments, a light-activated ion channel of the invention may be a derivative of ChR87 and have at least 80%, 85%, 90%, 95%, 96%, 97%, 98%, 99% or 100% identity to the non-transmembrane regions of the wild-type polypeptide sequence (SEQ ID NO: 11) of the light-activated ion channel polypeptide from which it is derived. In another non-limiting example, in some embodiments, a light-activated ion channel of the invention may be a derivative of ChR90 and have at least 80%, 85%, 90%, 95%, 96%, 97%, 98%, 99% or 100% identity to the non-transmembrane regions of the wild-type polypeptide sequence (SEQ ID NO:7) of the light-activated ion channel polypeptide from which it is derived. Similarly, in another example, in some embodiments, a light-activated ion channel of the invention may be a derivative of ChR88 and have at least 80%, 85%, 90%, 95%, 96%, 97%, 98%, 99% or 100% identity to the non-transmembrane regions of the wild-type polypeptide sequence (SEQ ID NO:2) of the light-activated ion channel polypeptide from which it is derived. In another non-limiting example of a light-activated ion channel derived from ChR88, a polypeptide that includes K176R substitution in the amino acid sequence of SEQ ID NO:2 functions as a light-activated ion channel of the invention.

As used herein, the term "identity" refers to the degree of relatedness between two or more polypeptide sequences, which may be determined by the match between the sequences. The percentage is obtained as the percentage of identical amino acids in two or more sequences taking account of gaps and other sequence features. The identity between polypeptide sequences can be determined by means of known procedures. Algorithms and programs are available and routinely used by those in the art to determine identity between polypeptide sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

One skilled in the art will understand that light-activated ion channels of the invention can be identified based on sequence similarity or homology to a light-activated ion channel disclosed herein. It will be understood that additional light-activated ion channels may be identified using sequence alignment with one of the light-activated ion channels or derivatives thereof identified herein.

Based on the teaching provided herein regarding the *Cholormonas subdivisa, Chlamydomonas noctigama, Stigeoclonium helveticum* channelrhodopsin sequences having light-activated ion channel function and activity, additional rhodopsin sequences with sufficient amino acid sequence homology to a ChR87, ChR88, or ChR90, respectively, can be identified. The presence of functionality, e.g., activation of a channel by contact with suitable light can be determined using methods described herein, and function light-activated ion channels of the invention can be used in methods described herein. It is understood that that the level of sequence identity with a light-activated ion channel of the invention plus functionality with respect to activation by suitable light contact can be characteristics used to identify additional light-activated ion channels using standard procedures for sequence alignment, comparisons, and assays for ion channel activity.

Light-activated ion channels of the invention are transmembrane channel polypeptides that use light energy to open, permitting ion conductance through their pore, thus altering the potential of the membrane in which they are expressed. A non-limiting example of an ion that can be moved through a pore of the invention includes a sodium ion, a potassium ion, a calcium ion, a proton, etc. Routine methods may be used to measure different ion currents for light-activated ion channels of the invention. Light-activated ion channels of the invention can be activated by sustained light and/or by light pulses and by permitting ion conductance upon activation, light-activated ion channels of the invention can depolarize cells and alter the voltage in cells and organelles in which they are expressed.

The wild-type and modified (derived) *Cholormonas subdivisa, Chlamydomonas noctigama, Stigeoclonium helveticum* rhodopsin nucleic acid and amino acid sequences used in aspects and methods of the invention are "isolated" sequences. As used herein, the term "isolated" used in reference to a polynucleotide, nucleic acid sequence, or polypeptide sequence of a rhodopsin, means a polynucleotide, nucleic acid sequence, or polypeptide sequence that is separate from its native environment and present in sufficient quantity to permit its identification or use. Thus, an isolated polynucleotide, nucleic acid sequence, or to polypeptide sequence of the invention is a polynucleotide, nucleic acid sequence, or polypeptide sequence that is not part of, or included in its native, wild-type cell or organism. For example, a nucleic acid or polypeptide sequence may be naturally expressed in a cell or organism of a member of the *Chloromonas* genus, but when the sequence is not part of or included in a *Chloromonas* cell or organism it is considered to be isolated. Similarly, a nucleic acid or polypeptide sequence may be naturally expressed in a cell or organism of a member of the *Chlamydomonas* genus, but the sequence is not part of or included in a *Chlamydomonas* cell or organism, it is considered to be isolated. Similarly, a nucleic acid or polypeptide sequence may be naturally expressed in a cell or organism of a member of the *Stigeoclonium* genus, but the sequence is not part of or included in a *Stigeoclonium* cell or organism, it is considered to be isolated. Thus, a nucleic acid or polypeptide sequence of a *Chloromonas, Chlamydomonas, Stigeoclonium*, or other light-activated ion channel nucleic acid or polypeptide that is present in a vector, in a heterologous cell, tissue, or organism, etc., is still considered to be an isolated sequence. As used herein the term "host" used in reference to a membrane or cell in which a light-activated ion channel of the invention is expressed, means a membrane or cell that is not a cell or membrane in which the light-activated ion channel is expressed in nature. Thus a host membrane, cell, tissue, or organism for a light-activated ion channel molecule of the invention (such as a light-activated ion channel polypeptide or its encoding nucleic acid), as used herein is a membrane, cell, tissue, or organism in which the light-activated ion channel molecule of the invention does not naturally occur and in which the light-activated ion channel is not naturally expressed. Examples of a host membrane, cell, tissue, or organism include, but are not limited to mammalian (including but not limited to non-human primate, human, etc.), insect, and avian membranes, cells, and tissues; as well as organisms such as mammals, insects, and birds. The term "heterologous" as used herein, means a membrane, cell, tissue, or organism that is not the native cell, tissue, or organism, and a light-activated ion channel polypeptide of the invention or its encoding nucleic acid may be present in a heterologous membrane, cell, tissue, or organism. The terms, "protein", "polypeptides", and "peptides" are used interchangeably herein.

Light-Activated Ion Channel Sequences Including Modified and Derived Sequences

A light-activated ion channel of the invention may comprise a wild-type polypeptide sequence or may be a modified polypeptide sequence. As used herein the term "modified" or "modification" in reference to a nucleic acid or polypeptide sequence refers to a change of one, two, three, four, five, six, or more amino acids in the sequence as compared to the wild-type or other sequence from which it was derived. For example, a modified polypeptide sequence may be identical to a wild-type polypeptide sequence except that it has one, two, three, four, five, or more amino acid substitutions, deletions, insertions, or combinations thereof. In some embodiments of the invention a modified sequence may include one, two, three, four, or more amino acid substitutions in a wild-type light-activated ion channel polypeptide sequence, or in any other light-activated ion channel polypeptide sequence of the invention.

It will be understood that sequences of light-activated ion channels of the invention may be derived from various members of the *Chloromonas* genus, *Chlamydomonas* genus, *Stigeoclonium* genus, *Neochlorosarcina* genus, or *Heterochlamydomonas* genus.

The invention, in some aspects also includes light-activated ion channel polypeptides having one or more substitutions or other modifications from those described herein. For example, sequences of light-activated ion channel polypeptides provided herein can be modified with one or more substitutions, deletions, insertions, or other modifications and such derivative light-activated ion channels can be tested using methods described herein for characteristics including, but not limited to: expression, cell localization, activation and depolarization in response to contact with light using methods disclosed herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Light-activated ion channels that include modifications, including but not limited to one, two, three, four, or more conservative amino acid substitutions can be identified and tested for characteristics including, but not limited to: expression, cell localization, activation and depolarization and depolarization-effects in response to contact with light using methods disclosed herein. As described elsewhere herein, in some polypeptide regions such as the transmembrane region of a light-activated ion channel of the invention, may include modifications that result in less than 100%, 95%, 90%, 85%, 80%, 75%, 70%, 65%, 60%, 55%, 50% identity with the sequence from which its derived, yet may have at least 90%, 95%, 96%, 97%, 98%, 99%, or 100% identity in its non-transmembrane regions of the polypeptide.

Sequence identity can be determined using standard techniques known in the art.

Light-activated ion channel polypeptides of the invention may be shorter or longer than the light-activated ion channel polypeptide sequences set forth herein. Thus, a light-activated ion channel polypeptide may be a full-length polypeptide or functional fragment thereof. In addition, nucleic acids of the invention may be used to obtain additional coding regions, and thus additional polypeptide sequences, using techniques known in the art.

In some aspects of the invention, substantially similar light-activated ion channel polypeptide sequences may have at least 80%, 85%, 90%, 91%, 92%, 93%, 94%, 95%, 96%, 97%, 98%, or 99% or 100% identity to a light-activated ion channel polypeptide sequence disclosed herein, non-limiting examples of which include as ChR62, ChR93, ChR87, ChR88, ChR90, etc. Art-known alignment methods and tools can be used to align substantially similar sequences permitting positional identification of amino acids that may be modified as described herein to prepare a light-activated ion channel of the invention. Standard sequence analysis tools and computer programs, such as those used for alignment, etc. can be used to identify light-activated ion channels of the invention that share one or more functional properties with a light-activated ion channel described herein.

Sequence modifications can be in one or more of three classes: substitutions, insertions, or deletions. These modified sequences, (which may also be referred to as variants, or derivatives) ordinarily are prepared by site specific mutagenesis of nucleic acids in the DNA encoding a light-activated ion channel polypeptide, using cassette or PCR mutagenesis or other techniques known in the art, to produce DNA encoding the modified light-activated ion channel, and thereafter expressing the DNA in recombinant cell culture. Amino acid sequence variants are characterized by the predetermined nature of the variation, a feature that sets them apart from naturally occurring allelic or interspecies variation of the light-activated ion channels of the invention. Modified light-activated ion channels generally to exhibit the same qualitative biological activity as the naturally occurring light-activated ion channel (e.g., wild-type), although variants can also be selected that have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed modified light-activated ion channel screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; and insertions usually will be on the order of from about 1 to 20 amino acids, although considerably larger insertions may be tolerated. Deletions may range from about 1 to about 20 residues, although in some cases deletions may be much larger.

Substitutions, deletions, insertions or any combination thereof may be used to arrive at a final modified light-activated ion channel of the invention. Generally these changes are done on a few amino acids to minimize the alteration of the molecule. However, larger changes may be tolerated in certain circumstances.

Variants of light-activated ion channels set forth herein, may exhibit the same qualitative light-activated ion channel activity as one or more of the sequences set forth herein, such as ChR62, ChR93, ChR87, ChR88, or ChR90, but may show some altered characteristics such as altered photocurrent, stability, speed, compatibility, and toxicity, or a combination thereof. For example, the polypeptide can be modified such that it has an increased photocurrent and/or has less toxicity than another light-activated ion channel polypeptide.

A modified (or derived) light-activated ion channel polypeptide of the invention can incorporate unnatural amino acids as well as natural amino acids. An unnatural amino acid can be included in a light-activated ion channel of the invention to enhance a characteristic such as photocurrent, stability, speed, compatibility, or to lower toxicity, etc.

According to principles of this invention, the performance of light-activated ion channel molecules or classes of molecules can be tuned for optimal use, including in the context of their use in conjunction with other molecules or optical apparatus. For example, in order to achieve optimal contrast for multiple-color stimulation, one may desire to either improve or decrease the performance of one molecule with respect to one another, by the appendage of trafficking enhancing sequences or creation of genetic variants by site-directed mutagenesis, directed evolution, gene shuffling, or altering codon usage. light-activated ion channel molecules or classes of molecules may have inherently varying spectral sensitivity. This may be used to advantage in vivo (where scattering and absorption will vary with respect to wavelength, coherence, and polarization), by tuning the linearity or non-linearity of response to optical illumination with respect to time, power, and illumination history.

In some embodiments, the invention includes the use of targeted site-directed mutagenesis at specific amino acid residues of channelrhodopsins including but not limited to residues of channelrhodopsins of the *Chloromonas* genus, *Chlamydomonas* genus, *Stigeoclonium* genus, *Neochlorosarcina* genus, or *Heterochlamydomonas* genus. Specific locations for single mutations can be identified and alone, or in combination with two or more additional mutations can be placed into a channelrhodopsin sequence and tested with respect to their activation and photocurrent amplitude. Thus, sequences of light-activated ion channels of the invention, and/or similar channelrhodopsin sequences can be modified and the resulting polypeptides tested using methods disclosed herein.

Another aspect of the invention provides nucleic acid sequences that code for a light-activated ion channel of the invention. It would be understood by a person of skill in the art that light-activated ion channel polypeptides of the present invention can be coded for by various nucleic acids. Each amino acid in the protein is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for light-activated ion channel polypeptides of the invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein.

It is understood in the art that the codon systems in different organisms can be slightly different, and that therefore where the expression of a given protein from a given organism is desired, the nucleic acid sequence can be modified for expression within that organism. Thus, in some embodiments, a light-activated ion channel polypeptide of the invention is encoded by a mammalian-codon-optimized nucleic acid sequence, which may in some embodiments be a human-codon optimized nucleic acid sequence. An aspect of the invention provides a nucleic acid sequence that codes for a light-activated ion channel that is optimized to for expression with a mammalian cell. In some embodiments of the invention, a nucleic acid that encodes a light-activated ion channel of the invention includes a nucleic acid sequence optimized for expression in a human cell.

Delivery of Light-Activated Ion Channels

Delivery of a light-activated ion channel polypeptide to a cell and/or expression of a light-activated ion channel in a cell can be done using art-known delivery means.

In some embodiments of the invention a light-activated ion channel polypeptide of the invention is included in a fusion protein. It is well known in the art how to prepare and utilize fusion proteins that comprise a polypeptide sequence. In certain embodiments of the invention, a fusion protein can be used to deliver a light-activated ion channel to a cell and can also in some embodiments be used to target a light-activated ion channel of the invention to specific cells or to specific cells, tissues, or regions in a subject. Targeting and suitable targeting sequences for deliver to a desired cell, tissue or region can be performed using art-known procedures.

It is an aspect of the invention to provide a light-activated ion channel polypeptide of the invention that is non-toxic, or substantially non-toxic in cells in which it is expressed. In the absence of light, a light-activated ion channel of the invention does not significantly alter cell health or ongoing electrical activity in the cell in which it is expressed.

In some embodiments of the invention, a light-activated ion channel of the invention is genetically introduced into a cellular membrane, and reagents and methods are provided for genetically targeted expression of light-activated ion channel polypeptides, including ChR87. ChR88, ChR90, ChR62, ChR93. ChR88 K176R, or a derivative thereof, etc. Genetic targeting can be used to deliver light-activated ion channel polypeptides to specific cell types, to specific cell subtypes, to specific spatial regions within an organism, and to sub-cellular regions within a cell. Genetic targeting also relates to the control of the amount of light-activated ion channel polypeptide expressed, and the timing of the expression.

Some embodiments of the invention include a reagent for genetically targeted expression of a light-activated ion channel polypeptide, wherein the reagent comprises a vector that contains the gene for the light-activated ion channel polypeptide.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert light-activated ion channel polypeptides into dividing and non-dividing cells and can insert light-activated ion channel polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising the gene for a light-activated ion channel of the invention, such as ChR87, ChR88, ChR90, ChR62. ChR93, ChR88 K176R, or a derivative or variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a light-activated ion channel polypeptide in a wide variety of cell types—thus a promoter for a gene that is widely expressed in a variety of cell types, for example a "housekeeping gene" can be used to express a light-activated ion channel polypeptide in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER.

Methods of Use of Light Activated Ion Channels of the Invention

Light activated ion channels of the invention are well suited for targeting cells and specifically altering voltage-associated cell activities. In some embodiments of the invention, light-activated ion channels of the invention can utilized to introduce cations into cells, thus activating endogenous signaling pathways (such as calcium dependent signaling), and then drugs are applied that modulate the response of the cell (using a calcium or voltage-sensitive dye). This allows new kinds of drug screening using just light to activate the channels of interest, and using just light to read out the effects of a drug on the channels of interest.

Chrimson is far-red-activatable, and thus allows excitation of cells with a color of light heretofore not used in biotechnology for excitation of cells. By using for example, Chrimson and Chronos together, excitation of two different populations of cells in the same tissue or in the same culture dish becomes possible. This simultaneous, two-color excitation is particularly promising for complex tissues such as the brain.

The performance of the above said molecules or classes of molecules can be tuned for optimal use, particularly in context of their use in conjunction with other molecules or optical apparatus. Such tuning can be done using standard methods known in the art. For example, in order to achieve optimal contrast for multiple-color stimulation, one may desire to either improve or decrease the performance of one molecule with respect to one another, by the appendage of trafficking enhancing sequences or creation of genetic variants by site-directed mutagenesis, directed evolution, gene shuffling, or altering codon usage. Molecules or classes of molecules may have inherently varying spectral sensitivity that may be functionally advantageous in vivo (where scattering and absorption will vary with respect to wavelength, coherence, and polarization), by tuning the linearity or non-linearity of response to optical illumination with respect to time, power, and illumination history.

According to certain principles of this invention, cations may be introduced into cells, thus activating endogenous signaling pathways (such as calcium dependent signaling), and drugs may be applied that modulate the response of the cell (using a calcium or voltage-sensitive dye). This enables new kinds of drug screening using just light to activate the channels of interest, and using just light to read out the effects of a drug on the channels of interest.

Another aspect of the invention is the use of light-activated channel to decrease the pH of the cell. Such a technique may be used to treat alkalosis.

Another aspect of the invention may involve the use of light-activated proton pumps for the coupled effect of hyperpolarization and intracellular alkalinization. For example, both phenomena can induce spontaneous spiking in neurons by triggering hyperpolarization-induced cation currents or pH-dependent hyper-excitability.

Another aspect of the invention is to generate sub-cellular voltage or pH gradients, particularly at synapses and in synaptic vesicles to alter synaptic transmission, and mitochondria to improve ATP synthesis.

Another aspect of the invention is the use of far-red (660 nm) light to perform non-invasive transcranial and/or transdural stimulation to modulate neural circuits.

Another aspect of the invention is the various compositions of matter that have now been reduced to practice, for example: plasmids encoding for the above genes have been prepared; lentiviruses carrying payloads encoding for the above genes have been prepared; adeno-associated viruses carrying payloads encoding for the above genes have been prepared; cells expressing the above genes have been prepared; and animals expressing those genes have been prepared. (See for example: US Patent Publication 20110165681, incorporated herein by reference in its entirety).

Working operation of a prototype of this invention was demonstrated by genetically expressing light-activated ion channel molecules of the invention in excitable cells, illuminating the cells with suitable wavelengths of light, and demonstrating rapid depolarization of the cells in response to the light, as well as rapid release from depolarization upon cessation of light. Depending on the particular implementation, methods of the invention allow light control of cellular functions in vivo, ex vivo, and in vitro.

In non-limiting examples of methods of the invention, channelrhodopsins of the invention and derivatives thereof are used in mammalian cells without need for any kind of chemical supplement, and in normal cellular environmental conditions and ionic concentrations. For example, genes encoding channelrhodopsins of *Chlamydomonas* and *Stigeoclonium* have been used in exemplary implementations of the invention. These sequences in humanized or mouse-optimized form allow depolarization at wavelengths described herein.

As used herein, the term "ion channel" means a transmembrane polypeptide that forms a pore, which when activated opens, permitting ion conductance through the pore across the membrane. Many ion channels do not express well in a cell and/or their expression may be toxic to the cell and reduce cell health. Thus it was necessary to prepare and screen numerous channelrhodopsin light-activated ion channel polypeptides to identify light-activated ion channels of the invention that can be expressed in cells without significantly reducing cell health and viability.

Light-activated ion channels of the invention have been found to be suitable for expression and use in mammalian cells without need for any kind of chemical supplement, and in normal cellular environmental conditions and ionic concentrations. Light-activated ion channels of the invention have been found to differ from previously identified channels in that the Chronos light-activated ion channels activate at wavelengths of light ranging from 365 nm to 630 nm, with an optimal activation from light ranging from 430 nm to 550 nm, and a peak optimal activation at a wavelength of 500 nm. Chrimson light-activated ion channels activate at wavelengths of light in a range of 365 nm to 700 nm, with an optimal activation from light ranging from 530 nm to 640 nm, and a peak optimal activation at a wavelength of 590 nm.

Cells and Subjects

A cell used in methods and with sequences of the invention may be an excitable cell or a non-excitable cell. A cell in which a light-activated ion channel of the invention may be expressed and may be used in methods of the invention include prokaryotic and eukaryotic cells. Useful cells include but are not limited to mammalian cells. Examples of cells in which a light-activated ion channel of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, etc.).

Non-limiting examples of cells that may be used in methods of the invention include: neuronal cells, nervous system cells, cardiac cells, circulatory system cells, visual system cells, auditory system cells, secretory cells, endocrine cells, or muscle cells. In some embodiments, a cell used in conjunction with the invention may be a healthy normal cell, which is not known to have a disease, disorder or abnormal condition. In some embodiments, a cell used in conjunction with methods and channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Light-activated ion channels of the invention may be expressed in cells from culture, cells in solution, cells obtained from subjects, and/or cells in a subject (in vivo cells). Light-activated ion channels may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, rodent, fly or any other vertebrate or invertebrate organism.

Controls and Candidate Compound Testing

Light-activated ion channels of the invention and methods using light-activated ion channels of the invention can be utilized to assess changes in cells, tissues, and subjects in which they are expressed. Some embodiments of the invention include use of light-activated ion channels of the invention to identify effects of candidate compounds on cells, tissues, and subjects. Results of testing a light-activated ion channel of the invention can be advantageously compared to a control. In some embodiments of the invention one or more light-activated ion channels of the invention, non-limiting examples of which are ChR87, ChR88, ChR90, ChR93. ChR62, ChR88 K176R, or a derivative thereof, may be expressed in a cell population and used to test the effect of candidate compounds on the cells.

As used herein a control may be a predetermined value, which can take a variety of forms. It can be a single cut-off value, such as a median or mean. It can be established based upon comparative groups, such as cells or tissues that include the light-activated ion channel and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a light-activated ion channel to identify a candidate therapeutic agent or compound, a light-activated ion channel of the invention may be expressed in an excitable cell in culture or in a subject and the excitable cell may be contacted with a light that activates the light-activated ion channel and with a candidate therapeutic compound. In one embodiment, a test cell that includes a light-activated ion channel of the invention can be contacted with a light that depolarizes the cell and also contacted with a candidate compound. The cell, tissue, and/or subject that include the cell can be monitored for the presence or absence of a change that occurs in the test conditions versus the control conditions. For example, in a cell, a change may be a change in the depolarization or in a depolarization-mediated cell characteristic in the test cell versus a control cell, and a change in depolarization or the depolarization-mediated cell characteristic in the test cell compared to the control may indicate that the candidate compound has an effect on the test cell or tissue that includes the cell. In some embodiments of the invention, a depolarization-mediated cell characteristic may be a an action potential, pH change in a cell, release of a neurotransmitter, etc. and may in come embodiments, include a downstream effect on one or more additional cells, which occurs due to the depolarization of the cell that includes the light-activated ion channel. Art-known methods can be sued to assess depolarization and depolarization-mediated cell characteristics and changes to the depolarization or depolarization-mediated cell characteristics upon activation of a light-activated ion channel of the invention, with or without additional contact with a candidate compound.

Candidate-compound identification methods of the invention that are performed in a subject, may include expressing a light-activated ion channel in a subject, contacting the subject with a light under suitable conditions to activate the light-activated ion channel and depolarize the cell, and administering to the subject a candidate compound. The subject is then monitored to determine whether any change occurs that differs from a control effect in a subject. Thus, for example, a cell in culture can be contacted with a light appropriate to activate a light-activated ion channel of the invention in the presence of a candidate compound. A result of such contact with the candidate compound can be measured and compared to a control value as a determination of the presence or absence of an effect of the candidate compound.

Methods of identifying effects of candidate compounds using light-activated ion channels of the invention may also include additional steps and assays to further characterizing an identified change in the cell, tissue, or subject when the cell is contacted with the candidate compound. In some embodiments, testing in a cell, tissue, or subject can also include one or more cells that has a light-activated ion channel of the invention, and that also has one, two, three, or more additional different light-activated ion channels, wherein at least one, two, three, four, or more of the additional light-activated ion channels is activated by contact with light having a different wavelength than used to activate the Chronos, Chrimson, ChR87, or derivative thereof, light-activated ion channel of the invention.

In a non-limiting example of a candidate drug identification method of the invention, cells that include a light-activated ion channel of the invention are depolarized, thus triggering release of a neurotransmitter from the cell, and then drugs are applied that modulate the response of the cell to depolarization (determined for example using patch clamping methods or other suitable art-known means). Such methods enable new kinds of drug screening using just light to activate the channels of interest, and using just light to read out the effects of a drug on the channels and channel-containing cells of interest.

In some embodiments, light-activated ion channel polypeptides of the invention can be used in test systems and assays for assessing membrane protein trafficking and physiological function in heterologously expressed systems and the use of use of light-activated channels to depolarize a cell.

In some aspects of the invention, two-color assays can be performed. For example, Chronos (for blue light activation) and Chrimson (for red light activation) can be expressed in separate sets cells that represent non-overlapping neuronal populations. Following expression, the cell population can be exposed to light and the wavelength and timing and "dose" of light can be optimized. As used herein the term "dose" in reference to light, may take into account of wavelength, pulse length, intensity, of the light with which a light-activated ion channel of the invention is contacted.

A non-limiting example of a procedure for optimizing the use of two-color activated populations of cells is provided as follows. A population that has Chronos and Chrimson expressed in different sub-populations is contacted with blue light having a wavelength between 400 nm and 500 nm, or between 450 nm to 500 nm, and having a pulse width of between 1 and 5 ms for activation. A pulse width of 5 ms provides for minimum sub-threshold crosstalk in the blue light, which is defined as <15 mV, <10 mV, and optimally as <5 mV. The maximum blue light power that can be used is determined using by patch clamping Chrimson expressing cells, illuminating with blue light and measuring voltage deflection. Optimally using blue light power such that maximum voltage deflection is <10 mV, which in some embodiments may be 0.4 to 0.6 mW/mm$^2$. The optimal blue light power that can be used to drive Chronos is determined using the same conditions as above, except using lower light power, such as 50 µW/mm$^2$ to 0.4 mW/mm$^2$ which in some embodiments may be 0.2 mW/mm$^2$. Power depends on expression system and cell type used to prepare the population. The population can be contacted with red light having a wavelength between 600 nm and 700 nm, or 620 nm and 640 nm, and with a pulse width of between 1 and 5 ms for activation, which in some embodiments may be optimized at 5 ms. In certain embodiments of the invention, the optimal light power to drive Chrimson in the red may be determined by ramping light powers from for example, 0.1 mW/mm$^2$ to 100 mW/mm$^2$, or from 0.5 mW/mm$^2$ to 10 mW/mm$^2$. The method may be optimized such that a minimum red light power is used to achieve 100% spiking for Chrimson.

It will be understood that other sets of 2, 3, 4, or more light-activated ion channels may be expressed in separate subpopulations of a population of cells and then exposed to doses of light in a manner as described here to optimize their use in assays and treatments of the invention. A non-limiting example of a process to prepare and use a multi-light activated population of cells is as follows. A first light-activated ion channel is expressed in a first subpopulation of a population of cells; a second light-activated ion channel is expressed in a second subpopulation of the population of cells, wherein the first and second subpopulations are non-overlapping subpopulations, and the first light-activated ion channel and second light activated ion channel are have ranges of activating light wavelengths that do not entirely overlap. The population of cells is contacted with a plurality of first light test doses comprising combinations of wavelength, pulse width, and power that activate the first subpopulation, and the transmembrane voltage deflection is measured in a cell of the second subpopulation of cells contacted with the first light test doses. The first light test dose that includes a maximum light power that activates the light activated ion channel in first subpopulation of cells and results in a minimum sub-threshold transmembrane voltage deflection in the second subpopulation of cells is determined. The population of cells is then contacted with a plurality of first light test doses comprising a lower power than the maximum first light power that was determined, and a first light test doses that activate the first light activated ion channel (at the lower powers) are determined. The population of cells is then contacted with a plurality of second light test doses that include combinations of light wavelength, pulse width, and power that activate the second subpopulation, and a second light test dose comprising a second light power that activates the second subpopulation of cells is determined. Assays can be performed using such a population of cells, that includes contacting the population of cells with the first light test dose and the second light test dose determined using the steps above. The above-described process of optimizing light dose parameters for multi-light activated ion channels can be used to design and implement assays that include light-activated ion channels of the invention, as well as other light-activated ion channels that are known in the art.

Methods of Treating

Some aspects of the invention include methods of treating a disorder or condition in a cell, tissue, or subject using light-activated ion channels of the invention. Treatment methods of the invention may include administering to a subject in need of such treatment, a therapeutically effective amount of a light-activated ion channel of the invention to treat the disorder. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need to entirely eliminate the disease, disorder, or condition to be effective. In some embodiments of the invention one or more light-activated ion channels of the invention, non-limiting examples of which are ChR87, ChR88, ChR90, ChR93, ChR62 may be expressed in a cell population and used in methods to treat a disorder or condition.

Administration of a light-activated ion channel of the invention may include administration pharmaceutical composition that includes a cell, wherein the cell expresses the light-activated ion channel. Administration of a light-activated ion channel of the invention may include administration of a pharmaceutical composition that includes a vector, wherein the vector comprises a nucleic acid sequence encoding the light-activated ion channel and the administration of the vector results in expression of the light-activated ion channel in a cell in the subject.

An effective amount of a light-activated ion channel is an amount that increases the level of the light-activated ion channel in a cell, tissue or subject to a level that is beneficial for the subject. An effective amount may also be determined by assessing physiological effects of administration on a cell or subject, such as a decrease in symptoms following administration. Other assays will be known to one of ordinary skill in the art and can be employed for measuring the level of the response to a treatment. The amount of a treatment may be varied for example by increasing or decreasing the amount of the light-activated ion channel administered, by changing the therapeutic composition in which the light-activated ion channel is administered, by changing the route of administration, by changing the dosage timing, by changing the activation amounts and parameters of a light-activated ion channel of the invention, and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the light-activated ion channel is to be expressed. An effective amount may also depend on the location of the tissue to be treated.

Effective amounts will also depend, of course, on the particular condition being to treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition to increase the level of a light-activated ion channel, and/or to alter the length or timing of activation of a light-activated ion channel in a subject (alone or in combination with other therapeutic agents) be used, that is, the highest safe dose or amount according to sound medical judgment. It will be understood by those of ordinary skill in the art, however, that a patient may insist upon a lower dose or tolerable dose for medical reasons, psychological reasons or for virtually any other reasons.

A light-activated ion channel of the invention (for example, ChR87, ChR88, ChR90, ChR93, ChR62, or ChR88 K176R, or a derivative thereof) may be administered using art-known methods. In some embodiments a nucleic acid that encodes a light-activated ion channel polypeptide of the invention is administered to a subject and in certain embodiments a light-activated ion channel polypeptide is administered to a subject. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver light-activated ion channels of the invention may be administered alone, in combination with each other, and/or in combination with other drug therapies, or other treatment regimens that are administered to subjects. A pharmaceutical composition used in the foregoing methods preferably contain an effective amount of a therapeutic compound that will increase the level of a light-activated ion channel polypeptide to a level that produces the desired response in a unit of weight or volume suitable for administration to a subject.

The dose of a pharmaceutical composition that is administered to a subject to increase the level of light-activated ion channel in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a light-activated ion channel of the invention (e.g., light wavelength, length of light contact, etc.) that has been administered to a subject can also be adjusted based on efficacy of the treatment in a particular subject. Parameters for illumination and activation of light-activated ion channels that have been administered to a subject can be determined using art-known methods and without requiring undue experimentation.

Various modes of administration will be known to one of ordinary skill in the art that can be used to effectively deliver a pharmaceutical composition to increase the level of a light-activated ion channel of the invention in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase light-activated ion channel levels in a mammal other than a human; and administration and use of light-activated ion channels of the invention. e.g. for testing purposes or veterinary therapeutic purposes, is carried out under substantially the same conditions as described above. It will be understood by one of ordinary skill in the art that this invention is applicable to both human and animals. Thus this invention is intended to be used in husbandry and veterinary medicine as well as in human therapeutics.

In some aspects of the invention, methods of treatment using a light-activated ion channel of the invention are applied to cells including but not limited to a neuronal cell, a nervous system cell, a neuron, a cardiac cell, a circulatory system cell, a visual system cell, an auditory system cell, a muscle cell, or an endocrine cell, etc. Disorders and conditions that may be treated using methods of the invention include, injury, brain damage, degenerative neurological conditions (e.g., Parkinson's disease, Alzheimer's disease, seizure, vision loss, hearing loss, etc.

Disorders, Diseases and Conditions

Light-activated ion channels of the invention may be used to target cells and membranes, and to alter voltage-associated cell activities. In some aspects of the invention, a light-activated ion channel of the invention may be used to decrease the pH of a cell in which it is expressed. Such a technique may be used to treat alkalosis.

Another aspect of the invention includes methods of using light-activated proton pumps in conjunction with the use of light-activated ion channels of the invention for the coupled effect of hyperpolarization and intracellular alkalinization. For example, both phenomena can induce spontaneous spiking in neurons by triggering hyperpolarization-induced cation currents or pH-dependent hyper-excitability.

Another aspect of the invention is to express light-activated ion channels of the invention into cell membranes and then to activate the light-activated ion channels and generate sub-cellular voltage or pH gradients, particularly at synapses and in synaptic vesicles to alter synaptic transmission, and mitochondria to improve ATP synthesis.

In some embodiments, methods and light-activated ion channels of the invention may be used for the treatment of visual system disorders, for example to treat vision reduction or loss. A light-activated ion channel of the invention may be administered to a subject who has a vision reduction or loss and the expressed light-activated ion channel can function as light-sensitive cells in the visual system, thereby permitting a gain of visual function in the subject.

The present invention in some aspects, includes preparing nucleic acid sequences and polynucleotide sequences; expressing in cells and membranes polypeptides encoded by the prepared nucleic acid and polynucleotide sequences; illuminating the cells and/or membranes with suitable light, and demonstrating rapid depolarization of the cells and/or a change in conductance across the membrane in response to light, as well as rapid release from depolarization upon cessation of light. The ability to controllably alter voltage across membranes and cell depolarization with light has been demonstrated. The present invention enables light-control of cellular functions in vivo, ex vivo, and in vitro, and the light activated ion channels of the invention and their use, have broad-ranging applications for drug screening, treatments, and research applications, some of which are describe herein.

In illustrative implementations of this invention, the ability to optically perturb, modify, or control cellular function offers many advantages over physical manipulation mechanisms. These advantages comprise speed, non-invasiveness, and the ability to easily span vast spatial scales from the nanoscale to macroscale.

The reagents use in the present invention (and the class of molecules that they represent), allow, at least: currents activated by light wavelengths not useful in previous light-activated ion channels, light activated ion channels that when activated, permit effectively zero calcium conductance, and different spectra from older molecules (opening up multi-color control of cells).

EXAMPLES

Example 1

Studies were performed to prepare sequences and to express light-activated ion channels in cells, tissues, and subjects. Identifications and amino acid sequences of some of the light-activated ion channels in the examples are ChR88 (SEQ ID NO:2); ChR90 (SEQ ID NO:7); ChR87 (SEQ ID NO:11); ChR62 (SEQ ID NO:14), ChR93 (SEQ ID NO:16) and ChR2 (SEQ ID NO:19), ChR88 K176R (SEQ ID NO:5). Non-limiting exemplary methods are set forth Example 1. General methods also applicable to light-activated channel molecules and methods for their use are disclosed in publications such as US Published Application No. 2010/0234273, US Published Application No. 20110165681, Chow B Y, et. al. *Methods Enzmymol.* 2011; 497:425-43; Chow, B Y, et al. *Nature* 2010 Jan. 7; 463 (7277):98-102, the content of each of which is incorporated by reference herein.

Studies were performed to prepare sequences and to express light-activated ion channels in cells, tissues, and subjects. Non-limiting exemplary methods are set forth below.

(a) In Utero Electroporation

All procedures were in accordance with the National Institutes of Health Guide for the Care and Use of Laboratory Animals and approved by the Massachusetts Institute of Technology Committee on Animal Care. C57BL/6J E16-timed pregnant mice were used for electroporation. Surgery was done under ketamine-xylazine anesthesia and buprenorphine analgesia, DNA solution containing plasmids of interest were injected into lateral ventricle of each embryo using a pulled capillary tube. Five square pulses (50 ms width, 1 Hz, 35V) were applied using tweezer electrode for electroporation.

(b) Slice Preparation

P20-P30 mice were used for slice preparation. In younger animals it was difficult to elicit synaptic responses by photostimulating callosal axons. Mice were anesthetized with isofluorane and transcardialy perfused with artificial cerebrospinal fluid (ACSF). The brain was removed and placed in an ice-cold cutting solution containing 110 mM choline chloride, 25 mM $NaHCO_3$, 25 mM D-glucose, 11.6 mM sodium ascorbate, 7 mM $MgCl_2$, 3.1 mM sodium pyruvate, 2.5 mM KCl, 1.25 mM $NaH_2PO_4$ and 0.5 mM $CaCl_2$. 300-mm-thick coronal slices of the visual cortex were cut with a vibrating slicer and incubated in oxygenated ACSF for 45 min at 37° C. before the recordings.

(c) Slice Electrophysiology

Recordings were performed at room temperature (22-24° C.) under constant perfusion of oxygenated ACSF. Neurons were visualized using infrared differential interference optics and patched with borosilicate pipettes (resistance 4-6 MO). The intracellular solution contained 120 mM potassium gluconate, 5 mM NaCl, 2 mM $MgCl_2$, 0.1 mM $CaCl_2$, 10 mM HEPES, 1.1 mM EGTA, 4 mM magnesium ATP, 0.4 mM disodium GTP, (pH 7.25; 290 mOsm). Cells were recorded at a depth of 30-120 um in the brain slice. Photostimulation was done using a blue LED (470 nm; Thorlabs. Newton, N.J.) and a red LED (625 nm with 632/22 nm filter; Thorlabs).

(d) Neuron Culture, Transfection, Infection, and Imaging

All procedures involving animals were in accordance with the National Institutes of Health Guide for the care and use of laboratory animals and approved by the Massachusetts Institute of Technology Animal Care and Use Committee. Swiss Webster or C57 mice [Taconic (Hudson, N.Y.) or Jackson Labs (Bar Harbor, Me.)] were used. For hippocampal cultures, hippocampal regions of postnatal day 0 or day 1 mice were isolated and digested with trypsin (1 mg/ml) for ~12 min, and then treated with Hanks solution supplemented with 10-20% fetal bovine serum and trypsin inhibitor (Sigma Aldrich, St Louis, Mo.). Tissue was then mechanically dissociated with Pasteur pipettes, and centrifuged at 1000 rpm at 4° C. for 10 min. Dissociated neurons were plated at a density of approximately four hippocampi per 20 glass coverslips, coated with Matrigel (BD Biosciences, San Jose, Calif.). For cortical cultures, dissociated mouse cortical neurons (postnatal day 0 or 1) were prepared as previously described, and plated at a density of 100-200 k per glass coverslip coated with Matrigel (BD Biosciences). Cultures were maintained in Neurobasal Medium supplemented with B27 (Invitrogen [Life Technologies, Grand Isle, N.Y.]) and glutamine. Hippocampal and cortical cultures were used interchangeably; no differences in reagent performance were noted.

Neurons were transfected at 3-5 days in vitro using calcium phosphate (Invitrogen). GFP fluorescence was used to identify successfully transfected neurons. Alternatively, neurons were infected with 0.1-3 µl of lentivirus or adeno-associated virus (AAV) per well at 3-5 days in vitro.

(e) HEK 293FT Cell Culture and Transfection

HEK 293FT cells (Invitrogen) were maintained between 10-70% confluence in D10 medium (Cellgro [Mediatech/Corning, Manassas, Va.]) supplemented with 10% fetal bovine serum (Invitrogen), 1% penicillin/streptomycin (Cellgro), and 1% sodium pyruvate (Biowhittaker, Walkersville, Md.). For recording, cells were plated at 5-20% confluence on glass coverslips coated with Matrigel (BD Biosciences). Adherent cells were transfected approximately 24 hours post-plating either with TransLT 293 lipofectamine transfection kits (Mirus Bio, LLC, Madison, Wis.) or with calcium phosphate transfection kits (Invitrogen), and recorded via whole-cell patch clamp between 36-72 hours post-transfection.

(f) In Vitro Whole Cell Patch Clamp Recording & Optical Stimulation

Whole cell patch clamp recordings were made using a Multiclamp 700B amplifier, a Digidata 1440 digitizer, and a PC running pClamp (Molecular Devices). Neurons were bathed in room temperature Tyrode containing 125 mM NaCl, 2 mM KCl, 3 mM $CaCl_2$, 1 mM $MgCl_2$, 10 mM HEPES, 30 mM glucose, 0.01 mM NBQX and 0.01 mM GABAzine. The Tyrode pH was adjusted to 7.3 with NaOH and the osmolarity was adjusted to 300 mOsm with sucrose. HEK cells were bathed in a Tyrode bath solution identical to that for neurons, but lacking GABAzine and NBQX. Borosilicate glass pipettes (Warner Instruments, Hamden, Conn.) with an outer diameter of 1.2 mm and a wall thickness of 0.255 mm were pulled to a resistance of 3-9 MS with a P-97 Flaming/Brown micropipette puller (Sutter Instruments, Novato, Calif.) and filled with a solution containing 125 mM K-gluconate, 8 mM NaCl, 0.1 mM $CaCl_2$, 0.6 mM $MgCl_2$, 1 mM EGTA, 10 mM HEPES, 4 mM Mg-ATP, and 0.4 mM Na-GTP. The pipette solution pH was adjusted to 7.3 with KOH and the osmolarity was adjusted to 298 mOsm with sucrose. Access resistance was 5-30 MΩ, monitored throughout the voltage-clamp recording. Resting membrane potential was ~−60 mV for neurons and ~−30 mV for HEK 293FT cells in current-clamp recording.

Photocurrents were measured with 500 ms light pulses in neurons voltage-clamped at −60 mV, and in HEK 293FT cells voltage-clamped at −30 mV. Light-induced membrane hyperpolarizations were measured with 500 ms light pulses in cells current-clamped at their resting membrane potential. Light pulses for all wavelengths except 660 nm and action spectrum characterization experiments were delivered with a DG-4 optical switch with 300 W xenon lamp (Sutter Instruments), controlled via TTL pulses generated through a Digidata signal generator. Green light was delivered with a 575-25 nm bandpass filter (Chroma) and a 575±7.5 nm bandpass filter (Chroma Technology Group, Bellows Falls, Vt.). Action spectra were taken with a Till Photonics Polychrome V, 150 W Xenon lamp, 15 nm monochromator bandwidth.

Data was analyzed using Clampfit (Molecular Devices) and MATLAB (Mathworks, Inc.)

(g) Ion Conductance Recording

Whole-cell patch clamp recordings were performed in isolated HEK293FT cells to accurately measure parameters from single cells. All recordings were performed using an Axopatch 200B amplifier and Digidata 1440 digitizer (Molecular Devices) at room temperature. In order to allow isolated cell recording, cells were plated at a lower density of 15,000 cells per well in 24-well plates that contained round glass coverslips (0.15 mm thick, 25 mm in diameter, coated with 2% Growth Factor Reduced Matrigel in DMEM for 1 h at 37° C.). For most recordings, Tyrode was used as the extracellular solution, and the intracellular solution consisted of (in mM) 125 K-Gluconate, 8 NaCl, 0.1 $CaCl_2$, 0.6 $MgCl_2$, 1 EGTA, 10 HEPES, 4 MgATP, 0.4 NaGTP, pH 7.3 (KOH adjusted), with 295-300 mOsm (sucrose adjusted). Extracellular and intracellular solutions used for testing ion permeability are listed in Table 1.

TABLE 1

Compositions of solutions used in ion permeability experiments

| Solution | [Na] (mM) | [K] (mM) | [Ca] (mM) | [H] (mM) | pH | Other |
|---|---|---|---|---|---|---|
| Intracellular | 0 | 140 | 0 | 5.10E−05 | 7.4 | 5 mM EGTA, 2 mM MgCl2, 10 mM HEPES |
| 145 mM NaCl | 145 | 5 | 1 | 5.10E−05 | 7.4 | 1.0 mM HEPES, 5 mM glucose, 2 mM MgCl2 |
| 145 mM KCl | 0 | 145 | 1 | 5.10E−05 | 7.4 | 10 mM HEPES, 5 mM glucose, 2 mM MgCl2 |
| 90 mM CaCl$_2$ | 0 | 5 | 91 | 5.10E−05 | 7.4 | 10 mM HEPES, 5 mM glucose, 2 mM MgCl2 |
| 5 mM NaCl | 5 | 5 | 1 | 5.10E−04 | 6.4 | 135 mM NMDG, 10 mM HEPES, 5 mM glucose, 2 mM MgCl2 |

Liquid junction potentials were measured using standard procedures to be 5.8 mV for the 90 mM CaCl$_2$ and 4.9 mV for the 5 mM NaCl extracellular solutions, which were corrected during recording; the others were <1 mV in junction potential.

In all patch clamp recordings, a stringent cutoff of access resistance less than 25 MΩ and holding current less than ±50 pA was applied in order to ensure accurate measurement. Typical membrane resistance was between 500 MΩ-2 GΩ and pipette resistance was between 4-10 MΩ.

Photostimulation of patch clamped cells was conducted by a 470 nm LED (Thorlabs) at 10 mW/mm$^2$ unless otherwise stated. For most experiments, 1 s illumination was delivered to measure transient and steady-state photocurrents.

(h) Plasmid Construction and Site Directed Mutagenesis.

Opsins were mammalian codon-optimized, and synthesized by Genscript (Genscript Corp., NJ). Opsins were fused in frame, without stop codons, ahead of GFP (using BamHI and AgeI) in a lentiviral vector containing the CaMKII promoter, enabling direct neuron transfection, HEK cell transfection (expression in HEK cells is enabled by a ubiquitous promoter upstream of the lentiviral cassette), and lentivirus production and transfection. Amino acid sequences of some opsins that were tested were as follows: ChR88 (SEQ ID NO:2); ChR90 (SEQ ID NO:7); ChR87 (SEQ ID NO: 11); ChR62 (SEQ ID NO:14), ChR93 (SEQ ID NO: 16) and ChR2 (SEQ ID NO:19), ChR88 K176R (SEQ ID NO:5).

The 'ss' signal sequence from truncated MHC class I antigen corresponded to amino acid sequence (M)VPCTLLLLLAAALAPTQTRA (SEQ ID NO:21), DNA sequence gtcccgtgcacgctgctcctgctgttggcagccgccctggctccgactcagacgcgggcc (SEQ ID NO:20). The 'ER2' ER export sequence corresponded to amino acid sequence FCYENEV (SEQ ID NO:23), DNA sequence ttctgctacgagaatgaagtg (SEQ ID NO:22). The 'KGC' signal sequence corresponded to amino acid sequence KSRITSEGEYIPLDQIDINV (SEQ ID NO:25), DNA sequence of KGC signal sequence: aaatccagaattacttctgaaggggagtatatccctctggatcaaatagacatcaatgtt. (SEQ ID NO:24).

Point mutants for HEK cell testing were generated using the QuikChange kit [Stratagene, (Agilent Technologies, Santa Clara, Calif.)] on the opsin-GFP fusion gene inserted between BamHI and AgeI sites in a modified version of the pEGFP—N3 backbone [Invitrogen, (Life Technologies Corporation, Carlsbad, Calif.)]. All constructs were verified by sequencing.

(i) Lentivirus Preparation

HEK293FT cells [Invitrogen, (Life Technologies Corporation, Carlsbad, Calif.)] were transfected with the lentiviral plasmid, the viral helper plasmid pΔ8.74, and the pseudotyping plasmid pMD2.G. The supernatant of transfected HEK cells containing virus was then collected 48 hours after transfection, purified, and then pelleted through ultracentrifugation. Lentivirus pellet was resuspended in phosphate buffered saline (PBS) and stored at −80° C. until further usage in vitro or in vivo. The estimated final titer is approximately $10^9$ infectious units/mL.

Example 2

Figure 1B:
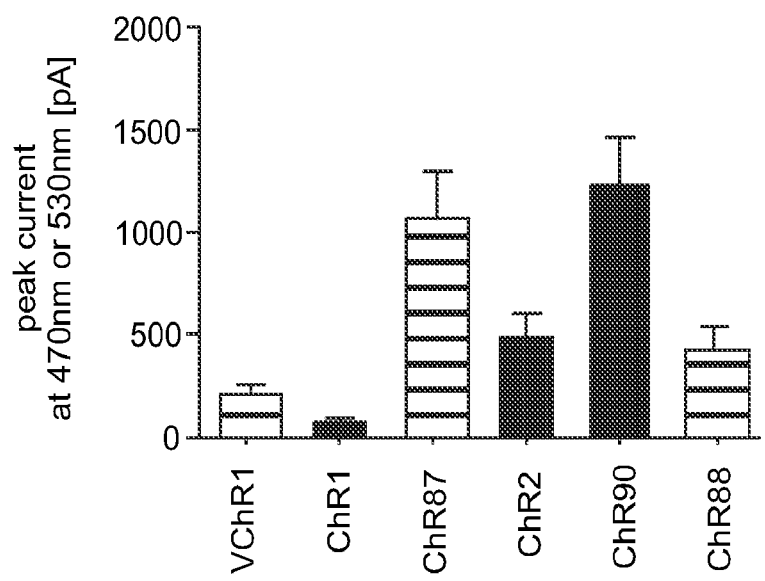
FIG. 1B shows results using blue (4.23 mW mm⁻²) or green (3.66 mW mm⁻²) light peak photocurrent at equal photon flux for 5 ms illumination. ChR87, ChR88, and ChR90 all have greater or comparable photocurrent than ChR2. Solid bar indicates blue light, horizontal striped bar indicates green light.

Light-activated ion channels VChR1, ChR1, ChR2, ChR87, ChR90, and ChR88 were expressed in cultured hippocampal neurons using neuron culture, transfection, infection, and imaging methods described in Example 1. In vitro whole cell patch claim recording and optical stimulation were conducted on the neurons using methods described in Example 1. FIG. 1 shows channelrhodopsin photocurrents measured in the cultured hippocampal neurons. FIG. 1A shows results using red light (660 nm) peak photocurrent at 10 mW mm$^{-2}$ for 1 s illumination. ChR88 is the only red light sensitive channelrhodopsin with significant photocurrent at 660 nm. FIG. 1B shows results using blue (4.23 mW mm$^{-2}$) or green (3.66 mW mm$^{-2}$) light peak photocurrent at equal photon flux for 5 ms illumination. ChR87, ChR88, and ChR90 all have greater or comparable photocurrent than ChR2. Solid bar indicates blue light, horizontal striped bar indicates green light.

Example 3

Figure 2:
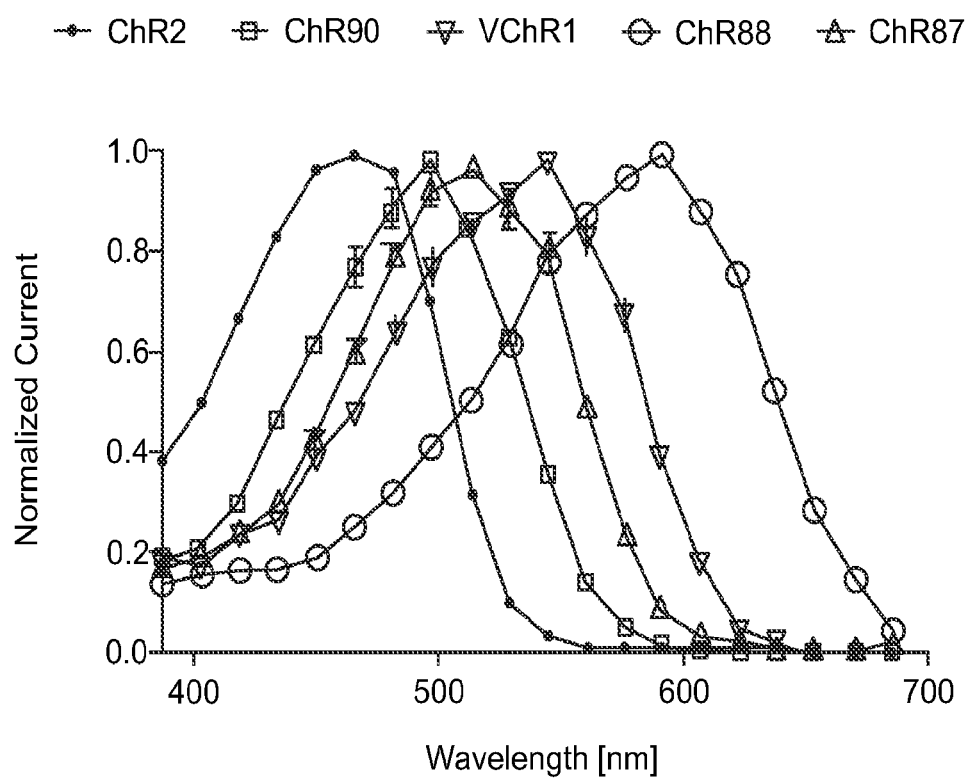
FIG. 2 is a graph showing action spectrum at equal photon dose at all wavelengths recorded in HEK293FT cells. ChR2 (470 nm peak) and VChR1 (545 nm peak) represent the existing channelrhodopsin color sensitivity range. ChR87 (515 nm peak) and ChR90 (500 nm peak) are blue green light sensitive channelrhodopsins. Whereas ChR88 (590 nm peak) is the first red light sensitive natural channelrhodopsin.

HEK 293FT cells were transfected to express ChR2, ChR90, VChR1, ChR88, and ChR87 light-activated ion channels using methods of Example 1. In vitro whole cell patch claim recording and optical stimulation were conducted on the transfected, cultured cells using methods described in Example 1. FIG. 2 show action spectrum at equal photon dose at all wavelengths recorded in HEK293FT cells. ChR2 (470 nm peak) and VChR1 (545 nm peak) represent the existing channelrhodopsin color sensitivity range. ChR87 (515 nm peak) and ChR90 (500 nm peak) are blue green light sensitive channelrhodopsins. Whereas ChR88 (590 nm peak) is the first red light sensitive natural channelrhodopsin.

Example 4

Figures 3A, 3B:
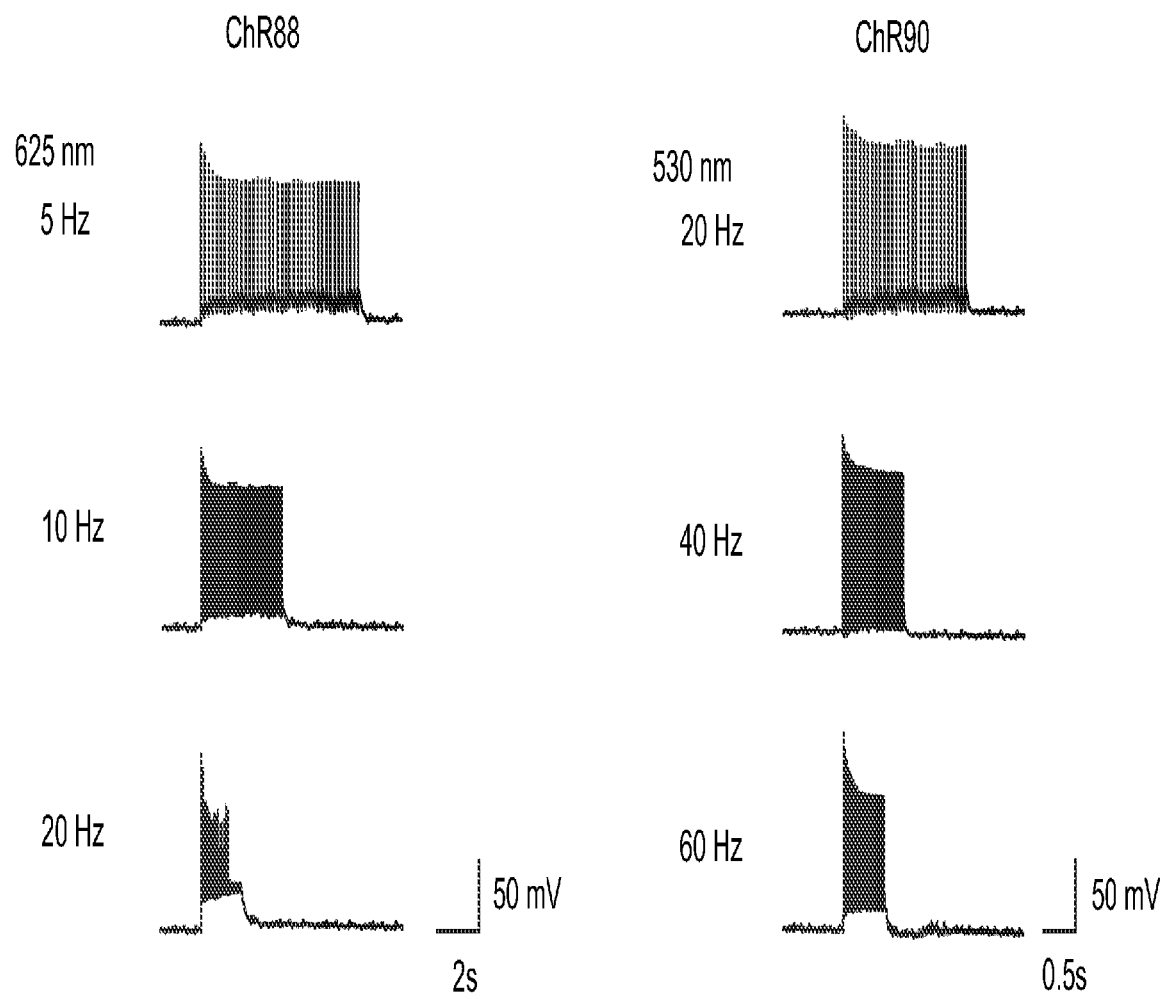
FIG. 3A shows red-light-driven spike trains at low frequency for Ch88. Generally ChR88 can reliably drive spikes up to 5 Hz. However at higher frequency such as 20 Hz, ChR88 desensitizes and/or causes depolarization block.
FIG. 3B shows green-light-driven spike trains at high frequency for Ch90. Due to ChR90 fast tau off and peak photocurrent recovery kinetics, it is able to drive temporally precise spikes at the highest frequency a neuron is capable of mediating.

Light-activated ion channels ChR90 and ChR88 were expressed in cultured hippocampal neurons using neuron culture, transfection, infection, and imaging methods described in Example 1. In vitro whole cell patch claim recording and optical stimulation were conducted on the neurons using methods described in Example 1. FIG. 3 shows optically-driven spikes in the cultured hippocampal neurons. FIG. 3A shows red-light-driven spike trains at low frequency for Ch88. Generally ChR88 could reliably drive spikes up to 5 Hz. However at higher frequency such as 20 Hz, ChR88 desensitizes and/or causes depolarization block. FIG. 3B shows green-light-driven spike trains at high frequency for Ch90. Due to ChR90 fast tau off and peak photocurrent recovery kinetics, it was able to drive temporally precise spikes at the highest frequency a neuron is capable of mediating.

Example 5

Figure 4A:
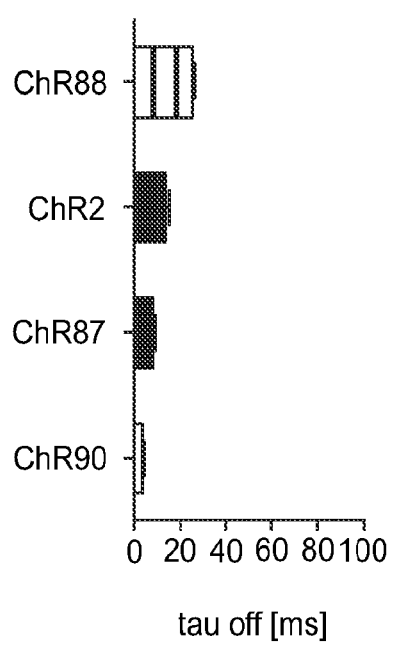
FIG. 4A shows single exponential channel turn-off kinetics based on 5 ms pulse. ChR90 has the fastest turn-off kinetics (3.5 ms) observed across all natural channelrhodopsins.
Figure 4B:
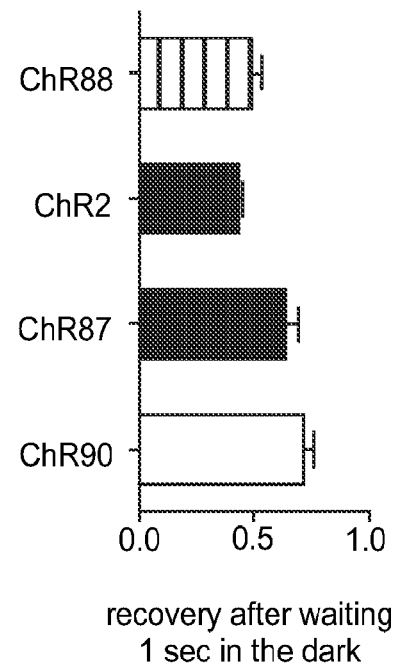
FIG. 4B shows peak photocurrent recovery ratio based on is illumination. ChR87 and ChR90 both have fast peak photocurrent recovery at around 70%. However ChR88 has slow recovery kinetics similar to ChR2.

Light-activated ion channels ChR88, Chr2, ChR87, and ChR90 were expressed in cultured hippocampal neurons using neuron culture, transfection, infection, and imaging methods described in Example 1. In vitro whole cell patch claim recording and optical stimulation were conducted on the neurons using methods described in Example 1. FIG. 4 illustrates the results and shows channelrhodopsin kinetics measured in the hippocampal neuron culture voltage clamped at −65 mV. FIG. 4A shows single exponential channel turn-off kinetics based on 5 ms pulse. ChR90 had the fastest turn-offkinetics (3.5 ms) observed across all natural channelrhodopsins. FIG. 4B showed peak photocurrent recovery ratio based on 1 s illumination. ChR87 and ChR90 both had fast peak photocurrent recovery at around 70%. However ChR88 had slow recovery kinetics similar to ChR2.

Example 6

Figures 5A, 5B:
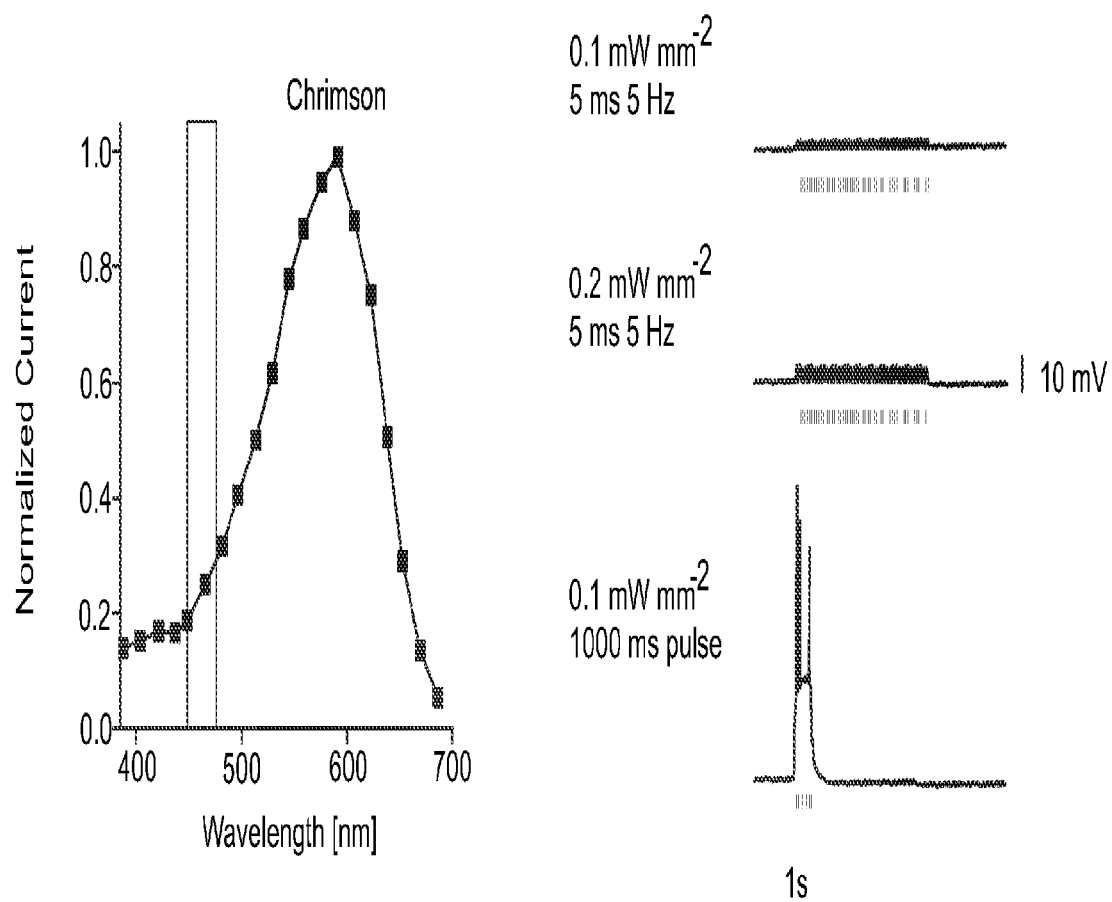
FIG. 5A shows action spectrum of Chrimson and the blue light (470 nm) wavelength used for illumination. Wavelength was chosen to minimize crosstalk.
FIG. 5B provides representative traces from a single neuron at various illumination conditions. When the blue light power is doubled from 0.1 to 0.2 mW mm⁻² while the stimulation protocol is fixed as 5 ms 5 Hz, the voltage deflection is also doubled. However when the blue light power is fixed at 0.1 mW mm⁻² but the pulse duration is changed from 5 ms to 1000 ms, the crosstalk is changed from <5 mV to full spiking correspondingly. This means blue light crosstalk is a function of both light power and light pulse duration (total photon count).

Light-activated ion channels Chrimson (ChR88) were expressed in cultured hippocampal neurons using neuron culture, transfection, infection, and imaging methods described in Example 1. In vitro whole cell patch claim recording and optical stimulation were conducted on the neurons using methods described in Example 1. FIG. 5 shows Chrimson blue light crosstalk characterization in cultured neurons. FIG. 5A shows action spectrum of Chrimson and the blue light (470 nm) wavelength used for illumination. Wavelength was chosen to minimize crosstalk. FIG. 5B shows representative traces from a single neuron at various illumination conditions. When the blue light power was doubled from 0.1 to 0.2 mW mm$^{-2}$ while the stimulation protocol was fixed as 5 ms 5 Hz, the voltage deflection was also doubled. However when the blue light power was fixed at 0.1 mW mm$^{-2}$ but the pulse duration was changed from 5 ms to 1000 ms, the crosstalk was changed from <5 mV to full spiking correspondingly. This means blue light crosstalk was a function of both light power and light pulse duration (total photon count).

Example 7

Figure 6A:
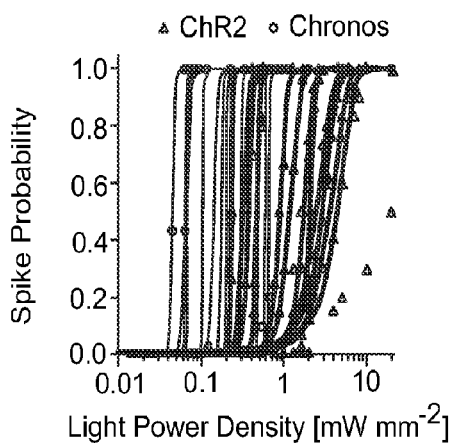
FIG. 6A is a spike irradiance curve for individual neurons.
Figure 6C:
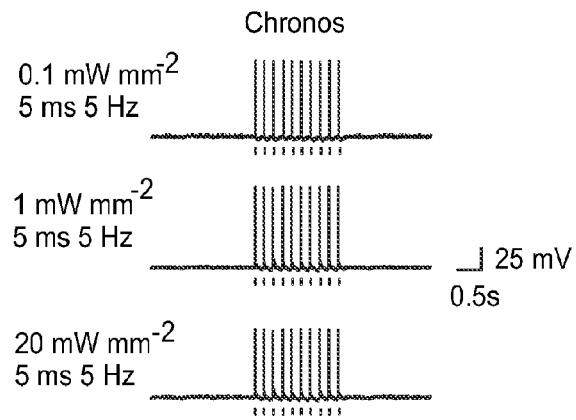
FIG. 6C provides example traces of Chronos spiking at various light powers.
Figure 6B:
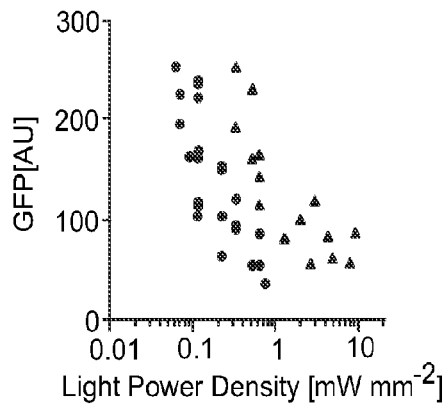
FIG. 6B shows lowest light power needed for single-cell 100% spike probability vs GFP fluorescence. Chronos (circles) is approximately 5 times more light sensitive than ChR2 (triangles) at a given (GFP) expression level.
Figure 6D:
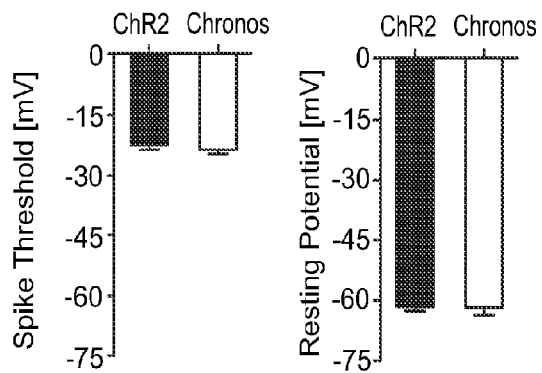
FIG. 6D illustrates that controls shows no significant electrical differences between ChR2 and Chronos expressing neurons.

Light-activated ion channels Chronos (ChR90) and ChR2 were expressed in cultured hippocampal neurons using neuron culture, transfection, infection, and imaging methods described in Example 1. In vitro whole cell patch claim recording and optical stimulation were conducted on the neurons using methods described in Example 1. FIG. 6 illustrates Chronos and ChR2 blue light sensitivity in cultured hippocampal neurons. FIG. 6A is a spike irradiance curve for individual neurons. FIG. 6B shows lowest light power needed for single-cell 100% spike probability vs GFP fluorescence. Chronos (circles) was approximately 5 times more light sensitive than ChR2 (triangles) at a given (GFP) expression level. FIG. 6C shows example traces of Chronos spiking at various light powers. FIG. 6D illustrates that controls showed no significant electrical differences between ChR2 and Chronos expressing neurons.

Example 8

Figure 7A:
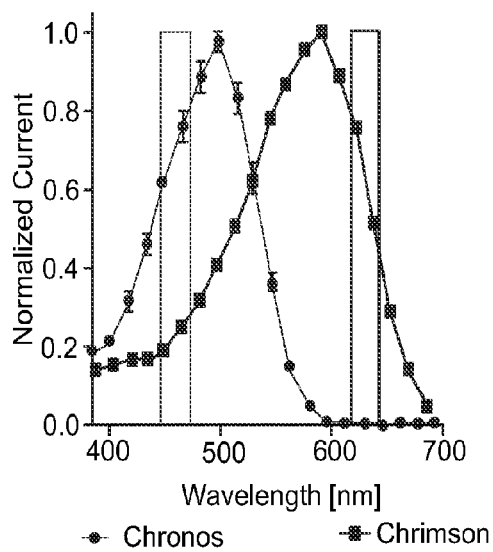
FIG. 7A shows illumination wavelength used for slice experiments.
Figure 7B:
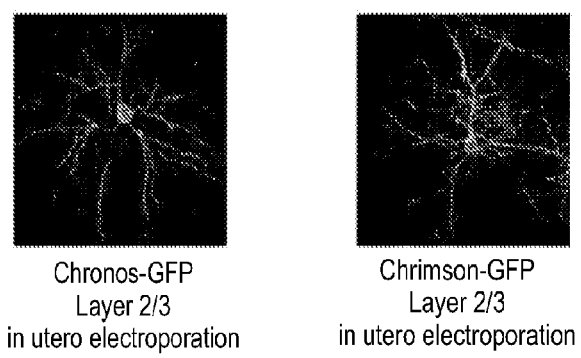
FIG. 7B is micrographic images showing histology for Chronos and Chrimson GFP fusion construct singly expressed in layer 2/3 visual cortex in mice.

In utero electroporation and slice preparation methods as described in Example 1 were used to examine Chronos (ChR90) and Chrimson (ChR88) activation. FIG. 7 illustrates the strategy used for slice characterization of Chronos and Chrimson. FIG. 7A shows illumination wavelength used for slice experiments. FIG. 7B provides micrographic images showing histology for Chronos and Chrimson GFP fusion construct singly expressed in layer 2/3 visual cortex in mice.

Example 9

Figure 8A:
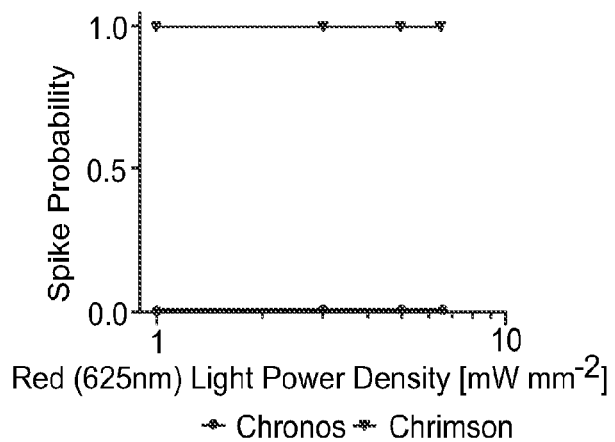
FIG. 8A illustrates that red light elicits 100% spiking in Chrimson expressing neurons but not Chronos expressing neurons between 1-6.5 mW mm⁻².
Figure 8B:
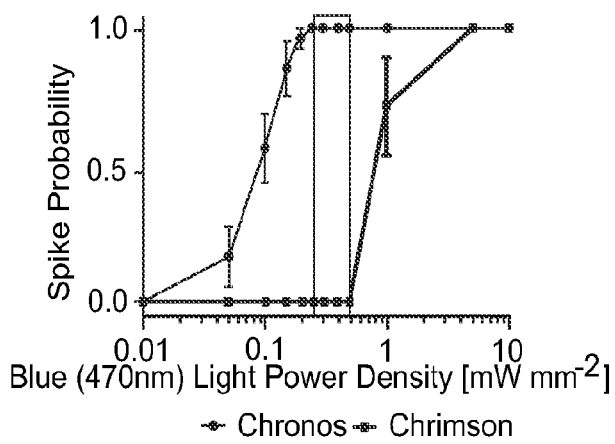
FIG. 8B shows that blue light at 0.2-0.5 mW mm⁻² can elicit 100% spiking in Chronos expressing cells but not Chrimson expressing cells. However full spiking crosstalk in Chrimson expressing cells can occur at powers higher than 0.6 mW mm$^{-2}$.
Figure 8C:
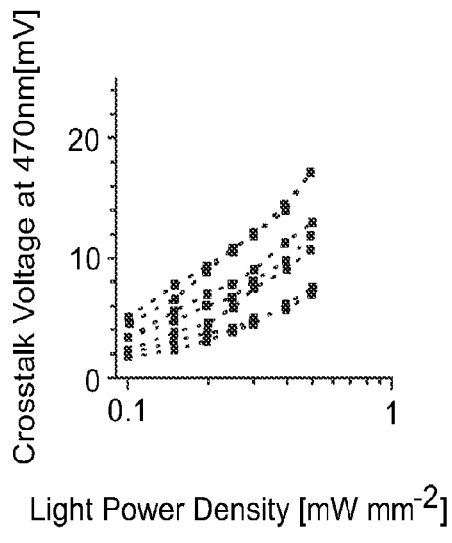
FIG. 8C shows blue light crosstalk voltage of Chrimson expressing neurons.

In ulero electroporation, slice preparation, and slice electrophysiology methods as described in Example 1 were used to characterize Chrimson (ChR88) and Chronos (ChR90) blue and red light sensitivity in slice preparations. FIG. 8 illustrates results obtained using whole cell patch clamp methods. FIG. 8A shows that red light elicited 100% spiking in Chrimson expressing neurons but not Chronos expressing neurons between 1-6.5 mW mm$^{-2}$. FIG. 8B shows that blue light at 0.2-0.5 mW mm$^{-2}$ could elicit 100% spiking in Chronos expressing cells but not Chrimson expressing cells. However full spiking crosstalk in Chrimson expressing cells can occur at powers higher than 0.6 mW mm$^{-2}$. FIG. 8C shows blue light crosstalk voltage of Chrimson expressing neurons.

Example 10

Figure 9:
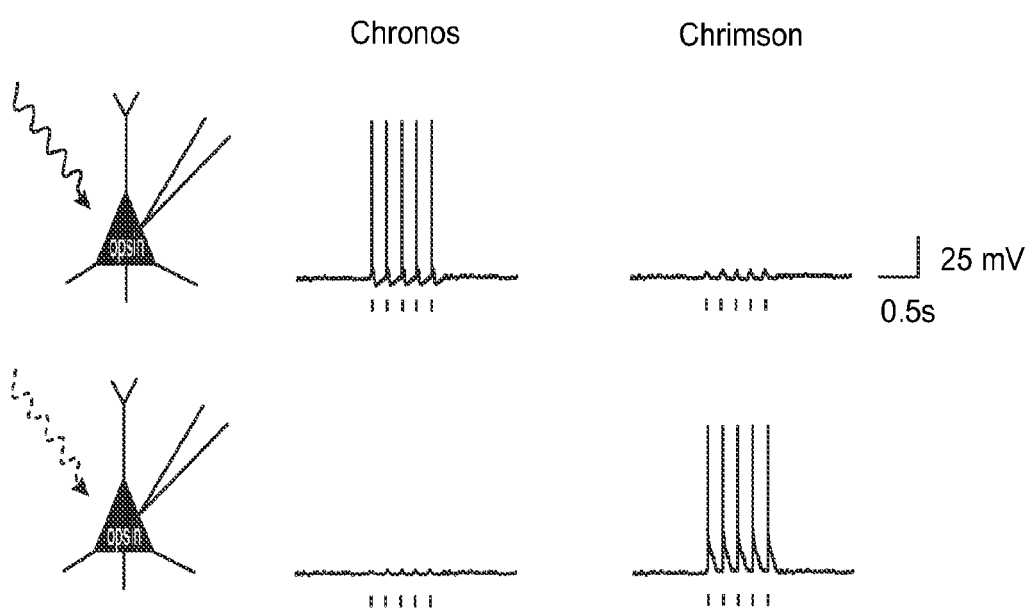
FIG. 9 provides example traces of current-clamped opsin-expressing neurons in layer 2/3 slice blue light 0.1 mW mm$^{-2}$, red light 1 mW mm$^{-2}$ expressing. No crosstalk was observed under red light for Chronos while minimal sub-threshold (<5 mV) crosstalk was observed under blue light for Chrimson.

In utero electroporation, slice preparation, and slice electrophysiology methods as described in Example 1 were used to characterize Chrimson (ChR88) and Chronos (ChR90). FIG. 9 illustrates results with example traces of current-clamped opsin-expressing neurons in layer 2/3 slice blue light 0.1 mW mm$^{-2}$, red light 1 mW mm$^{-2}$ expressing. No crosstalk was observed under red light for Chronos while minimal subthreshold (<5 mV) crosstalk was observed under blue light for Chrimson.

Figure 10:
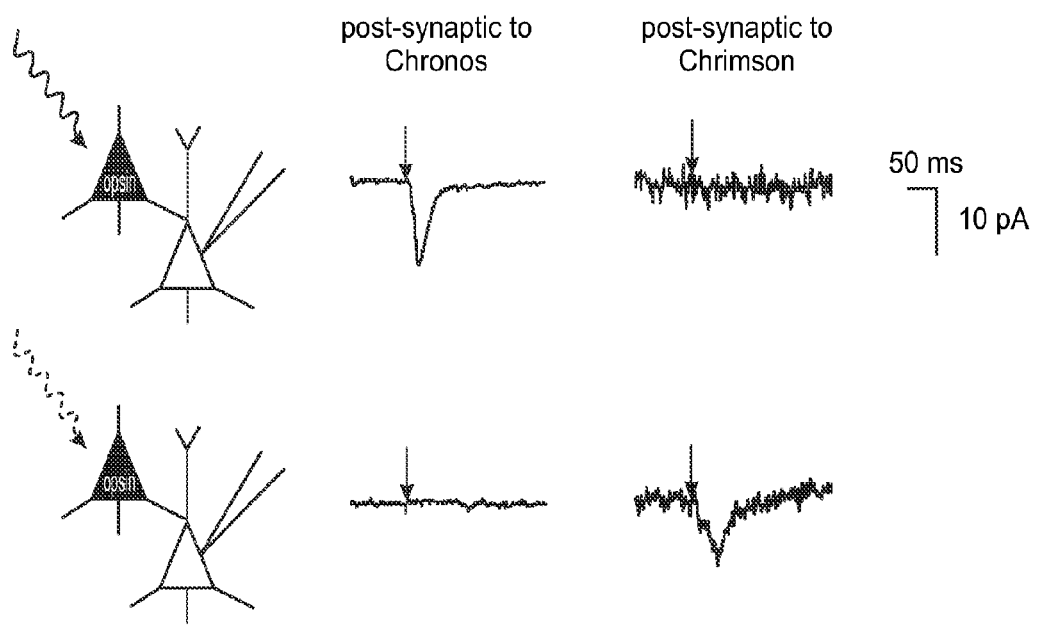
FIG. 10 provides example traces of voltage-clamped non-opsin-expressing neurons in layer 2/3 or 5, post-synaptic to opsin-expressing cells. Zero post-synaptic crosstalk was observed for both Chronos and Chrimson under red and blue light illumination respectively.
Chronos: blue light 0.13 mW mm$^{-2}$, red light 1.7 mW mm$^{-2}$.
Chrimson: blue light 0.37 mW mm$^{-2}$, red light 1.7 mW mm$^{-2}$.

FIG. 10 illustrates results with example traces of voltage-clamped non-opsin-expressing neurons in layer 2/3 or 5, post-synaptic to opsin-expressing cells. Zero post-synaptic crosstalk was observed for both Chronos and Chrimson under red and blue light illumination respectively. Chronos: blue light 0.13 mW mm$^{-2}$, red light 1.7 mW mm$^{-2}$. Chrimson: blue light 0.37 mW mm$^{-2}$, red light 1.7 mW mm$^{-2}$.

Figure 11A:
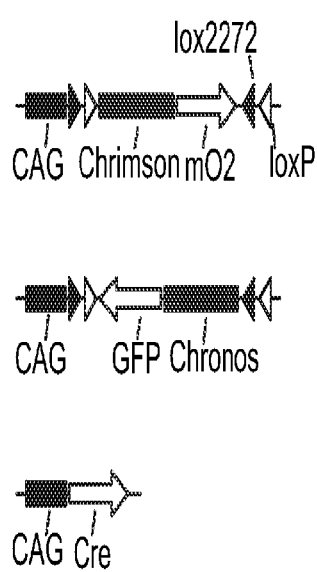
FIG. 11A shows a triple plasmid in utero electroporation scheme to obtain non-overlapping expression of Chrimson and Chronos.
Figure 11B:
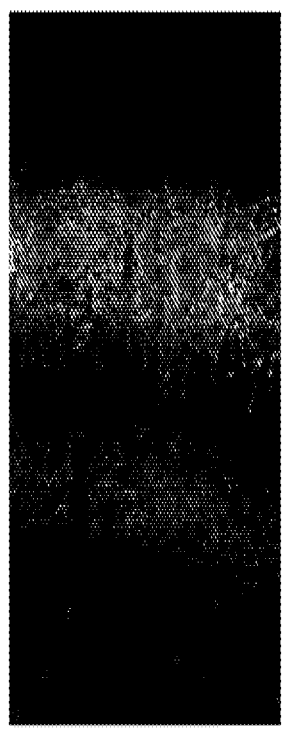
FIG. 11B shows opsin expression in visual cortex no overlap of GFP and mO2 is observed ratio of Chronos to Chrimson labeling can be tuned by titrating Cre plasmid.
Figure 11C:
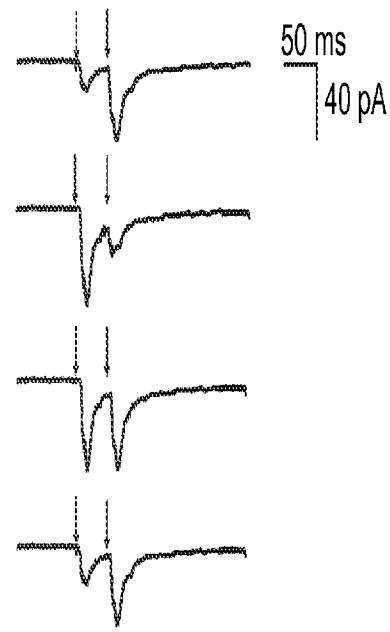
FIG. 11C shows voltage-clamped non-opsin-expressing neuron in layer 2/3 paired-pulse stimulation to demonstrate different synapses are selectively driven by blue and red light. blue: 0.2 mW mm$^{-2}$; red: 5 mW mm$^{-2}$. Arrows represent light application. First trace from top: first arrow indicates blue light, second arrow indicates red light; second trace from top: first arrow indicates red light, second arrow indicates blue light; third trace from top: both arrows represent red light; and fourth trace from top: both arrows represent blue light.

FIG. 11 illustrates results of studies of paired-pulse illumination in slice that differentially express Chrimson and Chronos in separate neurons. FIG. 11A shows a triple plasmid in utero electroporation scheme used to obtain non-overlapping expression of Chrimson and Chronos. FIG. 11B shows opsin expression in visual cortex no overlap of GFP and mO2 was observed ratio of Chronos to Chrimson labeling could be tuned by titrating Cre plasmid. FIG. 11C shows voltage-clamped non-opsin-expressing neuron in layer 2/3 paired-pulse stimulation to demonstrate different synapses were selectively driven by blue and red light. blue: 0.2 mW mm$^{-2}$; red: 5 mW mm$^{-2}$.

Example 11

Figure 12:
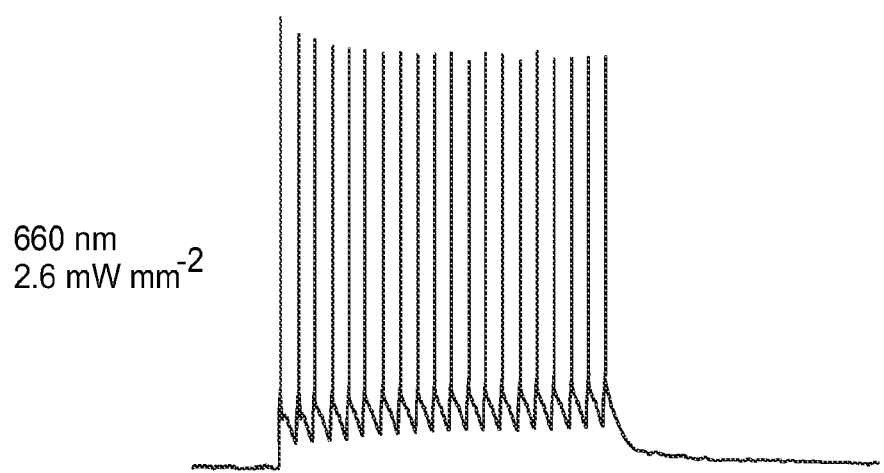
FIG. 12 is a trace illustrating that Chrimson can drive spikes in the far-red (660 nm) using 5 ms pulses at 2.6 mW mm$^{-2}$ in cultured hippocampal neurons.

Chrimson light-activated ion channels (ChR88) were expressed in cultured hippocampal neurons using neuron culture, transfection, infection, and imaging methods described in Example 1. In vitro whole cell patch claim recording and optical stimulation were conducted on the neurons using methods described in Example 1. FIG. 12 illustrated results that showed that Chrimson could drive spikes in the far-red (660 nm) using 5 ms pulses at 2.6 mW mm$^{-2}$ in cultured hippocampal neurons.

Example 12

Figures 13A, 13B, 13C:
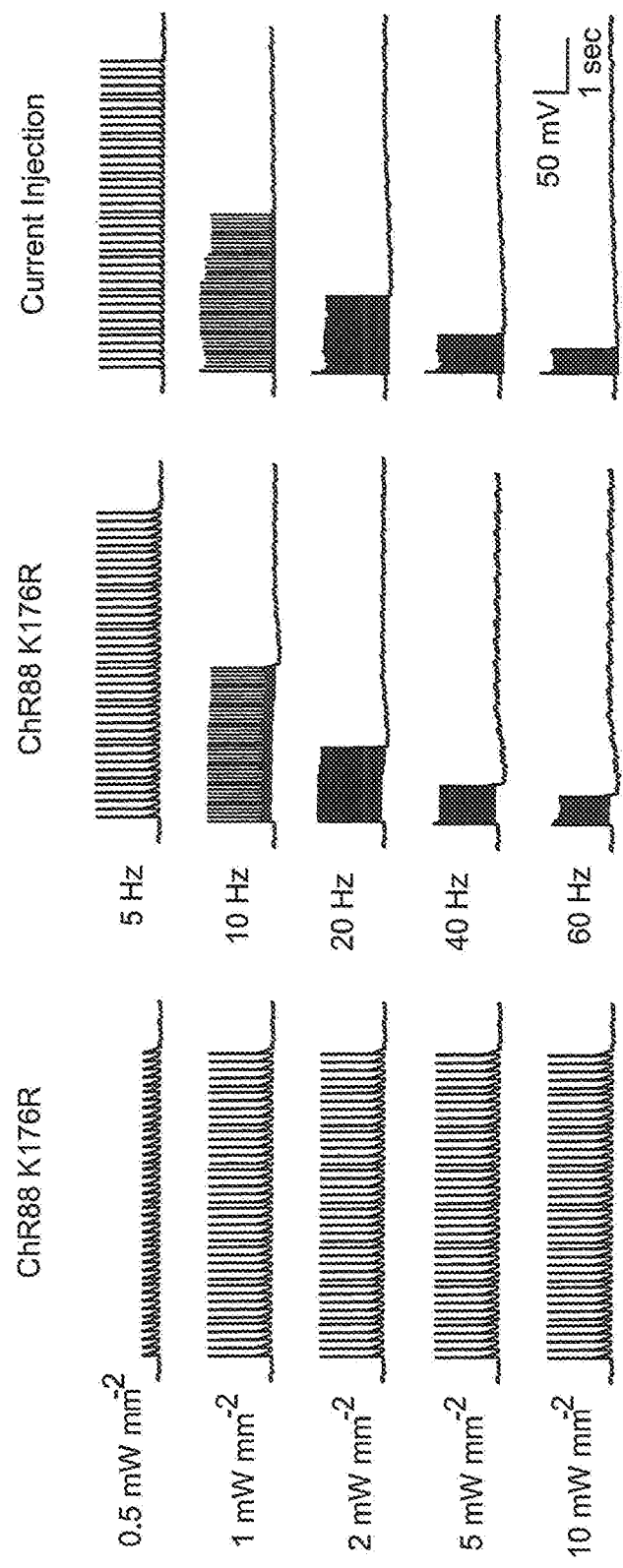
FIG. 13A shows that ChR88 K176R can reliably drive spikes from 1 to 10 mW mm$^{-2}$ at 625 nm 5 Hz stimulation.
FIG. 13B shows red light (625 nm) driven spike trains at various frequency for ChR88 K176R. 1 mW mm$^{-2}$ light power is used for all frequencies.
FIG. 13C shows current injection control to show the neuron is capable of spiking at the indicated frequencies.
Figure 14:
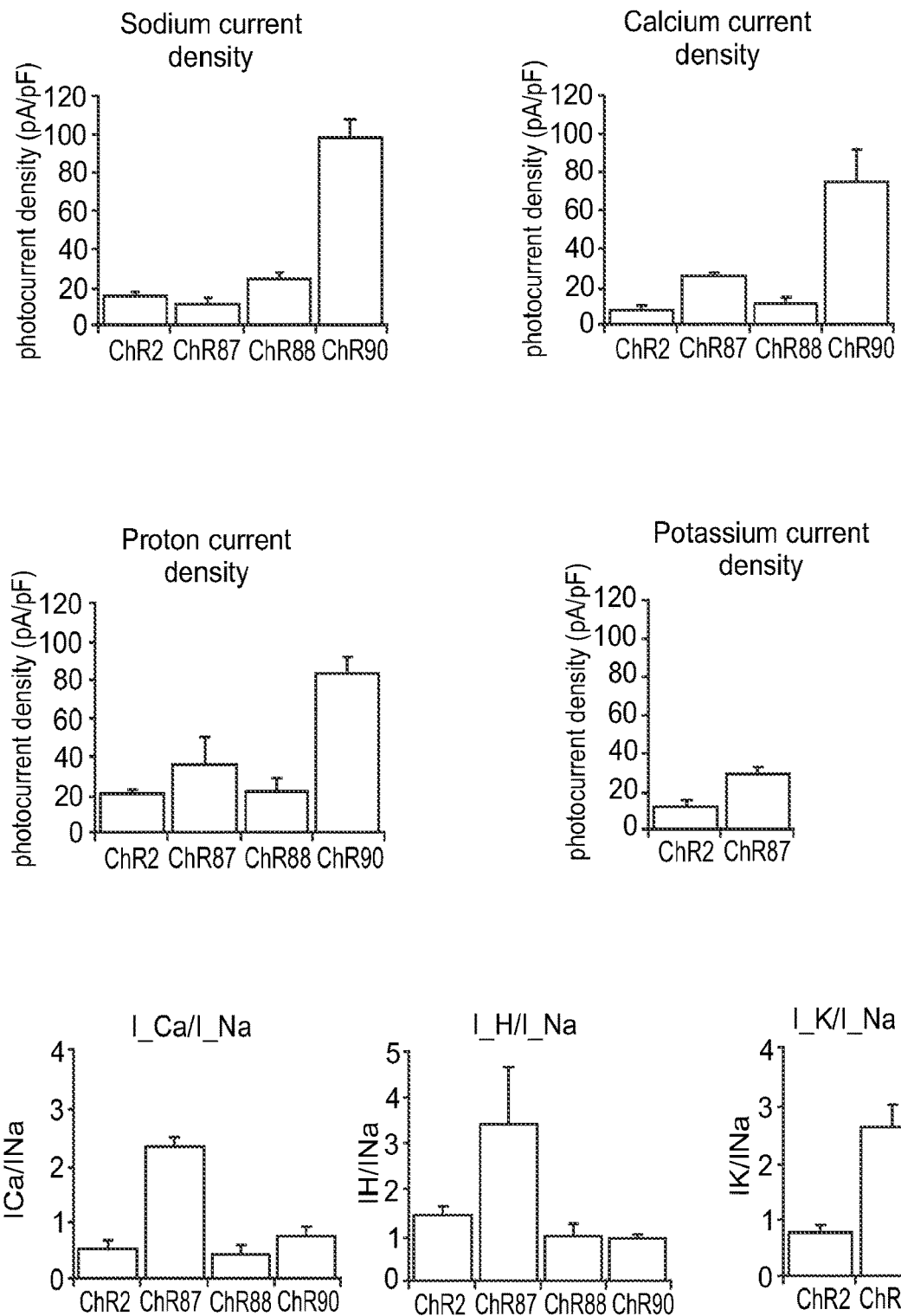
FIG. 14 provides graphs showing channelrhodopsin ion selectivity measured in HEK293FT cells. ChR88 and ChR90 have comparable ion selectivity as ChR2. However ChR87 has less sodium (Na) current compared to calcium (Ca), proton (H), and potassium (K) current.

Substituted Chrimson (ChR88) light activated ion channels, referred to as "ChR88 K176R", having an amino acid sequence set forth as SEQ ID NO:5, were expressed in cultured hippocampal neurons using neuron culture, transfection, infection, and imaging methods described in Example 1. In vitro whole cell patch claim recording and optical stimulation were conducted on the neurons using methods described in Example 1. FIG. 13 show results indicating that the ChR88 K176R mutant had improved kinetics (13 ms tau off) and could mediate high frequency spikes in cultured hippocampal neurons. Examples of current clamped traces of a single ChR88 K176R expressing neuron are shown. FIG. 13A shows that ChR88 K176R could reliably drive spikes from 1 to 10 mW mm$^{-2}$ at 625 nm 5 Hz stimulation. FIG. 13B shows red light (625 nm) driven spike trains at various frequencies for ChR88 K176R. 1 mW mm$^{-2}$ light power is used for all frequencies. FIG. 13C shows current injection control that demonstrated that the neuron was capable of spiking at the indicated frequencies.

Example 13

Ion conductance recording methods set forth in Example 1, were used to examine channel closing kinetics for ChR88, ChR90, ChR87, and ChR2 expressed in HEK293 cells. The closing kinetics were examined and compared. 2 ms light pulse was used to activate channelrhodopsin and all measurements were voltage clamped to −65 mV. Chronos had the fastest channel closing kinetics and is independent of voltage.

Example 14

Genes described under (a), (b) and (c) were expressed in cells using methods provided below.
Genes
a) The *Chloromonas subdivisa* gene referred to herein as ChR87 and having the amino acid sequence set forth herein as SEQ ID NO:5 and a mammalian codon-optimized DNA sequence set forth herein as SEQ ID NO:6;
b) The gene for *Chlamydomonas noctigama* referred to herein as ChR88 or Chrimson, and having the amino acid sequence set forth herein as SEQ ID NO:1 and a mammalian codon-optimized DNA sequence set forth herein as SEQ ID NO:2; and
c) The gene for *Stigeoclonium helveticum*, referred to herein as ChR90 or Chronos and having the amino acid sequence set forth herein as SEQ ID NO:3 and having a mammalian codon-optimized DNA sequence set forth herein as SEQ ID NO:4 are expressed in cells as follows.

Methods
(1) The opsin gene was cloned into a lentiviral or adeno-associated virus (AAV) packaging plasmid, or another desired expression plasmid, and then clone GFP downstream of the preferred gene, eliminating the stop codon of the opsin gene, thus creating a fusion protein.
(2) The viral or expression plasmid contained either a strong general promoter, a cell-specific promoter, or a strong general promoter followed by one more logical elements (such as a lox-stop-lox sequence, which will be removed by Cre recombinase selectively expressed in cells in a transgenic animal, or in a second virus, thus enabling the strong general promoter to then drive the gene.
(3) If using a viral plasmid, synthesize the viral vector using the viral plasmid.
(4) If using a virus, as appropriate for gene therapy (over 600 people have been treated with AAV carrying various genetic payloads to date, in 48 separate clinical trials, without a single adverse event), inject the virus using a small needle or cannula into the area of interest, thus delivering the gene encoding the opsin fusion protein into the cells of interest. If using another expression vector, directly electroporate or inject that vector into the cell or organism (for acutely expressing the opsin, or making a cell line, or a transgenic mouse or other animal).
(5) Illuminate with light. For Chronos, peak illumination wavelengths are 500 nm +/−15 nm. For Chrimson, peak illumination wavelengths are 590 nm +/−15 nm.
(6) To illuminate two different populations of cells (e.g., in a single tissue) with two different colors of light, first target one population with Chrimson, and the other population with Chronos, using two different viruses (e.g., with different coat proteins or promoters) or two different plasmids (e.g., with two different promoters). Then, after the molecule expresses, illuminate the tissue with 470±10 nm or 406±10 nm light to preferentially depolarize the Chronos-expressing cells, and illuminate the tissue with 406±10 nm or 660±10 nm light, to preferentially depolarize the Chrimson-expressing cells.
(7) The above wavelengths illustrate typical modes of operation, but are not meant to constrain the protocols that can be used. Either narrower or broader wavelengths, or to differently-centered illumination spectra, can be used. For prosthetic uses, the devices used to deliver light may be implanted. For drug screening, a xenon lamp or LED can be used to deliver the light.

Aspects of the invention include compositions of matter that have been reduced to practice, as described below:

Plasmids encoding for the above genes, have been prepared and used to deliver genes into cells, where the genes have been expressed. As an exemplary vector, lentiviruses carrying payloads encoding for the above genes have been prepared and used to deliver genes into cells resulting in expression of the light activated ion channels in the cells. In addition, adeno-associated viruses carrying payloads encoding for the above genes have been prepared and used to deliver genes into cells, resulting in the expression of the light activated ion channels in the cells. Cells have been prepared that express the light activated ion channels genes set forth in Example 2. Animals have been prepared that include cells that express the light activated ion channels genes disclosed herein.

Example 15

Two-color assays are performed. Chronos (for blue light activation) and Chrimson (for red light activation) are expressed in separate sets cells that represent non-overlapping neuronal populations. Following expression, the cell population is exposed to light and the wavelength and timing and "dose" of light is optimized using the following parameters.

The population is contacted with blue light having a wavelength between 450 nm to 500 nm, and with a pulse width of between 1 and 5 ms for activation. A pulse width of 5 ms provides for minimum sub-threshold crosstalk in the blue light, which is defined as <15 mV, <10 mV, and optimally as <5 mV.

(1) The maximum blue light power that can be used is determined using by patch clamping Chrimson expressing cells, illuminating with blue light and measuring voltage deflection. Optimally using blue light power such that maximum voltage deflection is <10 mV, usually 0.4 to 0.6 $mW/mm^2$.

(2) The optimal blue light power that can be used to drive Chronos is determined using the same conditions as above in (1), except using lower light power, such as 50 $\mu W/mm^2$ to 0.4 $mW/mm^2$, and optimally 0.2 $mW/mm^2$. Power depends on expression system and cell type used in the study.

The population is contacted with red light having a wavelength between 620 nm to 640 nm, and with a pulse width of between 1 and 5 ms for activation, which may be optimized at 5 ms. The optimal light power to drive chrimson in the red is determined by ramping light powers from 0.5 $mW/mm^2$ to 10 $mW/mm^2$. The method is optimized such that a minimum red light power is used to achieve 100% spiking for chrimson.

It is to be understood that the methods, compositions, and apparatus which have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference in their entirety.

We claim:

1. A method of altering ion conductivity of a membrane, the method comprising,
   a) contacting a light-activated ion channel polypeptide in a host membrane in a cell, wherein the light-activated ion channel polypeptide comprises an amino acid sequence having at least 90% amino acid identity to amino acids 86-320 of SEQ ID NO: 2 and at least 95% identity to the remaining amino acids of SEQ ID NO: 2 and wherein the light-activated ion channel polypeptide is part of a heterologous fusion protein; and
   b) contacting the light-activated ion channel polypeptide with a light that activates the light-activated ion channel and alters the ion conductivity of the membrane.

2. The method of claim 1, wherein the activating light has a wavelength between 365 nm and 700 nm.

3. The method of claim 1, wherein the amino acid sequence of the light-activated ion channel polypeptide comprises SEQ ID NO: 2.

4. The method of claim 1, wherein the amino acid sequence of the light-activated ion channel polypeptide has at least 95% amino acid identity to amino acids 86-320 of SEQ ID NO: 2 and at least 95% amino acid identity to the remaining amino acids in the sequence set forth as SEQ ID NO: 2.

5. The method of claim 1, wherein the amino acid sequence of the light-activated ion channel polypeptide comprises SEQ ID NO: 5.

6. The method of claim 1, wherein the amino acid sequence of the light-activated ion channel polypeptide has at least 99% identity to amino acids 86-320 of SEQ ID NO: 2 and 95% identity to the remaining amino acids in the sequence set forth as SEQ ID NO: 2.

7. The method of claim 1, wherein the host membrane is a cell membrane of a neuronal cell, a nervous system cell, a cardiac cell, a circulatory system cell, a visual system cell, or an auditory system cell.

8. The method of claim 1, wherein altering the ion conductivity of the membrane depolarizes the cell.

9. A light activated ion channel polypeptide, wherein the light-activated ion channel polypeptide comprises an amino acid sequence having at least 90% amino acid identity to amino acids 86-320 of SEQ ID NO: 2 and at least 95% identity to the remaining amino acids of SEQ ID NO: 2, wherein the light-activated ion channel polypeptide is part of a heterologous fusion protein.

10. The light activated ion channel polypeptide of claim 9, wherein contact of the ion channel polypeptide with a light having a wavelength between 365 nm and 700 nm activates the ion channel.

11. The light activated ion channel polypeptide of claim 9, wherein the amino acid sequence of the light-activated ion channel polypeptide comprises SEQ ID NO: 2.

12. The light-activated ion channel polypeptide of claim 9, wherein the light-activated ion channel polypeptide has at least 95% amino acid identity to amino acids 86-320 of SEQ ID NO: 2 and at least 95% identity to the remaining amino acids of SEQ ID NO: 2.

13. The light-activated ion channel polypeptide of claim 9, wherein the amino acid sequence of the light-activated ion channel polypeptide comprises SEQ ID NO: 5.

14. The light-activated ion channel polypeptide of claim 9, wherein the amino acid sequence of the light-activated ion channel polypeptide has at least 99% identity to amino acids 86-320 of SEQ ID NO: 2 and 95% identity to the remaining amino acids in the sequence set forth as SEQ ID NO: 2.

15. A method of assessing the effect of a candidate compound on ion conductivity of a membrane, the method comprising,
   a) contacting a test membrane in a cell, wherein the test membrane comprises a light-activated ion channel polypeptide, with light under conditions suitable for altering ion conductivity of the test membrane; wherein the light-activated ion channel polypeptide comprises an amino acid sequence having at least 90% amino acid identity to amino acids 86-320 of SEQ ID NO: 2 and at least 95% identity to the remaining amino acids of SEQ ID NO: 2 and the light-activated ion channel polypeptide is part of a heterologous fusion protein;
   b) contacting the test membrane with a candidate compound; and
   c) identifying the presence or absence of a change in ion conductivity of the test membrane contacted with the light and the candidate compound compared to ion conductivity in a control cell membrane contacted with the light and not contacted with the candidate compound;
wherein a change in the ion conductivity in the test membrane compared to the control indicates an effect of the candidate compound on the ion conductivity of the test membrane.

16. The light-activated ion channel polypeptide of claim 9, wherein the light-activated ion channel polypeptide is in a cell, and optionally the cell is a mammalian cell, and optionally the cell is an excitable cell.

17. The method of claim 15, wherein the amino acid sequence of the light-activated ion channel polypeptide has at least 95% identity to amino acids 86-320 of SEQ ID NO: 2 and 95% identity to the remaining amino acids in the sequence set forth as SEQ ID NO: 2.

18. The method of claim 15, wherein the amino acid sequence of the light-activated ion channel polypeptide has at least 99% identity to amino acids 86-320 of SEQ ID NO: 2 and 95% identity to the remaining amino acids in the sequence set forth as SEQ ID NO: 2.

19. The light-activated ion channel polypeptide of claim 9, wherein the light-activated ion channel polypeptide has at least 99% amino acid identity to amino acids 86-320 of SEQ ID NO: 2 and at least 98% identity to the remaining amino acids of SEQ ID NO: 2.

20. The light-activated ion channel polypeptide of claim 9, wherein the light-activated ion channel polypeptide has at least 99% amino acid identity to amino acids 86-320 of SEQ ID NO: 2 and at least 99% identity to the remaining amino acids of SEQ ID NO: 2.

21. The method of claim 1, wherein the light-activated ion channel polypeptide has at least 99% amino acid identity to amino acids 86-320 of SEQ ID NO: 2 and at least 98% identity to the remaining amino acids of SEQ ID NO: 2.

22. The method of claim 1, wherein the light-activated ion channel polypeptide has at least 99% amino acid identity to amino acids 86-320 of SEQ ID NO: 2 and at least 99% identity to the remaining amino acids of SEQ ID NO: 2.

23. The method of claim 15, wherein the light-activated ion channel polypeptide has at least 99% amino acid identity to amino acids 86-320 of SEQ ID NO: 2 and at least 98% identity to the remaining amino acids of SEQ ID NO: 2.

24. The method of claim 15, wherein the light-activated ion channel polypeptide has at least 99% amino acid identity to amino acids 86-320 of SEQ ID NO: 2 and at least 99% identity to the remaining amino acids of SEQ ID NO: 2.

25. A light-activated ion channel polypeptide comprising the amino acid sequence set forth as SEQ ID NO: 5.

* * * * *

UNITED STATES PATENT AND TRADEMARK OFFICE
CERTIFICATE OF CORRECTION

PATENT NO. : 10,472,398 B2
APPLICATION NO. : 14/357635
DATED : November 12, 2019
INVENTOR(S) : Nathan Klapoetke et al.

Page 1 of 1

It is certified that error appears in the above-identified patent and that said Letters Patent is hereby corrected as shown below:

On the Title Page

Item (72), Inventors; Line 5, please amend:
"Edmontn" to -- Edmonton --

Signed and Sealed this
Fourth Day of February, 2020

Andrei Iancu
*Director of the United States Patent and Trademark Office*